(12) United States Patent
Lagu et al.

(10) Patent No.: US 7,723,326 B2
(45) Date of Patent: May 25, 2010

(54) HETEROCYCLIC AMIDE DERIVATIVES AS RXR AGONISTS FOR THE TREATMENT OF DYSLIPIDEMIA, HYPERCHOLESTEROLEMIA AND DIABETES

(75) Inventors: Bharat Lagu, Hillsborough, NJ (US); Rimma Lebedev, Basking Ridge, NJ (US); Barbara Pio, Hillsborough, NJ (US)

(73) Assignee: Janssen Pharmaceutica N.V., New Brunswick, NJ (US)

( * ) Notice: Subject to any disclaimer, the term of this patent is extended or adjusted under 35 U.S.C. 154(b) by 652 days.

(21) Appl. No.: 11/534,957

(22) Filed: Sep. 25, 2006

(65) Prior Publication Data

US 2007/0078129 A1 Apr. 5, 2007

Related U.S. Application Data

(60) Provisional application No. 60/722,783, filed on Sep. 30, 2005.

(51) Int. Cl.
*C07D 265/12* (2006.01)
*C07D 265/36* (2006.01)
*A61K 31/538* (2006.01)

(52) U.S. Cl. .................. 514/230.5; 544/105
(58) Field of Classification Search ................ 544/105; 514/230.5
See application file for complete search history.

(56) References Cited

U.S. PATENT DOCUMENTS

| | | | |
|---|---|---|---|
| 5,739,338 A | 4/1998 | Beard et al. | |
| 6,048,873 A | 4/2000 | Vasudevan et al. | |
| 6,444,668 B1 | 9/2002 | Grubb et al. | |

FOREIGN PATENT DOCUMENTS

| | | |
|---|---|---|
| EP | 1117648 | 8/2003 |
| WO | WO 01/16122 A1 | 3/2001 |
| WO | WO 01/16123 A1 | 3/2001 |

OTHER PUBLICATIONS

Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*
Chalmers (TiPS vol. 17, pp. 166-172 Apr. 1996).*
Unger, R.H., "Hyperglycaemia as an inducer as well as a consequence of impaired islet cell function and insulin resistance: implications for the management of diabetes." *Diabetologia*, 1985, vol. 28, pp. 119-121.
Rossetti, L. et al., "Glucose Toxicity" *Diabetes Care*, 1990, vol. 13, pp. 610-630, No. 6.
Mangelsdorf, D.J. et al., "The RXR Heterodimers and Orphan Receptors." *Cell*, 1995, vol. 83, pp. 841-850.
Kastner, P. et al., "Nonsteroid Nuclear Receptors: What are Genetic Studies Telling Us about Their Role in Real Life"? *Cell*, 1995, vol. 83, pp. 859-869.
Hibi, S. et al.: "Syntheses and Structure-Activity Relationships of Novel Retinoid X Receptor". *Journal of Medicinal Chemistry, American Chemical Society*, 1998, vol. 41, No. 17, pp. 3245-3252, XP002131548, ISSN:0022-2623.
Haffner, C.D. et al: "Structure-Based Design of Potent Retinoid X Receptor α Agonists".*Journal of Medicinal Chemistry*, vol. 47 No. 8, pp. 2010-2029 Coden: JMCMAR; ISSN:0022-2623, 2004, XP002415204.
Pogenberg, V. et al.: "Characterization of the Interaction between Retinoic Acid Receptor/Retinoid X Receptor (RAR.RXR) Heterodimers and Transcriptional Coactivators through Structural and Fluorescence Anisotropy Studies". *Journal of Biological Chemistry*, 2005, vol. 280, No. 2, pp. 1625-1633 Coden: JBCHA3; ISSN:0021-9258, January, XP002415142.
PCT International Search Report No. PCT/US2006/037322 dated Mar. 14, 2007, which relates to U.S. Appl. No. 11/534,957.
Denmark et al., "Cyclopropanation with Diazomethane and Bis(oxazoline)palladium(II) Complexes.", Journal of Organic Chemistry, 1997, vol. 62(10), pp. 3375-3389.
Charette et al., "Bis(oxazoline)•copper(I)-catalyzed enantioselective cyclopropanation of cinnamate esters with diazomethane.", Tetrahedron: Asymmetry, 2003, vol. 14(7), pp. 867-872.
Eilbracht et al., Tandem silylformylation/Wittig Olefination of Terminal Alkynes: Stereoselective Synthesis of 2,4-Dienoic Esters., European Journal of Organic Chemistry, 2000(7), pp. 1131-1135.
Nikam et al., "Novel Use of Substituted 1,4-Dihydrobenz[*d*]{1,3}oxazin-2-ones in the Synthesis of Importatn Aminomethyl *o*-Nitroanilines.", J. Org. Chem., 1997, vol. 62(26), pp. 9331-9934.

* cited by examiner

*Primary Examiner*—Kahsay T Habte
(74) *Attorney, Agent, or Firm*—Jeremy K. McKown

(57) ABSTRACT

The present invention relates to compounds of Formula (I),

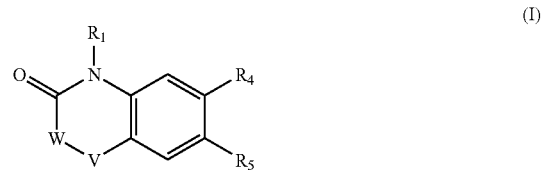

(I)

methods for preparing these compounds, compositions, intermediates and derivatives thereof and for treating RXR mediated disorders. More particularly, the compounds of the present invention are RXR agonists useful for treating RXR mediated disorders.

28 Claims, No Drawings

SEQUENCE LISTING

<160> NUMBER OF SEQ ID NOS: 46

<210> SEQ ID NO 1
<211> LENGTH: 43
<212> TYPE: DNA
<213> ORGANISM: Artificial Sequence
<220> FEATURE:
<223> OTHER INFORMATION: Synthetic

<400> SEQUENCE: 1
cgggtaacgg aaacaggggt tgtttttctc ttggaaagaa agt            43

<210> SEQ ID NO 2
<211> LENGTH: 42
<212> TYPE: DNA
<213> ORGANISM: Artificial Sequence
<220> FEATURE:
<223> OTHER INFORMATION: Synthetic

<400> SEQUENCE: 2
tccgggagcc tccccaggag tttttttctct tggaaagaaa gt             42

<210> SEQ ID NO 3
<211> LENGTH: 41
<212> TYPE: DNA
<213> ORGANISM: Artificial Sequence
<220> FEATURE:
<223> OTHER INFORMATION: Synthetic

<400> SEQUENCE: 3
gccagtttct cccttggtag tttttctctt ggaaagaaag t               41

<210> SEQ ID NO 4
<211> LENGTH: 39
<212> TYPE: DNA
<213> ORGANISM: Artificial Sequence
<220> FEATURE:
<223> OTHER INFORMATION: Synthetic

<400> SEQUENCE: 4
ctccttgctc gggaagggtt tttctcttgg aaagaaagt                  39

<210> SEQ ID NO 5
<211> LENGTH: 40
<212> TYPE: DNA
<213> ORGANISM: Artificial Sequence
<220> FEATURE:
<223> OTHER INFORMATION: Synthetic

<400> SEQUENCE: 5
aacagctcct gggccagagt ttttctcttg gaaagaaagt                 40

<210> SEQ ID NO 6
<211> LENGTH: 43
<212> TYPE: DNA
<213> ORGANISM: Artificial Sequence
<220> FEATURE:
<223> OTHER INFORMATION: Synthetic

<400> SEQUENCE: 6
ttcagccccc ctccctcggg atttttttctc ttggaaagaa agt            43

<210> SEQ ID NO 7
<211> LENGTH: 40

```
<212> TYPE: DNA
<213> ORGANISM: Artificial Sequence
<220> FEATURE:
<223> OTHER INFORMATION: Synthetic

<400> SEQUENCE: 7
atgcgggaaa gaggactagt ttttctcttg gaaagaaagt                    40

<210> SEQ ID NO 8
<211> LENGTH: 41
<212> TYPE: DNA
<213> ORGANISM: Artificial Sequence
<220> FEATURE:
<223> OTHER INFORMATION: Synthetic

<400> SEQUENCE: 8
gttcacctca gccatgacct tttttctctt ggaaagaaag t                  41

<210> SEQ ID NO 9
<211> LENGTH: 43
<212> TYPE: DNA
<213> ORGANISM: Artificial Sequence
<220> FEATURE:
<223> OTHER INFORMATION: Synthetic

<400> SEQUENCE: 9
catgccttcc agatcatgga acttttctc ttggaaagaa agt                 43

<210> SEQ ID NO 10
<211> LENGTH: 42
<212> TYPE: DNA
<213> ORGANISM: Artificial Sequence
<220> FEATURE:
<223> OTHER INFORMATION: Synthetic

<400> SEQUENCE: 10
gcgagccaca atggattttt tttaggcata ggacccgtgt ct                 42

<210> SEQ ID NO 11
<211> LENGTH: 44
<212> TYPE: DNA
<213> ORGANISM: Artificial Sequence
<220> FEATURE:
<223> OTHER INFORMATION: Synthetic

<400> SEQUENCE: 11
ctccgagcat ctgagaacag tttttaggca taggacccgt gtct               44

<210> SEQ ID NO 12
<211> LENGTH: 45
<212> TYPE: DNA
<213> ORGANISM: Artificial Sequence
<220> FEATURE:
<223> OTHER INFORMATION: Synthetic

<400> SEQUENCE: 12
tcagaacttt gcgcatgtcc tttttaggc ataggacccg tgtct               45

<210> SEQ ID NO 13
<211> LENGTH: 50
<212> TYPE: DNA
<213> ORGANISM: Artificial Sequence
<220> FEATURE:
<223> OTHER INFORMATION: Synthetic
```

<400> SEQUENCE: 13
ggatttcttg atctgctgta atgttcttttt taggcatagg acccgtgtct                     50

<210> SEQ ID NO 14
<211> LENGTH: 47
<212> TYPE: DNA
<213> ORGANISM: Artificial Sequence
<220> FEATURE:
<223> OTHER INFORMATION: Synthetic

<400> SEQUENCE: 14
aaggtttcat tgtccaccag gaattttttag gcataggacc cgtgtct                       47

<210> SEQ ID NO 15
<211> LENGTH: 47
<212> TYPE: DNA
<213> ORGANISM: Artificial Sequence
<220> FEATURE:
<223> OTHER INFORMATION: Synthetic

<400> SEQUENCE: 15
ggttgtgata caggaaccca gagtttttag gcataggacc cgtgtct                         47

<210> SEQ ID NO 16
<211> LENGTH: 50
<212> TYPE: DNA
<213> ORGANISM: Artificial Sequence
<220> FEATURE:
<223> OTHER INFORMATION: Synthetic

<400> SEQUENCE: 16
gtccacagta gactttggga gagagatttt taggcatagg acccgtgtct                      50

<210> SEQ ID NO 17
<211> LENGTH: 46
<212> TYPE: DNA
<213> ORGANISM: Artificial Sequence
<220> FEATURE:
<223> OTHER INFORMATION: Synthetic

<400> SEQUENCE: 17
tgacatcagc cctcagcatc tttttttagg cataggaccc gtgtct                          46

<210> SEQ ID NO 18
<211> LENGTH: 49
<212> TYPE: DNA
<213> ORGANISM: Artificial Sequence
<220> FEATURE:
<223> OTHER INFORMATION: Synthetic

<400> SEQUENCE: 18
cttgtcaaat gtaactggta gcctttttttt aggcatagga cccgtgtct                      49

<210> SEQ ID NO 19
<211> LENGTH: 47
<212> TYPE: DNA
<213> ORGANISM: Artificial Sequence
<220> FEATURE:
<223> OTHER INFORMATION: Synthetic

<400> SEQUENCE: 19
ctgattttga tccattgcac agattttttag gcataggacc cgtgtct                        47

<210> SEQ ID NO 20
<211> LENGTH: 45
<212> TYPE: DNA
<213> ORGANISM: Artificial Sequence
<220> FEATURE:
<223> OTHER INFORMATION: Synthetic

<400> SEQUENCE: 20
ggcttcagga tgtccatgtt gttttttaggc ataggacccg tgtct                45

<210> SEQ ID NO 21
<211> LENGTH: 52
<212> TYPE: DNA
<213> ORGANISM: Artificial Sequence
<220> FEATURE:
<223> OTHER INFORMATION: Synthetic

<400> SEQUENCE: 21
agatgtagag tttagtgttc tcaggatttt tttaggcata ggaccegtgt ct          52

<210> SEQ ID NO 22
<211> LENGTH: 42
<212> TYPE: DNA
<213> ORGANISM: Artificial Sequence
<220> FEATURE:
<223> OTHER INFORMATION: Synthetic

<400> SEQUENCE: 22
ttttgtggct tcggccagtt tttaggcata ggacccgtgt ct                    42

<210> SEQ ID NO 23
<211> LENGTH: 46
<212> TYPE: DNA
<213> ORGANISM: Artificial Sequence
<220> FEATURE:
<223> OTHER INFORMATION: Synthetic

<400> SEQUENCE: 23
tcccaagact atgcagcaat gttttttagg cataggaccc gtgtct                46

<210> SEQ ID NO 24
<211> LENGTH: 46
<212> TYPE: DNA
<213> ORGANISM: Artificial Sequence
<220> FEATURE:
<223> OTHER INFORMATION: Synthetic

<400> SEQUENCE: 24
gtcactccag cttctcatgc tgttttttagg cataggaccc gtgtct               46

<210> SEQ ID NO 25
<211> LENGTH: 46
<212> TYPE: DNA
<213> ORGANISM: Artificial Sequence
<220> FEATURE:
<223> OTHER INFORMATION: Synthetic

<400> SEQUENCE: 25
gaaacatcac ctcctgtcgc attttttagg cataggaccc gtgtct                46

<210> SEQ ID NO 26
<211> LENGTH: 43
<212> TYPE: DNA

<213> ORGANISM: Artificial Sequence
<220> FEATURE:
<223> OTHER INFORMATION: Synthetic

<400> SEQUENCE: 26
gcctggtaga tttgggtggt ttttaggcat aggacccgtg tct        43

<210> SEQ ID NO 27
<211> LENGTH: 47
<212> TYPE: DNA
<213> ORGANISM: Artificial Sequence
<220> FEATURE:
<223> OTHER INFORMATION: Synthetic

<400> SEQUENCE: 27
gcccgcagac aatacgagac acattttag gcataggacc cgtgtct        47

<210> SEQ ID NO 28
<211> LENGTH: 45
<212> TYPE: DNA
<213> ORGANISM: Artificial Sequence
<220> FEATURE:
<223> OTHER INFORMATION: Synthetic

<400> SEQUENCE: 28
ggctttgtag ttgttgtcct cttttaggc ataggacccg tgtct        45

<210> SEQ ID NO 29
<211> LENGTH: 43
<212> TYPE: DNA
<213> ORGANISM: Artificial Sequence
<220> FEATURE:
<223> OTHER INFORMATION: Synthetic

<400> SEQUENCE: 29
tgccattgcc tccaaagagt ttttaggcat aggacccgtg tct        43

<210> SEQ ID NO 30
<211> LENGTH: 46
<212> TYPE: DNA
<213> ORGANISM: Artificial Sequence
<220> FEATURE:
<223> OTHER INFORMATION: Synthetic

<400> SEQUENCE: 30
aaggtttcag catcttcctc agttttagg cataggaccc gtgtct        46

<210> SEQ ID NO 31
<211> LENGTH: 53
<212> TYPE: DNA
<213> ORGANISM: Artificial Sequence
<220> FEATURE:
<223> OTHER INFORMATION: Synthetic

<400> SEQUENCE: 31
tgcagtaagg agttgtagag ttgtcatagt ttttaggcat aggacccgtg tct        53

<210> SEQ ID NO 32
<211> LENGTH: 48
<212> TYPE: DNA
<213> ORGANISM: Artificial Sequence
<220> FEATURE:
<223> OTHER INFORMATION: Synthetic

<400> SEQUENCE: 32
actccaaatt cttcatcaaa tcatttttta ggcataggac ccgtgtct               48

<210> SEQ ID NO 33
<211> LENGTH: 46
<212> TYPE: DNA
<213> ORGANISM: Artificial Sequence
<220> FEATURE:
<223> OTHER INFORMATION: Synthetic

<400> SEQUENCE: 33
cggcttcaga gctttccaga tatttttagg cataggaccc gtgtct                46

<210> SEQ ID NO 34
<211> LENGTH: 18
<212> TYPE: DNA
<213> ORGANISM: Artificial Sequence
<220> FEATURE:
<223> OTHER INFORMATION: Synthetic

<400> SEQUENCE: 34
gttaaagttt ccaacaac                                               18

<210> SEQ ID NO 35
<211> LENGTH: 14
<212> TYPE: DNA
<213> ORGANISM: Artificial Sequence
<220> FEATURE:
<223> OTHER INFORMATION: Synthetic

<400> SEQUENCE: 35
tgtataaaag aagc                                                   14

<210> SEQ ID NO 36
<211> LENGTH: 21
<212> TYPE: DNA
<213> ORGANISM: Artificial Sequence
<220> FEATURE:
<223> OTHER INFORMATION: Synthetic

<400> SEQUENCE: 36
tcatgctggt gtctttctgg c                                           21

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37
atcttgaagc ttcaagtttg agct                                        24

<210> SEQ ID NO 38
<211> LENGTH: 21
<212> TYPE: DNA
<213> ORGANISM: Artificial Sequence
<220> FEATURE:
<223> OTHER INFORMATION: Synthetic

<400> SEQUENCE: 38
gcaaaaatac cttgtggaga a                                           21

```
<210> SEQ ID NO 39
<211> LENGTH: 24
<212> TYPE: DNA
<213> ORGANISM: Artificial Sequence
<220> FEATURE:
<223> OTHER INFORMATION: Synthetic

<400> SEQUENCE: 39
ggtcaccaag ttgaatcatc tctt                                           24

<210> SEQ ID NO 40
<211> LENGTH: 23
<212> TYPE: DNA
<213> ORGANISM: Artificial Sequence
<220> FEATURE:
<223> OTHER INFORMATION: Synthetic

<400> SEQUENCE: 40
gccacaaagc tcagaaactt ctt                                            23

<210> SEQ ID NO 41
<211> LENGTH: 24
<212> TYPE: DNA
<213> ORGANISM: Artificial Sequence
<220> FEATURE:
<223> OTHER INFORMATION: Synthetic

<400> SEQUENCE: 41
gaacgaagta ctcgctctgc tgca                                           24

<210> SEQ ID NO 42
<211> LENGTH: 27
<212> TYPE: DNA
<213> ORGANISM: Artificial Sequence
<220> FEATURE:
<223> OTHER INFORMATION: Synthetic

<400> SEQUENCE: 42
aggagctgga gctgttcaca ttggtca                                        27

<210> SEQ ID NO 43
<211> LENGTH: 22
<212> TYPE: DNA
<213> ORGANISM: Artificial Sequence
<220> FEATURE:
<223> OTHER INFORMATION: Synthetic

<400> SEQUENCE: 43
ataccagttg agagacttga tc                                             22

<210> SEQ ID NO 44
<211> LENGTH: 24
<212> TYPE: DNA
<213> ORGANISM: Artificial Sequence
<220> FEATURE:
<223> OTHER INFORMATION: Synthetic

<400> SEQUENCE: 44
atacaggatc ttcccaacga gcag                                           24

<210> SEQ ID NO 45
<211> LENGTH: 25
<212> TYPE: DNA
<213> ORGANISM: Artificial Sequence
<220> FEATURE:
```

```
<223> OTHER INFORMATION: Synthetic

<400> SEQUENCE: 45
gccttgtggc tggagtgtca ggtgt                                25

<210> SEQ ID NO 46
<211> LENGTH: 23
<212> TYPE: DNA
<213> ORGANISM: Artificial Sequence
<220> FEATURE:
<223> OTHER INFORMATION: Synthetic

<400> SEQUENCE: 46
acagccagtt cctggaaggt ctt                                  23
```

HETEROCYCLIC AMIDE DERIVATIVES AS RXR AGONISTS FOR THE TREATMENT OF DYSLIPIDEMIA, HYPERCHOLESTEROLEMIA AND DIABETES

CROSS REFERENCE TO RELATED APPLICATION

This application claims the benefit of U.S. Provisional Application No. 60/722,783, filed Sep. 30, 2005, which is incorporated by reference herein.

FIELD OF THE INVENTION

The present invention relates to certain novel compounds, methods for preparing compounds, compositions, intermediates and derivatives thereof and for treating cancer and metabolic disorders. More particularly, the compounds of the present invention are Retinoid X Receptor (RXR) agonists useful for treating, ameliorating, preventing and/or inhibiting the onset of cancer and metabolic disorders such as diabetes, dyslipidemia, and hypercholesterolemia.

BACKGROUND OF THE INVENTION

Diabetes is a chronic disorder affecting carbohydrate, fat and protein metabolism in animals.

Type I diabetes mellitus, which comprises approximately 10% of all diabetes cases, was previously referred to as insulin-dependent diabetes mellitus ("IDDM") or juvenile-onset diabetes. This disease is characterized by a progressive loss of insulin secretory function by beta cells of the pancreas. This characteristic is also shared by non-idiopathic, or "secondary," diabetes having its origins in pancreatic disease. Type I diabetes mellitus is associated with the following clinical signs or symptoms: persistently elevated plasma glucose concentration or hyperglycemia; polyuria; polydipsia and/or hyperphagia; chronic microvascular complications such as retinopathy, nephropathy and neuropathy; and macrovascular complications such as hyperlipidemia and hypertension which can lead to blindness, end-stage renal disease, limb amputation and myocardial infarction.

Type II diabetes mellitus (non-insulin-dependent diabetes mellitus or NIDDM) is a metabolic disorder involving the dysregulation of glucose metabolism and impaired insulin sensitivity. Type II diabetes mellitus usually develops in adulthood and is associated with the body's inability to utilize or make sufficient insulin. In addition to the insulin resistance observed in the target tissues, patients suffering from type II diabetes mellitus have a relative insulin deficiency—that is, patients have lower than predicted insulin levels for a given plasma glucose concentration. Type II diabetes mellitus is characterized by the following clinical signs or symptoms: persistently elevated plasma glucose concentration or hyperglycemia; polyuria; polydipsia and/or hyperphagia; chronic microvascular complications such as retinopathy, nephropathy and neuropathy; and macrovascular complications such as hyperlipidemia and hypertension which can lead to blindness, end-stage renal disease, limb amputation and myocardial infarction.

Dyslipidemia, or dislipidemia, includes lipoprotein overproduction or deficiency; sometimes associated with diabetes, it is a common cause of lipidemia. For example, it is recommended for adults with diabetes to have their levels of LDL, HDL, total cholesterol, and triglyceride measured regularly. The desirable levels for such adults can be: LDL—less than 100 mg/dL (2.60 mmol/L), HDL—no less than 40 mg/dL (1.02 mmol/L), and triglyceride—less than 150 mg/dL (1.7 mmol/L). When blood cholesterol is too high, the condition is referred to as hypercholesterolemia. In one instance, dyslipidemia can include hypertriglyceridemia, and mixed hyperlipidemia. In terms of the above indices, dyslipidemia (including hyperlipidemia) may be one or more of the following conditions: low HDL (<35 or 40 mg/dl), high triglycerides (>200 mg/dl), and high LDL (>150 mg/dl).

Compounds having retinoid-like activity are useful for preventing, treating or at least alleviating the symptoms and conditions of numerous diseases and conditions. There are two main types of retinoid receptors: the Retinoid X Receptors (RXRs) including their subtypes RXR$\alpha$, $\beta$, $\gamma$, and the Retinoic Acid Receptors (RARs), also including their subtypes RAR$\alpha$, $\beta$, $\gamma$. Retinoid receptor modulators are useful in a variety of conditions including, but not limited to, metabolic disorders, such as type II diabetes, dyslipidemia, hypercholesterolemia, and atherosclerosis, and various cancerous and precancerous conditions in the breast, skin, prostate, cervix, uterus, colon, bladder, esophagus, stomach, lung, larynx, oral cavity, blood and/or lymphatic systems. For example, RXRs belong to the nuclear receptor superfamily and consist of a large number of ligand-regulated transcription factors that mediate the diverse physiological functions of steroid hormones, retinoids, thyroid hormone, and vitamin D in embryonic development, growth, differentiation, apoptosis, and homeostasis (Mangelsdorf, D. J., et al., Cell 83, 841-850 (1995); Kastner, P., et al., Cell 83, 859-869 (1995)).

RXR modulators have been identified as insulin sensitizing drugs. All diabetics, regardless of their genetic and environmental backgrounds, have in common an apparent lack of insulin or inadequate insulin function. Because transfer of glucose from the blood into muscle and fatty tissue is insulin dependent, diabetics lack the ability to utilize glucose adequately, which leads to undesired accumulation of glucose in the blood, or hyperglycemia. Chronic hyperglycemia leads to decrease in insulin secretion and contributes to increased insulin resistance, and as a result, the blood glucose concentration is increased so that diabetes is self-exacerbated (Diabetologia, 1985, "Hyperglycaemia as an inducer as well as a consequence of impaired isle cell function and insulin resistance: implications for the management of diabetes", Vol. 28, p. 119); Diabetes Cares, 1990, Vol. 13, No. 6, "Glucose Toxicity", pp. 610-630). Therefore, by treating hyperglycemia, the aforementioned self-exacerbating cycle can be interrupted so that prophylaxis or treatment of diabetes is made possible.

U.S. Pat. No. 6,048,873 to Vasudevan et al. is directed to novel compounds having retinoid-like biological activity. More specifically, it is directed to compounds that include a substituted tetrahydroquinoline moiety and a 2,4-pentadienoic acid moiety and have selective activity for retinoid X receptors.

U.S. Pat. No. 5,739,338 to Beard et al. is directed to novel compounds having retinoid-like, retinoid antagonist and/or retinoid inverse-agonist-like biological activity. More specifically, it is directed to aryl substituted tetrahydroquinoline derivatives which bind to retinoid receptors and have retinoid-like, retinoid antagonist or retinoid inverse agonist-like biological activity.

There is a continuing need for new RXR agonists. There is also a need for RXR agonists useful for the treatment of conditions including but not limited to cancer and metabolic disorders such as diabetes, dyslipidemia, and hypercholesterolemia.

SUMMARY OF THE INVENTION

In its many embodiments, the present invention provides a novel class of compounds useful as, for example, retinoid x receptor agonists, methods of preparing such compounds, pharmaceutical compositions comprising one or more such compounds, methods of preparing pharmaceutical compositions comprising one or more such compounds, and methods of treatment, prevention, inhibition or amelioration of one or more diseases associated with the retinoid x receptors using such compounds or pharmaceutical compositions.

One aspect of the present invention features a compound of Formula (I)

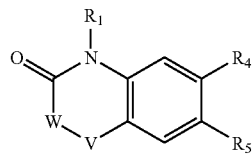

(I)

wherein
$R_1$ is H or $C_{1-3}$alkyl;
W is —O—, —C(O)—, or

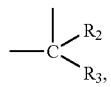

with the provisos that when W is —O— or —(O)—, then V is not —O—, and when W is

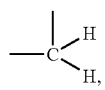

then V is not

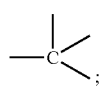

V is —O—, —N($R_2$)—, or

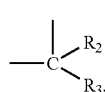

with the proviso that when V is —O—, W is not —O— or —(O)—, wherein $R_2$ and $R_3$ can be the same or different, each being independently selected from H and optionally substituted $C_{1-3}$alkyl;
$R_4$ is independently

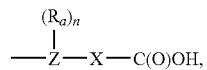

wherein
Z is selected from

X is selected from a bond, optionally substituted —O—$C_{1-5}$alkylene, and optionally substituted $C_{1-6}$alkylene; and
$R_a$ is H or optionally substituted $C_{1-3}$alkoxy; and
n is 1, 2, or 3;
or alternatively $R_4$ is H or optionally substituted $C_{1-3}$alkyl;
with the proviso that when $R_4$ is

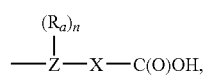

then $R_5$ cannot be

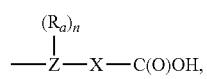

provided further that when $R_4$ is H or optionally substituted $C_{1-3}$alkyl, then $R_5$ cannot be H or optionally substituted $C_{1-3}$alkyl;
and
$R_5$ is independently

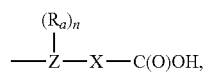

wherein
Z is selected from

X is selected from a bond, optionally substituted —O—$C_{1-5}$alkylene, and optionally substituted $C_{1-6}$alkylene; and $R_a$ is H or optionally substituted $C_{1-3}$alkoxy; and
n is 1, 2, or 3;
or alternatively $R_5$ is H or optionally substituted $C_{1-3}$alkyl; with the proviso that when $R_5$ is

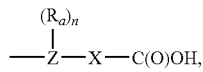

then $R_4$ cannot be

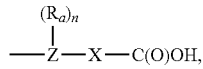

provided further that when $R_5$ is H or optionally substituted $C_{1-3}$alkyl, then $R_4$ cannot be H or optionally substituted $C_{1-3}$alkyl;

or an optical isomer, enantiomer, diastereomer, racemate, or pharmaceutically acceptable salt thereof.

Another aspect of the present invention features a pharmaceutical composition comprising at least one compound of Formula (I) and at least one pharmaceutically acceptable carrier.

One embodiment of the invention is a method for treating, preventing or ameliorating a RXR mediated condition in a subject in need thereof comprising administering to the subject a therapeutically effective amount of at least one compound of Formula (I). Particularly, it is an embodiment of the invention to provide a method for treating, preventing or ameliorating a condition selected from cancer, diabetes, dyslipidemia, hypercholesterolemia, and associated symptoms or complications thereof in a subject in need thereof, comprising administering to said subject a therapeutically effective amount of (a) at least one compound of Formula (I); and (b) at least one additional agent selected from a retinoid receptor agonist, an anti-diabetic agent, a lipid lowering agent, an anti-thrombotic agent, and a blood pressure lowering agent, said co-administration being in any order. In one embodiment the additional agent is a RXR agonist.

Another embodiment of the invention is a method for inhibiting the onset of a RXR condition in a subject in need thereof, comprising administering to said subject a therapeutically effective amount of (a) at least one compound of Formula (I); and (b) at least one additional agent selected from a retinoid receptor agonist, an anti-diabetic agent, a lipid lowering agent, an anti-thrombotic agent, and a blood pressure lowering agent, said co-administration being in any order and the combined amounts providing the desired prophylactic effect. In one embodiment the additional agent is a RXR agonist.

It is a further embodiment of the invention to provide a process for making a pharmaceutical composition comprising admixing any of the compounds according to Formula (I) and a pharmaceutically acceptable carrier.

In the disclosed methods, the diabetes, dyslipidemia, hypercholesterolemia, and associated symptoms or complications thereof can be selected, for example, from IDDM, NIDDM, IGT (Impaired Glucose Tolerance), IFG (Impaired Fasting Glucose), Syndrome X (or Metabolic Syndrome), insulin resistance, obesity, hyperlipidemia (including, phase I hyperlipidemia, pre-clinical hyperlipidemia, and phase II hyperlipidemia), hypercholesteremia, hypertriglyceridemia, insulin resistance, dyslipidemia, nephropathy, neuropathy, retinopathy, atherosclerosis, low HDL, non-alcoholic steatohepatitis, polycystic ovary syndrome or polycystic ovarian syndrome, hypertension, ischemia, stroke, high blood pressure, heart disease (e.g., acute coronary syndromes or ACS, including but not limited to, non-ST segment myocardial infarction and ST-segment elevation myocardial infarctions), irritable bowel disorder, inflammation, cardiovascular disorders and cataracts.

Another aspect of the invention relates to treating hypertriglyceridemia, raising levels of HDL, lowering levels of LDL, and/or lowering total cholesterol.

Additional embodiments and advantages of the invention will become apparent from the detailed discussion, examples, and claims below.

DETAILED DESCRIPTION OF THE INVENTION

This invention relates to novel RXR agonists and compositions thereof for treatment or prophylaxis of conditions such as diabetes, dyslipidemia, and hypercholesterolemia, and associated symptoms or complications thereof.

One aspect of the present invention features a compound of Formula (I)

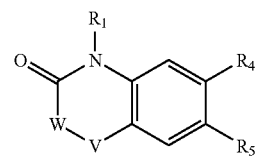

I wherein
$R_1$ is H or $C_{1-3}$alkyl;
W is —O—, —(O)—, or

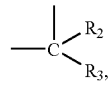

with the provisos that when W is —O— or —C(O)—, then V is not —O—, and when W is

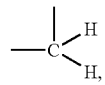

then V is not

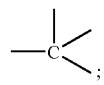

V is —O—, —N($R_2$)—, or

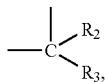

with the proviso that when V is —O—, W is not —O— or —(O)—, wherein $R_2$ and $R_3$ can be the same or different, each being independently selected from H and optionally substituted $C_{1-3}$alkyl;

$R_4$ is independently

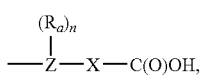

wherein
Z is selected from

X is selected from a bond, optionally substituted —O—$C_{1-5}$alkylene, and optionally substituted $C_{1-6}$alkylene; and $R_a$ is H or optionally substituted $C_{1-3}$alkoxy; and n is 1, 2, or 3;

or alternatively $R_4$ is H or optionally substituted $C_{1-3}$alkyl;

with the proviso that when $R_4$ is

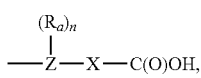

then $R_5$ cannot be

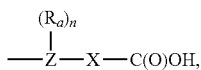

provided further that when $R_4$ is H or optionally substituted $C_{1-3}$alkyl, then $R_5$ cannot be H or optionally substituted $C_{1-3}$alkyl;

and $R_5$ is independently

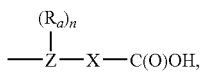

wherein
Z is selected from

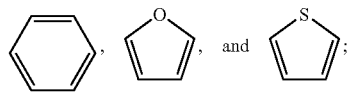

X is selected from a bond, optionally substituted —O—$C_{1-5}$alkylene, and optionally substituted $C_{1-6}$alkylene; and $R_a$ is H or optionally substituted $C_{1-3}$alkoxy; and n is 1, 2, or 3;

or alternatively $R_5$ is H or optionally substituted $C_{1-3}$alkyl;

with the proviso that when $R_5$ is

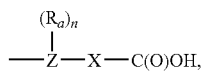

then $R_4$ cannot be

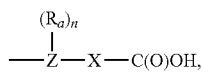

provided further that when $R_5$ is H or optionally substituted $C_{1-3}$alkyl, then $R_4$ cannot be H or optionally substituted $C_{1-3}$alkyl;

or an optical isomer, enantiomer, diastereomer, racemate, or pharmaceutically acceptable salt thereof.

Particularly, the present invention features a compound of Formula (I) wherein $R_1$ is H or $C_{1-3}$alkyl.

Particularly, the present invention features a compound of Formula (I) wherein $R_2$ and $R_3$ are independently selected from H and $C_{1-3}$alkyl.

Particularly, the present invention features a compound of Formula (I) wherein $R_4$ or $R_5$ is

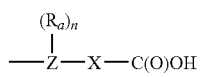

wherein Z is

More particularly, Z is

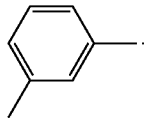

Particularly, the present invention features a compound of Formula (I) wherein $R_4$ or $R_5$ is

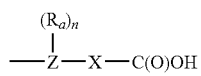

wherein Z is

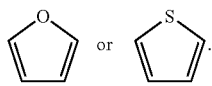

More particularly, Z is

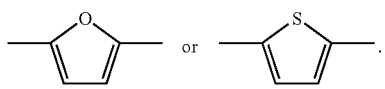

Particularly, the present invention features a compound of Formula (I) wherein $R_4$ or $R_5$ is

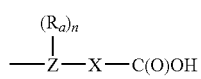

wherein X is a bond.

Particularly, the present invention features a compound of Formula (I) wherein $R_4$ or $R_5$ is

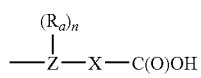

wherein X is optionally substituted —O—$C_{1-5}$alkylene. More particularly, the $C_{1-5}$alkylene is saturated. More particularly, the $C_{1-5}$alkylene is

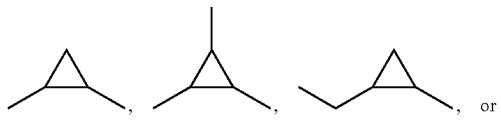

More particularly, 1, 2, or 3, of the hydrogen atoms in the $C_{1-5}$alkylene is further substituted with halo. More particularly, the halo is F.

Particularly, the present invention features a compound of Formula (I) wherein $R_4$ or $R_5$ is

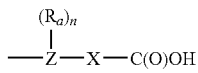

wherein X is optionally substituted $C_{1-6}$alkylene. More particularly, the $C_{1-6}$alkylene is saturated. More particularly, the $C_{1-6}$alkylene is

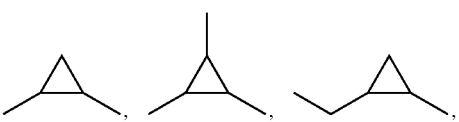

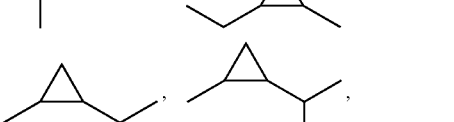

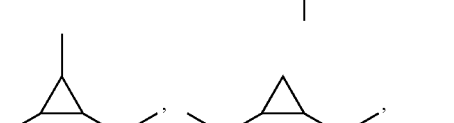

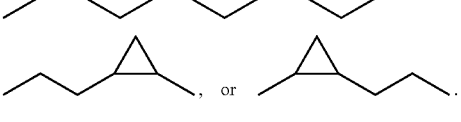

More particularly, 1, 2, or 3 of the hydrogen atoms in the $C_{1-6}$alkylene is further substituted with halo. More particularly, the halo is F.

Particularly, the present invention features a compound of Formula (I) wherein $R_4$ or $R_5$ is

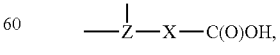

wherein X is optionally substituted —O—$C_{1-5}$alkylene or optionally substituted $C_{1-6}$alkylene, wherein the alkylene is unsaturated. More particularly, the alkylene contains a double or triple bond.

Particularly, the present invention features a compound of Formula (I) wherein $R_a$ is H.

Particularly, the present invention features a compound of Formula (I) wherein $R_a$ is —OCF$_3$, —OCH$_3$, —OCH$_2$CF$_3$, or —CH=CH—C(O)OH.

Particularly, the present invention features a compound of Formula (I) wherein
$R_1$ is —CH$_3$, —CH$_2$CH$_3$, or —CH(CH$_3$)$_2$;
$R_2$ and $R_3$ are independently selected from H, —CH$_3$, —CH$_2$CH$_3$, and —CH(CH$_3$)$_2$;
$R_4$ is

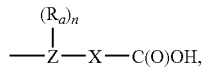

wherein

Z is

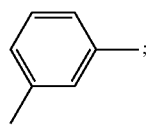

X is selected from

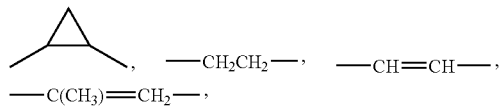

and —CH=C(CH$_3$)—; and
$R_a$ is —OCF$_3$ or —OCH$_2$CF$_3$; and
n is 1;
or alternatively $R_4$ is —CH$_3$;
with the proviso that when $R_4$ is

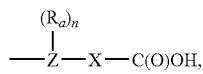

then $R_5$ cannot be

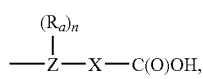

provided further that when $R_4$ is —CH$_3$, then $R_5$ cannot be —CH$_3$;
and $R_5$ is

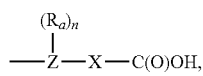

wherein
Z is

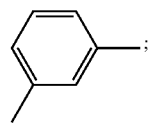

X is selected from

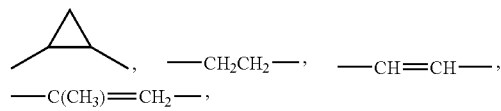

and —CH=C(CH$_3$)—; and $R_a$ is —OCF$_3$ or —OCH$_2$CF$_3$; and
n is 1;
or alternatively $R_5$ is —CH$_3$.

with the proviso that when $R_5$ is

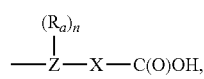

then $R_4$ cannot be

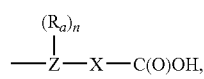

provided further that when $R_5$ is CH$_3$, then $R_4$ cannot be —CH$_3$.

Another aspect of the present invention features a pharmaceutical composition comprising at least one compound of Formula (I) and at least one pharmaceutically acceptable carrier. In another aspect of the invention, the pharmaceutical composition further comprises at least one additional agent, drug, medicament, antibody and/or inhibitor for treating, ameliorating and/or preventing a RXR mediated disease. In one embodiment, at least one compound of Formula (I) is selected from

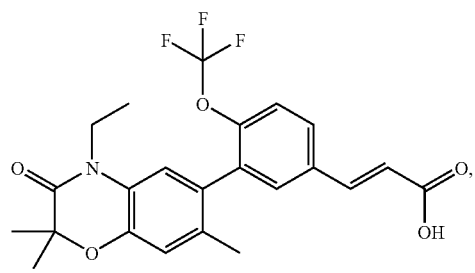

-continued

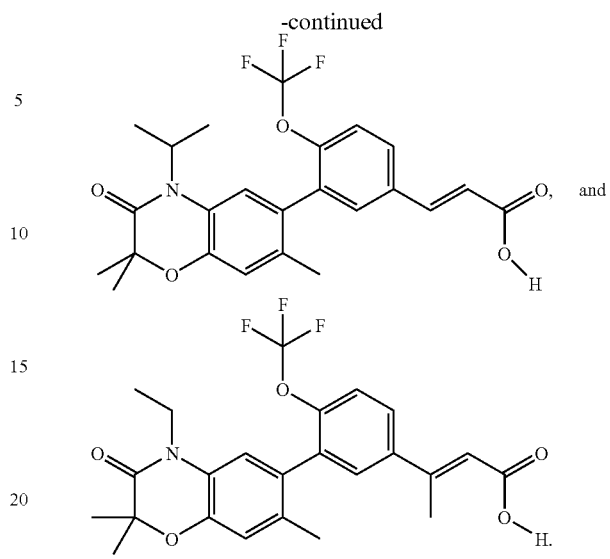

In another embodiment, at least one compound of Formula (I) is selected from

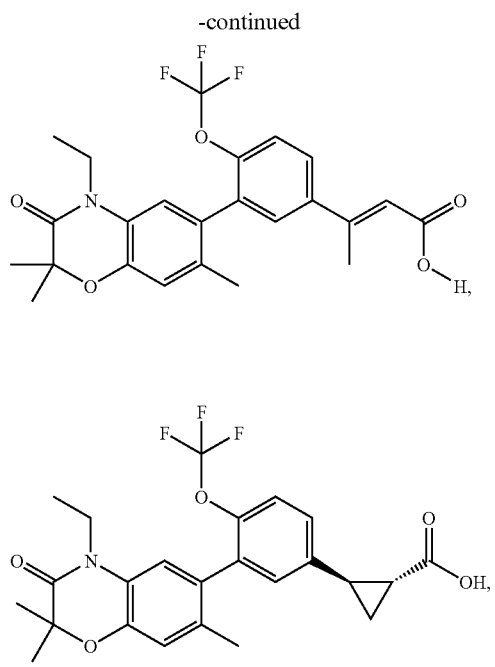

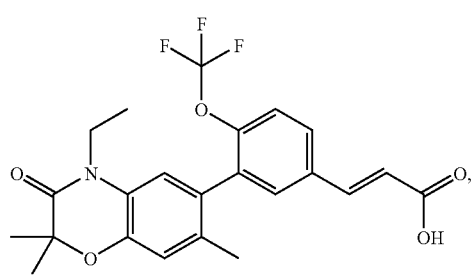

In another embodiment of the invention a method is disclosed for treating, preventing or ameliorating a RXR mediated condition in a subject in need thereof comprising administering to the subject a therapeutically effective amount of at least one compound of Formula (I). An embodiment of the invention includes a method for treating, preventing or ameliorating a RXR mediated condition selected from cancer, diabetes, dyslipidemia, hypercholesterolemia, and associated symptoms or complications thereof in a subject in need thereof, comprising administering to said subject a therapeutically effective amount of at least one compound of Formula (I).

A further embodiment of the invention is a method for treating, preventing or ameliorating a RXR mediated condition selected from IDDM, NIDDM, IGT, IFG, Syndrome X (or Metabolic Syndrome), insulin resistance, obesity, hyperlipidemia (including, phase I hyperlipidemia, pre-clinical hyperlipidemia, and phase II hyperlipidemia), hypercholesteremia, hypertriglyceridemia, insulin resistance, dyslipidemia, nephropathy, neuropathy, retinopathy, atherosclerosis, low HDL, non-alcoholic steatohepatitis, polycystic ovary syndrome or polycystic ovarian syndrome, hypertension, ischemia, stroke, high blood pressure, heart disease (erg., acute coronary syndromes or ACS, including but not limited to, non-ST segment myocardial infarction and ST-segment elevation myocardial infarctions), irritable bowel disorder, inflammation, cardiovascular disorders and cataracts in a subject in need thereof, comprising administering to said subject a therapeutically effective amount of at least one compound of Formula (I).

One embodiment of the invention is a method of treating hypertriglyceridemia, raising levels of HDL, lowering levels of LDL, and/or lowering total cholesterol.

Furthermore, RXR agonists can be co-administered with a second agent other than a retinoid receptor agonist; such second agent can be, for example, an anti-diabetic agent, a lipid lowering agent, a blood pressure lowering agent, and an anti-thrombotic agent (e.g., aspirin, heparins, glycoprotein IIb-IIIa inhibitors, or Factor Xa inhibitors).

Particularly, it is an embodiment of the invention to provide a method for treating, preventing or ameliorating a condition selected from cancer, diabetes, dyslipidemia, hypercholesterolemia, and associated symptoms or complications thereof in a subject in need thereof, comprising administering to said subject a therapeutically effective amount of (a) at least one compound of Formula (I); and (b) at least one aditional agent selected from a retinoid receptor agonist, an anti-diabetic agent, a lipid lowering agent, an anti-thrombotic agent, and a blood pressure lowering agent, said administration being in any order. In one embodiment, the additional agent is a second RXR agonist. In a further embodiment, the additional agent is an anti-diabetic agent. In another embodiment, the additional agent is a lipid lowering agent. In still another embodiment, the additional agent is an anti-thrombotic agent. In yet another embodiment, the additional agent is a blood pressure lowering agent. In another emobodiment, the aditional agent is a RAR agonist.

Another embodiment of the invention is a method for inhibiting the onset of a RXR condition in a subject in need thereof, comprising administering to said subject a therapeutically effective amount of at least one compound of Formula (I). Another embodiment of the invention is a method for inhibiting the onset of a condition selected from cancer, diabetes, dyslipidemia, hypercholesterolemia, and associated symptoms or complications thereof in a subject in need thereof, comprising administering to said subject a therapeutically effective amount of (a) at least one compound of Formula (I); and (b) at least one compound selected from the group consisting of a retinoid receptor agonist, an anti-diabetic agent, a lipid lowering agent, an anti-thrombotic agent, and a blood pressure lowering agent, said co-administration being in any order and the combined amounts providing the desired prophylactic effect.

A further embodiment of the invention is a method for inhibiting the onset of a RXR condition selected from IDDM, NIDDM, IGT, IFG, Syndrome X (or Metabolic Syndrome), insulin resistance, obesity, hyperlipidemia (including, phase I hyperlipidemia, pre-clinical hyperlipidemia, and phase II hyperlipidemia), hypercholesteremia, hypertriglyceridemia, insulin resistance, dyslipidemia, nephropathy, neuropathy, retinopathy, atherosclerosis, low HDL, non-alcoholic steatohepatitis, polycystic ovary syndrome or polycystic ovarian syndrome, hypertension, ischemia, stroke, high blood pressure, heart disease (e.g., acute coronary syndromes or ACS, including but not limited to, non-ST segment myocardial infarction and ST-segment elevation myocardial infarctions), irritable bowel disorder, inflammation, cardiovascular disorders and cataracts in a subject in need thereof, comprising administering to said subject a therapeutically effective amount of at least one compound of Formula (I). In one embodiment, the additional agent is a second RXR agonist. In a further embodiment, the additional agent is an anti-diabetic agent. In another embodiment, the additional agent is a lipid lowering agent. In still another embodiment, the additional agent is an anti-thrombotic agent. In yet another embodiment, the additional agent is a blood pressure lowering agent. In another emobodiment, the additional agent is a RAR agonist.

It is a further embodiment of the invention to provide a process for making a pharmaceutical composition comprising admixing any of the compounds according to Formula (I) and a pharmaceutically acceptable carrier.

In a further embodiment of the invention, a method for treating, preventing or ameliorating a RXR mediated condition in a subject in need thereof comprising administering to the subject a therapeutically effective amount of at least one compound of Formula (I), wherein the therapeutically effective amount of the compound of Formula (I) is from about 0.001 mg/kg/day to about 5 mg/kg/day.

In a further embodiment of the invention, a method for inhibiting the onset of a RXR mediated condition in a subject in need thereof comprising administering to the subject a therapeutically effective amount of at least one compound of Formula (I), wherein the therapeutically effective amount of the compound of Formula (I) is from about 0.001 mg/kg/day to about 5 mg/kg/day.

The invention is further described below.

A) Terms

Some terms are defined below and by their usage throughout this disclosure.

Unless otherwise noted, "alkyl" as used herein, whether used alone or as part of a substituent group, includes straight, cyclic, and branched-chain alkyl having 1 to 6 carbon atoms, or any number within this range. For example, alkyl radicals include methyl, ethyl, n-propyl, isopropyl, n-butyl, isobutyl, sec-butyl, t-butyl, 2-butenyl, 2-butynyl, n-pentyl, 3-(2-methyl)butyl, 2-pentyl, 2-methylbutyl, neopentyl, n-hexyl, 2-hexyl and 2-methylpentyl. "Alkoxy" radicals are oxygen ethers formed from the previously described straight, branched, or cyclic chain alkyl groups.

The term "alkylene" denotes straight, branched, or cyclic alkyl, or straight or branched alkenyl, or straight or branched alkynyl, optionally substituted with one to five, preferably one to three groups including, but not limited to, optionally substituted $C_{1-3}$alkyl and F.

The term "oxo" whether used alone or as part of a substituent group refers to an O= to either a carbon or a sulfur atom. For example, phthalimide and saccharin are examples of compounds with oxo substituents.

The term "substituted" refers to a radical in which one or more hydrogen atoms are each independently replaced with the same or different substituent(s). Preferred substituents include hydroxy, halogen, oxo, amino, carboxyl, and alkoxy.

With reference to substituents, the term "independently" means that when more than one of such substituent is possible, such substituents may be the same or different from each other.

The term "composition" is intended to encompass a product comprising the specified ingredients in the specified amounts, as well as any product which results, directly or indirectly, from combinations of the specified ingredients in the specified amounts.

The term "subject" as used herein, refers to an animal, preferably a mammal, most preferably a human, who is the object of treatment, observation or experiment.

The term "RXR" as used herein refers to Retinoid-X Receptors.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Diabetes and associated symptoms or complications include such conditions as IDDM, NIDDM, Syndrome X, IGT (Impaired Glucose Tolerance), IFG (Impaired Fasting Glucose), obesity, nephropathy, neuropathy, retinopathy, atherosclerosis, polycystic ovary syndrome, polycystic ovarian syndrome, hypertension, ischemia, stroke, heart disease, irritable bowel disorder, inflammation, and cataracts. IGT and IFG are also known as "prediabetic state."

Methods are known in the art for determining effective doses for therapeutic and prophylactic purposes for the disclosed pharmaceutical compositions or the disclosed drug combinations, whether or not formulated in the same composition. For therapeutic purposes, the term "therapeutically effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "therapeutically effective amount" refers to that amount of each active compound or pharmaceutical agent, alone or in combination, that treats or inhibits in a subject the onset or progression of a disorder as being sought by a researcher, veterinarian, medical doctor or other clinician. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both (or more) drugs are administered in an amount that is sub-therapeutic or sub-prophylactic if administered alone, but are therapeutic or prophylactic when administered together.

The term "protecting groups" refer to those moieties known in the art that are used to mask functional groups; protecting groups may be removed during subsequent synthetic transformations or by metabolic or other in vivo administration conditions. During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, Third Edition, John Wiley & Sons, 1999. The protecting groups may be removed at a convenient subsequent stage using methods known in the art. Examples of hydroxyl and diol protecting groups are provided below.

Protection for the hydroxyl group includes methyl ethers, substituted methyl ethers, substituted ethyl ethers, substitute benzyl ethers, and silyl ethers.

Substituted Methyl Ethers

Examples of substituted methyl ethers include methyoxymethyl, methylthiomethyl, t-butylthiomethyl, (phenyldimethylsilyl)methoxymethyl, benzyloxymethyl, p-methoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl)ethoxymethyl, Tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxido, 1-[(2-chloro-4-methyl)phenyl]-4-methoxypiperidin-4-yl, 1,4-dioxan-2-yl, tetrahydrofuranyl, tetrahydrothiofuranyl and 2,3,3a,4,5,6,7,7a-octahydro-7,8,8-trimethyl-4,7-methanobenzofuran-2-yl.

Substituted Ethyl Ethers

Examples of substituted ethyl ethers include 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, and polyethyleneglycol ethers.

Substituted Benzyl Ethers

Examples of substituted benzyl ethers include pmethoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p,p'-dinitrobenzhydryl, 5-dibenzosuberyl, triphenylmethyl, α-naphthyidiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-ylmethyl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, and benzisothiazolyl S,S-dioxido.

Silyl Ethers

Examples of silyl ethers include trimethylsilyl, triethylsilyi, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, and t-butylmethoxyphenylsilyl Esters In addition to ethers, a hydroxyl group may be protected as an ester. Examples of esters include formate, benzoylformate, acetate, chloroacetate, dichiloroacetate, trichloroacetate, trifluoroacetate, methoxyacetate, triphenylmethoxyacetate, phenoxyacetate, pchlorophenoxyacetate, p-P-phenylacetate, 3-phenylpropionate, 4-oxopentanoate(levulinate), 4,4-(ethylenedithio)pentanoate, pivaloate, adamantoate, crotonate, 4-methoxycrotonate, benzoate, p-phenylbenzoate, 2,4,6-trimethylbenzoate(mesitoate), and polyethyleneglycol esters.

Carbonates

Examples of carbonates include methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, methyl dithiocarbonate, and polyethyleneglycol carbonates.

Assisted Cleavage

Examples of assisted cleavage include 2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, and 2-(methylthiomethoxymethyl)benzoate.

Miscellaneous Esters

Examples of miscellaneous esters include 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate(tigloate), o-(methoxycarbonyl) benzoate, p-P-benzoate, α-naphthoate, nitrate, alkyl N,N,N', N'-tetramethylphosphorodiamidate, N-phenylcarbamate, borate, dimethylphosphinothioyl, and 2,4-dinitrophenytsulfenate

Sulfonates

Examples of sulfonates include sulfate, methanesulfonate (mesylate), benzylsulfonate, and tosylate.

Protection for 1,2- and 1,3-diols

Cyclic Acetals and Ketals

Examples of cyclic acetals and ketals include methylene, ethylidene, 1-t-butylethylidene, 1-phenylethylidene, (4-methoxyphenyl)ethylidene, 2,2,2-trichloroethylidene, acetonide (isopropylidene), cyclopentylidene, cyclohexylidene, cycloheptylidene, benzylidene, pmethoxybenzylidene, 2,4-dimethoxybenzylidene, 3,4-dimethoxybenzylidene, and 2-nitrobenzylidene.

Cyclic Ortho Esters

Examples of cyclic ortho esters include methoxymethylene, ethoxymethylene, dimethoxymethylene, 1-methoxyethylidene, 1-ethoxyethylidine, 1,2-dimethoxyethylidene, α-methoxybenzylidene, 1-(N,N-dimethylamino)ethylidene derivative, α(N,N-dimethylamino)benzylidene derivative, and 2-oxacyclopentylidene.

Silyl Derivatives

Examples of silyl derivatives include di- t-butylsilylene group, and 1,3-(1,1,3,3-tetraisopropyidisiloxanylidene)derivative.

B) Compounds

| STRUCTURE | COMPOUND # | NAME |
|---|---|---|
| 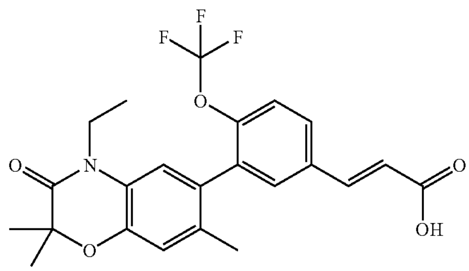 | 1 | 3-[3-(4-Ethyl-2,2,7-trimethyl-3-oxo-3,4-dihydro-2H-benzo[1,4]oxazin-6-yl)-4-trifluoromethoxy-phenyl]-acrylic acid |
| 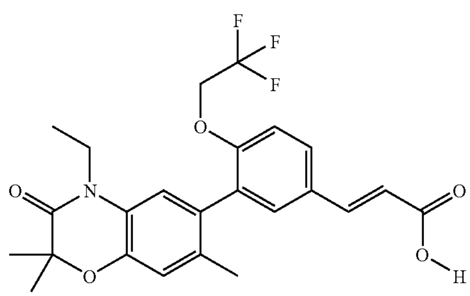 | 2 | 3-[3-(4-Ethyl-2,2,7-trimethyl-3-oxo-3,4-dihydro-2H-benzo[1,4]oxazin-6-yl)-4-(2,2,2-trifluoro-ethoxy)-phenyl]-acrylic acid |
| 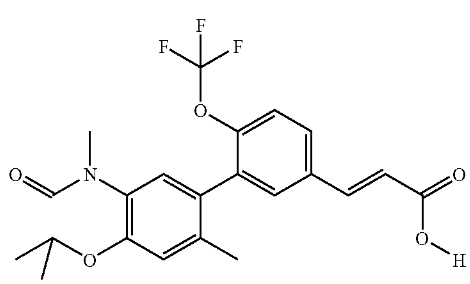 | 3 | 3-[3-(2,2,4,7-Tetramethyl-3-oxo-3,4-dihydro-2H-benzo[1,4]oxazin-6-yl)-4-trifluoromethoxy-phenyl]-acrylic acid |
| 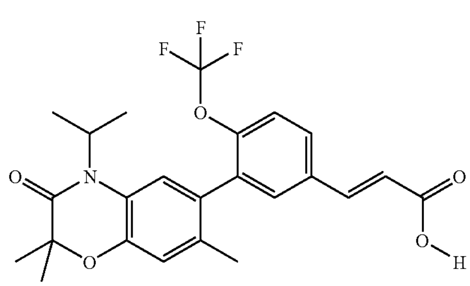 | 4 | 3-[3-(4-Isopropyl-2,2,7-trimethyl-3-oxo-3,4-dihydro-2H-benzo[1,4]oxazin-6-yl)-4-trifluoromethoxy-phenyl]-acrylic acid |

-continued

B) Compounds

| STRUCTURE | COMPOUND # | NAME |
|---|---|---|
| 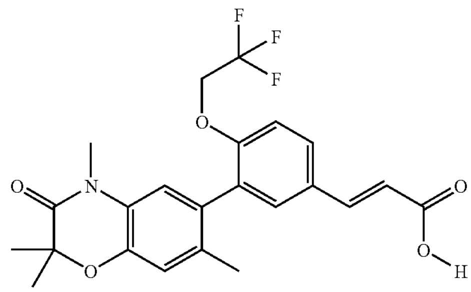 | 5 | 3-[3-(2,2,4,7-Tetramethyl-3-oxo-3,4-dihydro-2H-benzo[1,4]oxazin-6-yl)-4-(2,2,2-trifluoro-ethoxy)-phenyl]-acrylic acid |
| 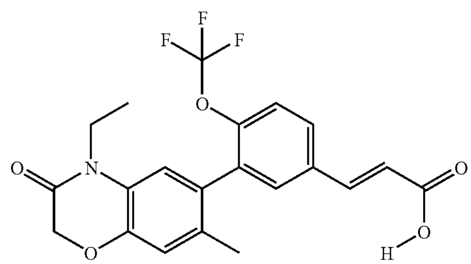 | 6 | 3-[3-(4-Ethyl-7-methyl-3-oxo-3,4-dihydro-2H-benzo[1,4]oxazin-6-yl)-4-trifluoromethoxy-phenyl]-acrylic acid |
| 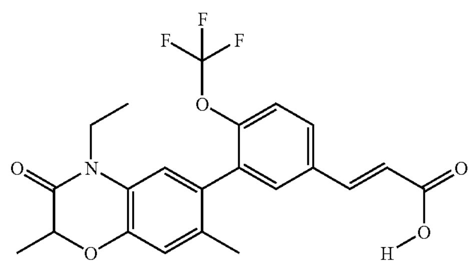 | 7 | 3-[3-(4-Ethyl-2,7-dimethyl-3-oxo-3,4-dihydro-2H-benzo[1,4]oxazin-6-yl)-4-trifluoromethoxy-phenyl]-acrylic acid |
| 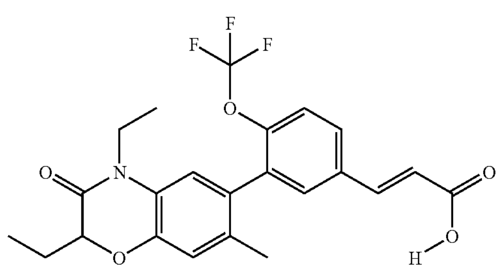 | 8 | 3-[3-(2,4-Diethyl-7-methyl-3-oxo-3,4-dihydro-2H-benzo[1,4]oxazin-6-yl)-4-trifluoromethoxy-phenyl]-acrylic acid |
| 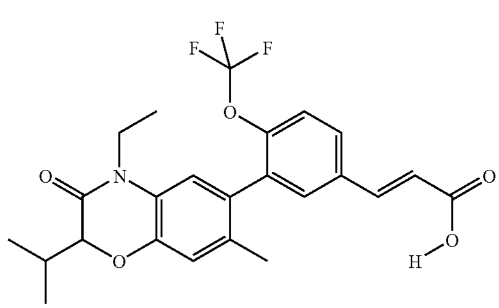 | 9 | 3-[3-(4-Ethyl-2-isopropyl-7-methyl-3-oxo-3,4-dihydro-2H-benzo[1,4]oxazin-6-yl)-4-trifluoromethoxy-phenyl]-acrylic acid |

-continued

B) Compounds

| STRUCTURE | COMPOUND # | NAME |
|---|---|---|
| 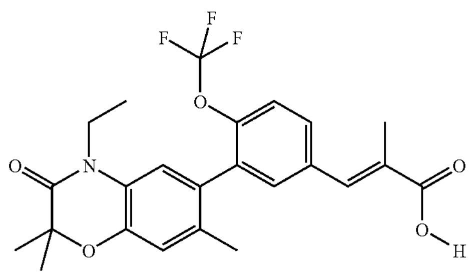 | 10 | 3-[3-(4-Ethyl-2,2,7-trimethyl-3-oxo-3,4-dihydro-2H-benzo[1,4]oxazin-6-yl)-4-trifluoromethoxy-phenyl]-2-methyl-acrylic acid |
| 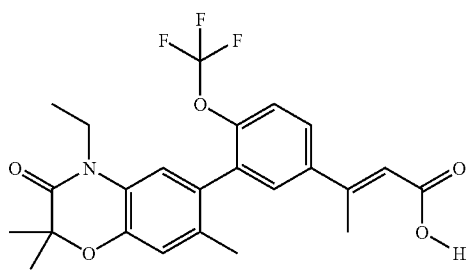 | 11 | 3-[3-(4-Ethyl-2,2,7-trimethyl-3-oxo-3,4-dihydro-2H-benzo[1,4]oxazin-6-yl)-4-trifluoromethoxy-phenyl]-but-2-enoic acid |
| 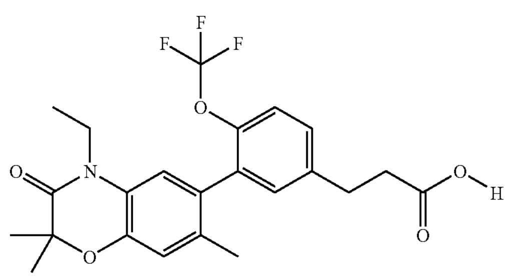 | 12 | 3-[3-(4-Ethyl-2,2,7-trimethyl-3-oxo-3,4-dihydro-2H-benzo[1,4]oxazin-6-yl)-4-trifluoromethoxy-phenyl]-propionic acid |
| 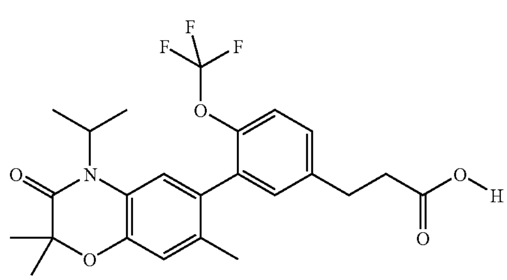 | 13 | 3-[3-(4-Isopropyl-2,2,7-trimethyl-3-oxo-3,4-dihydro-2H-benzo[1,4]oxazin-6-yl)-4-trifluoromethoxy-phenyl]-propionic acid |
| 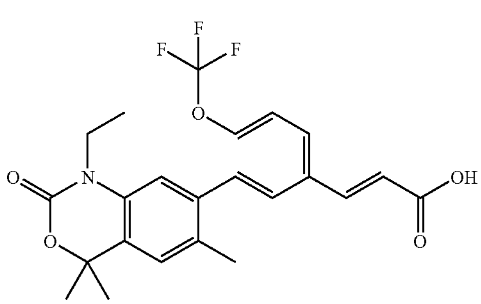 | 14 | 3-[3-(1-Ethyl-4,4,6-trimethyl-2-oxo-1,4-dihydro-2H-benzo[d][1,3]oxazin-7-yl)-4-trifluoromethoxy-phenyl]-acrylic acid |

-continued

B) Compounds

| STRUCTURE | COMPOUND # | NAME |
|---|---|---|
| 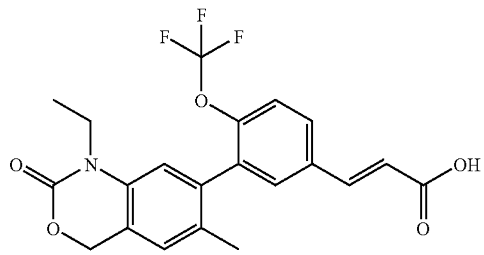 | 15 | 3-[3-(1-Ethyl-6-methyl-2-oxo-1,4-dihydro-2H-benzo[d][1,3]oxazin-7-yl)-4-trifluoromethoxy-phenyl]-acrylic acid |
| 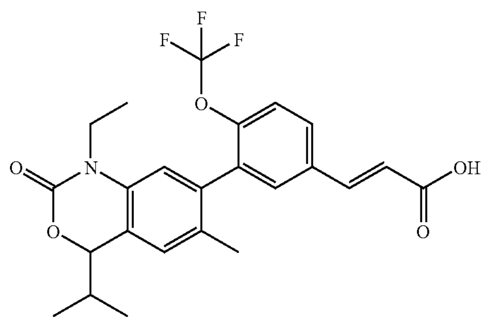 | 16 | 3-[3-(1-Ethyl-4-isopropyl-6-methyl-2-oxo-1,4-dihydro-2H-benzo[d][1,3]oxazin-7-yl)-4-trifluoromethoxy-phenyl]-acrylic acid |
| 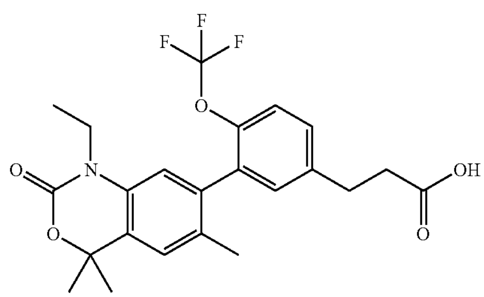 | 17 | 3-[3-(1-Ethyl-4,4,6-trimethyl-2-oxo-1,4-dihydro-2H-benzo[d][1,3]oxazin-7-yl)-4-trifluoromethoxy-phenyl]-propionic acid |
| 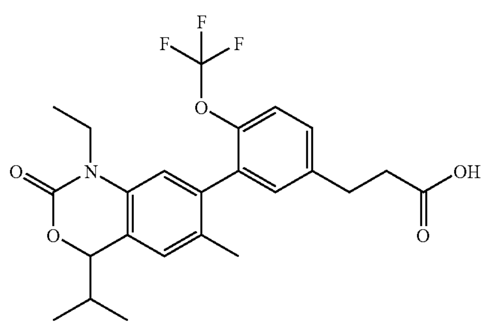 | 18 | 3-[3-(1-Ethyl-4-isopropyl-6-methyl-2-oxo-1,4-dihydro-2H-benzo[d][1,3]oxazin-7-yl)-4-trifluoromethoxy-phenyl]-propionic acid |
| 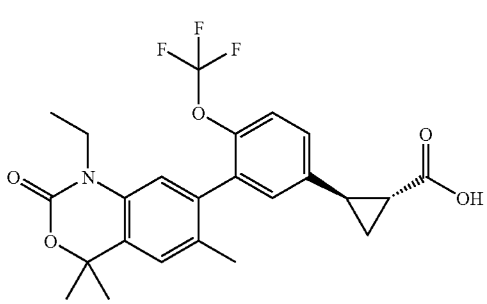 | 19 | 2-[3-(1-Ethyl-4,4,6-trimethyl-2-oxo-1,4-dihydro-2H-benzo[d][1,3]oxazin-7-yl)-4-trifluoromethoxy-phenyl]-cyclopropanecarboxylic acid |

-continued

B) Compounds

| STRUCTURE | COMPOUND # | NAME |
|---|---|---|
| 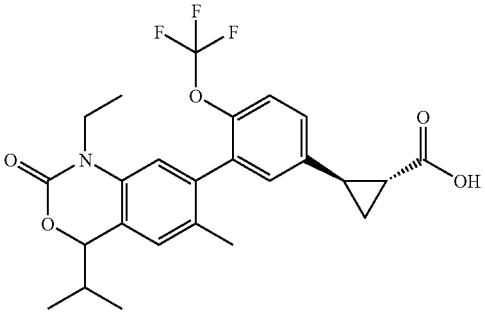 | 20 | 2-[3-(1-Ethyl-4-isopropyl-6-methyl-2-oxo-1,4-dihydro-2H-benzo[d][1,3]oxazin-7-yl)-4-trifluoromethoxy-phenyl]-cyclopropanecarboxylic acid |
| 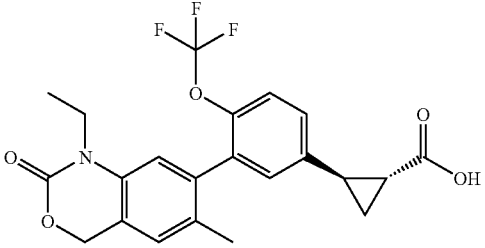 | 21 | 2-[3-(1-Ethyl-6-methyl-2-oxo-1,4-dihydro-2H-benzo[d][1,3]oxazin-7-yl)-4-trifluoromethoxy-phenyl]-cyclopropanecarboxylic acid |
| 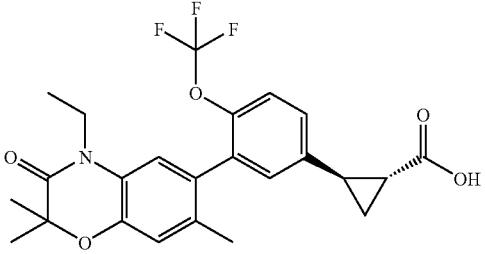 | 22 | 2-[3-(4-Ethyl-2,2,7-trimethyl-3-oxo-3,4-dihydro-2H-benzo[1,4]oxazin-6-yl)-4-trifluoromethoxy-phenyl]-cyclopropanecarboxylic acid |
| 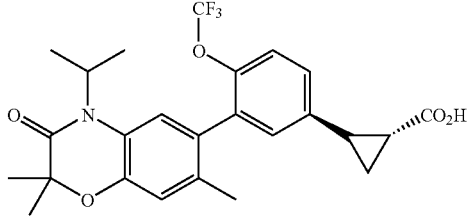 | 23 | 2-[3-(4-Isopropyl-2,2,7-trimethyl-3-oxo-3,4-dihydro-2H-benzo[1,4]oxazin-6-yl)-4-trifluoromethoxy-phenyl]-cyclopropanecarboxylic acid |
| 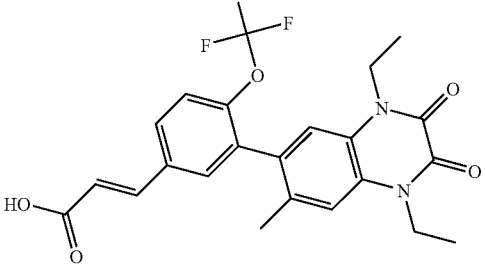 | 24 | 3-[3-(1,4-Diethyl-7-methyl-2,3-dioxo-1,2,3,4-tetrahydro-quinoxalin-6-yl)-4-trifluoromethoxy-phenyl]-acrylic acid |

-continued

B) Compounds

| STRUCTURE | COMPOUND # | NAME |
|---|---|---|
| 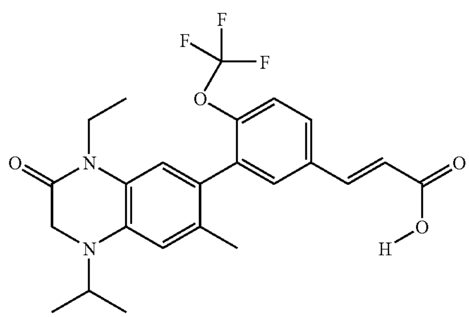 | 25 | 3-[3-(4-Ethyl-1-isopropyl-7-methyl-3-oxo-1,2,3,4-tetrahydro-quinoxalin-6-yl)-4-trifluoromethoxy-phenyl]-acrylic acid |
| 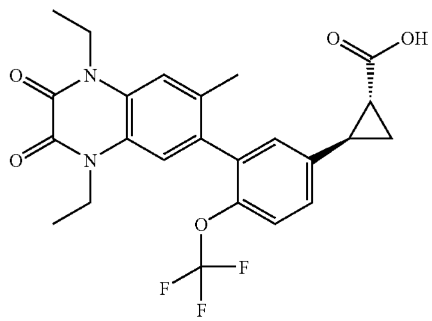 | 26 | 2-[3-(1,4-Diethyl-7-methyl-2,3-dioxo-1,2,3,4-tetrahydro-quinoxalin-6-yl)-4-trifluoromethoxy-phenyl]-cyclopropanecarboxylic acid |
| 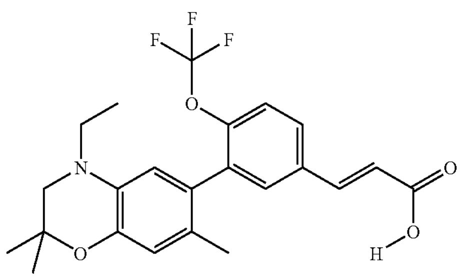 | 27 | 2-Propenoic acid, 3-[3-(4-ethyl-3,4-dihydro-2,2,7-trimethyl-2H-1,4-benzoxazin-6-yl)-4-(trifluoromethoxy)phenyl]-, (2E)- |

C) Synthesis

The invention provides methods of making the disclosed compounds according to traditional organic synthetic methods as well as matrix or combinatorial synthetic methods. Schemes 1 through 12 describe suggested synthetic routes. Using these Schemes, the guidelines below, and the examples, a person of skill in the art may develop analogous or similar methods for a given compound that is within the invention. These methods are representative of the synthetic schemes, but are not to be construed as limiting the scope of the invention.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "*Design of Prodrugs*", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. Where the processes for the preparation of the compounds according to the invention give rise to mixtures of stereoisomers, these isomers may be separated by conventional techniques such as preparative chromatography. The compounds may be prepared in racemic form or as individual enantiomers or diasteromers by either stereospecific synthesis or by resolution.

The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers and enantiomers thereof are encompassed within the scope of the present invention.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Examples of the described synthetic routes include Examples 1 through 27 and Schemes 1-9. Compounds analogous to the target compounds of these examples can be made according to similar routes. The disclosed compounds are useful as pharmaceutical agents as described in the next section.

Abbreviations or acronyms useful herein include:

Boc (tert butyl carbamate)

BuLi (butyllithium)

DMAP (4-(dimethylamino)pyridine)

DMF (dimethylformamide)

DMPU (1,3-Dimethyl-3,4,5,6-tetrahydro-2(1H)-pyrimidinone)

DMSO (methyl sulfoxide)

EDCI (1-(3-Dimethylaminopropyl)-3-ethylcarbodiimide hydrochloride)

EtOAc (ethyl acetate)

LCMS (high pressure liquid chroatography with mass spectrometer)

LHMDS (lithium hexamethyl disilazide)

NaHMDS (sodium hexamethyl disilazide)

NaO$^t$Bu (sodium tert-butoxide)

NBS (N-Bromosuccinimide)

NMP (N-Methyl Pyrroidinone)

TEMPO (2,2,6,6-tetramethyl-1-piperdinyloxy, free radical)

TFA (trifluoroacetic acid);

SPE (solid phase extraction)

THF (tetrahydrofuran)

TLC (thin layer chromatography)

General Guidance

Scheme 1a

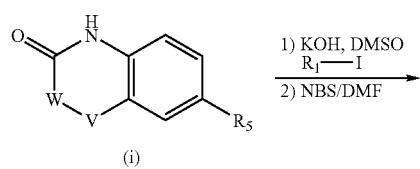

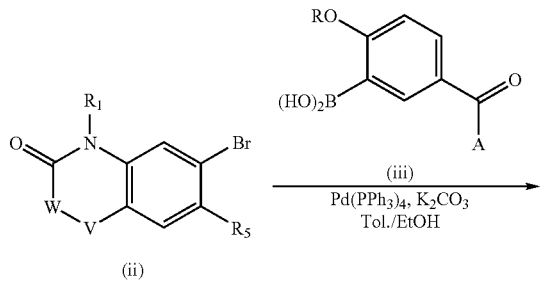

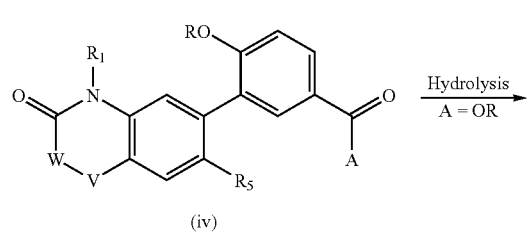

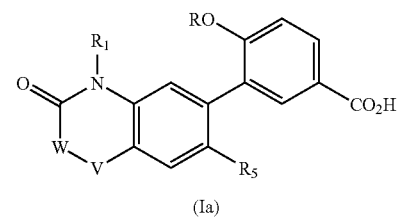

As demonstrated in Scheme 1a above, wherein A represents H, $C_{1-6}$alkyl, aryl, or $C_{1-6}$alkoxy, and R represents $C_{1-6}$alkyl, and $R_5$ represents H or optionally substituted $C_{1-3}$alkyl, and W, V, and $R_1$ are as described hereinabove, the aniline nitrogen of (i) can be treated with an alkyl iodide followed by bromination and the resultant aryl bromide (ii) can undergo a Suzuki reaction with an aryl boronic acid (iii) containing a carbonyl functionality to yield intermediate (iv). The intermediate (iv) where A is $C_{1-6}$alkoxy can be directly hydrolyzed to give benzoic acid derivatives of Formula (Ia).

Scheme 1b below, wherein A represents H, $C_{1-6}$alkyl, or aryl, and $R_x$ and $R_y$ represent straight or branched $C_{1-4}$alkyl, and $A_1$, $A_2$, and $A_3$ independently represent H, straight or branched $C_{1-4}$alkyl optionally substituted by halo, or halo, and W, V, and $R_1$ are as described hereinabove, shows the intermediate (iv) can be treated with a Wadsworth-Emmon's reagent (modified Witting reagent) to yield substituted phenylacrylic esters or phenyldienoic esters, either of which can be hydrolyzed to the corresponding substituted acids (Ib and Ic) under either acidic or basic conditions.

Scheme 1b

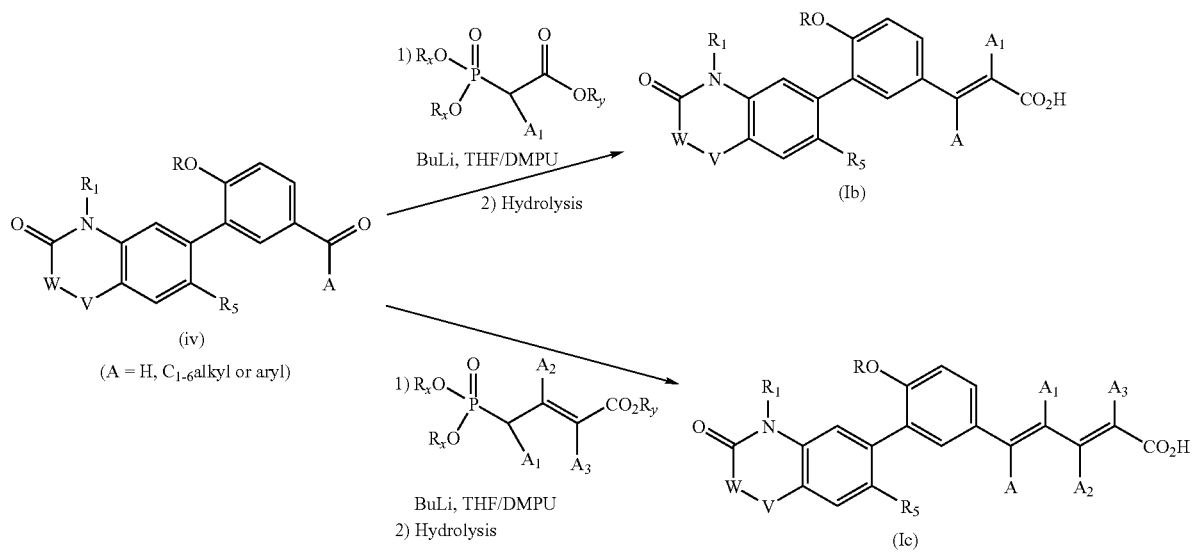

Scheme 2

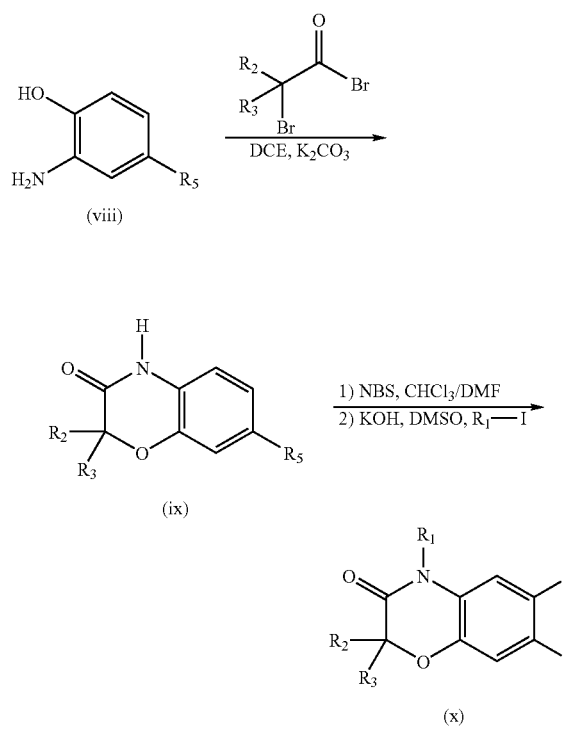

Scheme 3

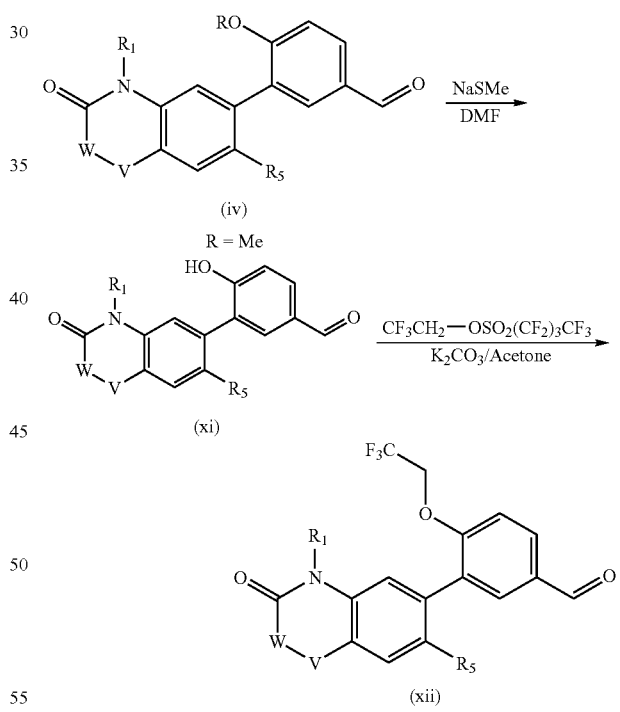

In accordance with Scheme 2 wherein $R_1$, $R_2$, $R_3$, and $R_5$ are as described hereinabove, a substituted 2-amino phenol (viii) can be converted into a substituted 4H-benzo[1,4]oxazin-3-one (ix) by treatment with α-bromoacetyl bromide. The 4H-benzo[1,4]oxazin-3-one can be brominated by reaction with bromine and the amide nitrogen can be alkylated by a reaction with an alkyl iodide to yield intermediate (x). This intermediate can be used as the aryl bromide component (ii) in the synthetic sequence demonstrated in Scheme 1a.

In some cases where a 2,2,2-trifluoroethoxy group is desired at the phenolic R position of the intermediate (v) as shown in Scheme 1, a sequence similar to the one shown in Scheme 3 wherein $R_1$, W, V, and $R_5$ are as described hereinabove can be used when intermediate (iv) has R=Me functionality. The methoxy group is converted into a phenol (xi) by treatment with boron sodium thioethoxide in DMF. The intermediate (xi) is then reacted with 2,2,2-trifluoroethyl-nonafluorosulfonate in the presence of a base such as potassium carbonate to yield the desired product (xii) which can

Scheme 4

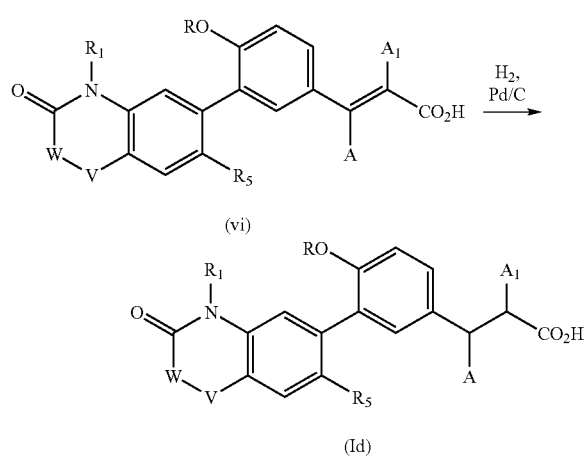

As shown in Scheme 4 wherein A, $A_1$, $R_1$, W, V, and $R_5$ are as described hereinabove, the double bonds of the phenylacrylic acids and phenyl dienoic acids, such as (Ib) and (Ic) synthesized by a sequence similar to the one shown in Schemes 1-3 can be reduced by hydrogenation with metal catalysts such as palladium on carbon to give corresponding carboxylic acids (Id). The same acids can also be synthesized from the acrylic esters by hydrogenation followed by hydrolysis of the ester functionality.

Scheme 5

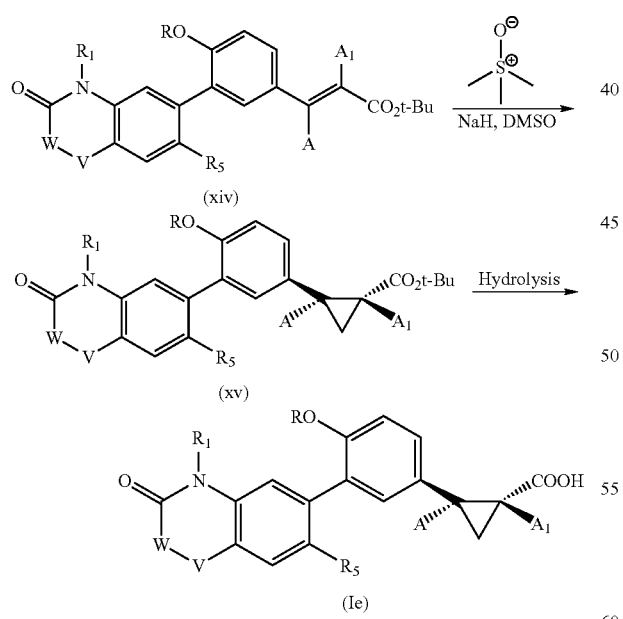

In accordance with Scheme 5 wherein A represents H, $C_{1-6}$alkyl, aryl, or alkoxy, $A_1$ represents H, $CH_3$ optionally substituted by halo, or halo, and R represents $C_{1-6}$alkyl, and W, V, $R_1$ and $R_5$ are as described hereinabove, the cyclopropyl carboxylic acid (xvi) can be synthesized by a 1,4-addition of the ylide generated from trimethylsulfoxonium iodide and sodium hydride into the phenylacrylate ester (xiv). The cyclopropyl ester (xv) is then hydrolyzed to give the corresponding carboxylic acid (Ie). Several other methods have been reported for the conversion of an acrylate ester into a cyclopropyl carboxylate ester such as the reaction of (xiv) with diazomethane in the presence of a Palladium or Copper catalyst. See, for example, Denmark et al., Cyclopropanation with Diazomethane and Bis(oxazoline)palladium(II) Complexes, Journal of Organic Chemistry (1997), 62(10), 3375-3389; Charette et al., Bis(oxazoline)-copper(I)-catalyzed enantioselective cyclopropanation of cinnamate esters with diazomethane, Tetrahedron. Asymmetry (2003), 14(7), 867-872; Eilbracht et al., Tandem silylformylation/Wittig olefination of terminal alkynes: stereoselective synthesis of 2,4-Dienoic esters, European Journal of Organic Chemistry (2000), (7), 1131-1135.

Scheme 6

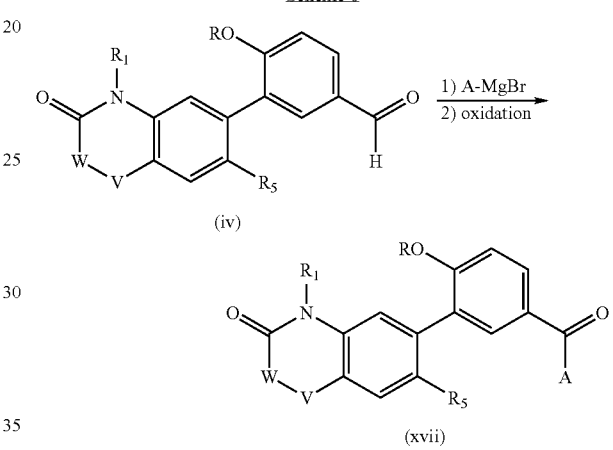

In accordance with Scheme 6 wherein A, R, $R_1$, W, V, and $R_5$ are as described in Scheme 1, the benzaldehyde (iv) can be converted into a corresponding ketone (xvii) by addition of an alkyl or aryl Grignard reagent or an alkyl or aryllithium reagent into the aldehyde followed by oxidation of the corresponding secondary alcohol.

Scheme 7

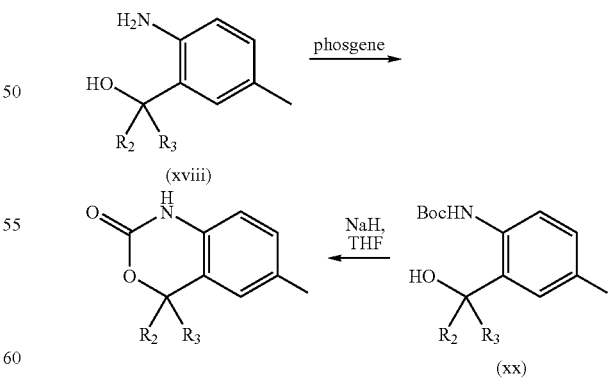

In accordance with Scheme 7 wherein $R_2$ and $R_3$ are as described hereinabove, the amino alcohols of the formula (xviii) can be converted into a corresponding 1,4-dihydro-benzo[d][1,3]oxazin-2-one (xix) by treatment with phosgene, trichlorophosgene or CDI. The 1,4-dihydro-benzo[d]

[1,3]oxazin-2-one (xix) can also be prepared by the base induced cyclization of the Boc-protected amino alcohol (xx).

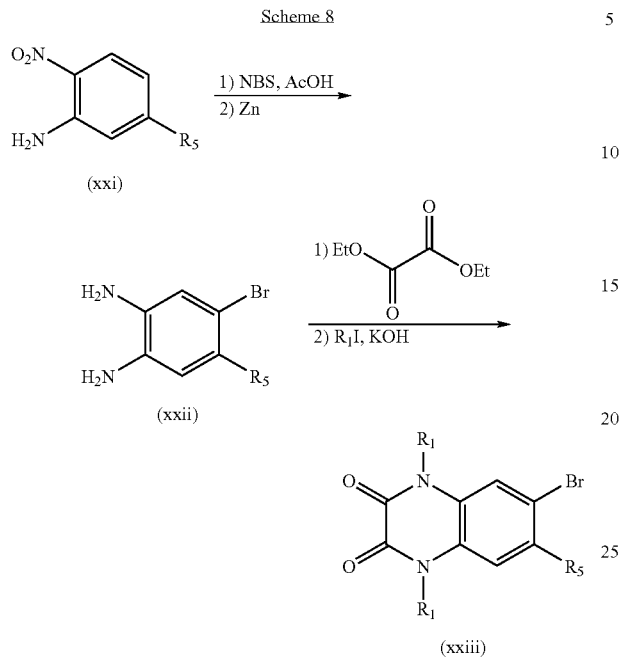

As shown in Scheme 8 wherein $R_1$ and $R_5$ are as described hereinabove, a substituted 2-amino nitrobenzene (xxi) can be brominated by reaction with NBS. The nitro group of the product can be reduced with zinc to yield the diamino intermediate (xxii) The diamine was converted into 1,4-dihydroquinoxaline-2,3-dione which can then undergo N-alkylation to yield the 1,4 dialkyl-quinoxaline-2,3-dione (xxiii). This intermediate can be used in the sequence shown in Scheme 1.

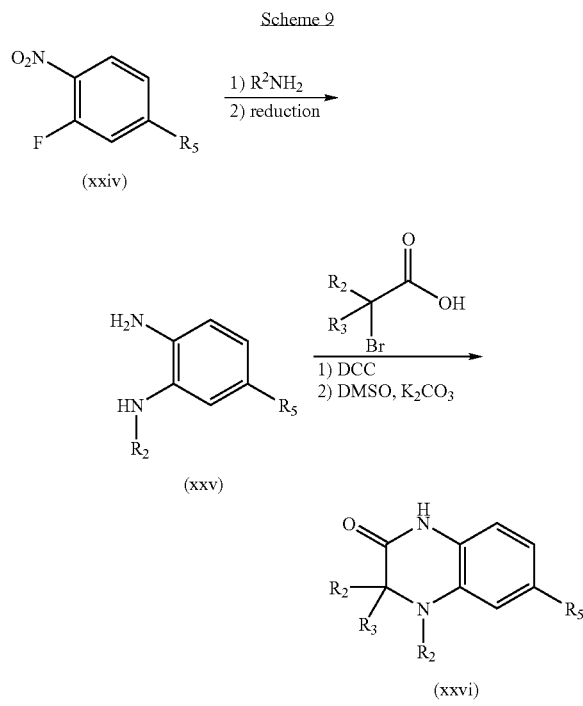

As shown in Scheme 9 wherein $R_1$, $R_2$, $R_3$, and $R_5$ are as described hereinabove, a substituted 2-fluoro-nitrobenzene (xxiv) can be converted into the diamino intermediate (xxv) by displacement of the fluoro group by an amine followed by reduction of the nitro group. The diamine can be converted into a substituted-3,4-dihydro-1H-quinoxalin-2-one (xxvi) by a two step reaction sequence that consists of a coupling reaction with α-bromo-carboxylic acid followed by cyclization under basic conditions. This intermediate can be used in the sequence shown in Scheme 1.

When $R_4$ is H or optionally substituted $C_{1-3}$alkyl and $R_5$ is

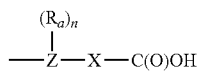

wherein Z, $R_a$, X are as described hereinabove, compounds of Formula I can be made in a similar fashion.

EXAMPLES

Example 1

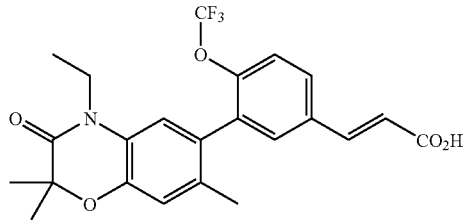

3-[3-(4-Ethyl-2,2,7-trimethyl-3-oxo-3,4-dihydro-2H-benzo[1,4]oxazin-6-yl)-4-trifluoromethoxy-phenyl]-acrylic acid (Compound 1)

A. 2,2,7-Trimethyl-4H-benzo[1,4]oxazin-3-one (Compound 1A)

A solution of 6-amino-m-cresol (10 g, 81.2 mmol) in dichloroethane (100 mL) was treated with 11.1 mL of 2-bromoisobutyryl bromide (89.3 mmol). The reaction was allowed to stir at room temperature for 3 hours, then refluxed overnight. The reaction was cooled to room temperature and filtered through celite. The filtrate and washings were combined and excess solvent removed to yield crude product which was then triturated with hexanes to give pure product as a white solid. MS (electrospray): mass calculated for $C_{11}H_{13}NO_2$, 191.09; m/z found 192.2, [M+H]$^+$.

B. 6-Bromo-2,2,7-trimethyl-4H-benzo[1,4]oxazin-3-one (Compound 1B)

A solution of Compound 1A (4.24 g, 22.2 mmol) in 150 mL of chloroform was treated with 5 mL of dry DMF followed by 4.4 g (24.4 mmol) of NBS at room temperature. After 4 hours, the reaction was quenched with 150 mL of a saturated sodium thiosulfate solution. The aqueous layer was extracted with chloroform and the combined organic layers were dried with magnesium sulfate, filtered, and excess solvent removed on the rotary evaporator. The crude product was purified via silica gel chromatography (5% EtOAc/Hexanes)

to yield 3.48 g of brominated product (58%). MS (electrospray): mass calculated for $C_{11}H_{12}BrNO_2$, 269.01; m/z found 268, $[M+H]^+$.

C. 6-Bromo-4-ethyl-2,2,7-trimethyl-4H-benzo[1,4]oxazin-3-one (Compound 1C)

Compound 1B (1.0 g, 3.7 mmol) was dissolved in 25 mL of DMSO and added to a prestirred 2.0 M solution of potassium hydroxide (415 mg, 7.4 mmol) in DMSO. Next, ethyl iodide (0.6 mL, 7.4 mmol) was added and the reaction stirred at room temperature overnight. The reaction was quenched with 75 mL of water and extracted with dichloromethane. The combined organic extracts were dried over magnesium sulfate, filtered and excess solvent removed to yield 1.04 g (95%) of desired product. MS (electrospray): mass calculated for $C_{13}H_{16}BrNO_2$, 297.04; m/z found 298, $[M+H]^+$.

D. 3-(4-Ethyl-2,2,7-trimethyl-3-oxo-3,4-dihydro-2H-benzo[1,4]oxazin-6-yl)-4-trifluoromethoxy-benzaldehyde (Compound 1D)

A round bottom flask was charged with Compound 1C (213 mg, 0.72 mmol), 2-methoxy-5-formylphenylboronic acid (210 mg, 0.89 mmol) and tetrakis(triphenylphosphine)palladium(0), (43 mg, 0.036 mmol). The flask was sealed and 3 mL of toluene and 1 mL of ethanol was added. The resulting solution was stirred to dissolve the reactants and then 1 mL of a 2 M $K_2CO_3$ solution was added via syringe. The reaction mixture was heated to 80° C. for 4 hours. After cooling, the reaction mixture was partitioned between ethyl acetate (50 mL) and water (25 mL). The water layer was further extracted (2×25 mL) and the combined organic layers were washed with water followed by brine, dried over magnesium sulfate, filtered and excess solvent removed on the rotary evaporator. The crude product was purified by flash chromatography (EtOAc/Hexanes; gradient 10% to 25%) to give 173 mg (60%) of product as white solid. MS (electrospray): mass calculated for $C_{21}H_{20}F_3NO_4$, 407.13; m/z found 408.1, $[M+H]^+$.

E. 3-[3-(4-Ethyl-2,2,7-trimethyl-3-oxo-3,4-dihydro-2H-benzo[1,4]oxazin-6-yl)-4-trifluoromethoxy-phenyl]-acrylic acid tert-butyl ester (Compound 1E)

A flask charged with dimethyl t-butoxycarbonyl-methylphosphonate (0.21 mL, 1.06 mmol) in 2 mL of dry THF/DMPU (10:1) was cooled to −78° C. where 0.52 mL of n-butyl lithium (2.5 M hexane solution, 32 mmol) was added slowly via syringe. The reaction mixture was stirred at −78° C. for 10 minutes and then a solution of Compound 1D (173 mg, 0.43 mmol) in 2 mL of dry THF was added. After warming to room temperature and an additional 20 minutes of stirring, the reaction was quenched with 5 mL of water and passed through a solid phase extraction column (SPE). The column was washed with EtOAc (50 mL) and the collected eluant was evaporated to give crude product which was purified by flash chromatography (EtOAc/Hexanes; gradient 15% to 30%) to give 126 mg (60%) of product as a white solid. MS (electrospray): mass calculated for $C_{27}H_{30}F_3NO_5$, 505.21; m/z found 506.2, $[M+H]^+$.

F. 3-[3-(4-Ethyl-2,2,7-trimethyl-3-oxo-3,4-dihydro-2H-benzo[1,4]oxazin-6-yl)-4-trifluoromethoxy-phenyl]-acrylic acid (Compound 1)

A solution of Compound 1E (1.71 g, 3.4 mmol) in 15 mL of dichloromethane and 5 mL of trifluoroacetic acid was stirred at room temperature overnight. The reaction mixture was then concentrated on the rotary evaporator and redissolved in 20 mL of diethyl ether. To this solution, hexanes were added to give a cloudy solution from which 1.5 g (100%) of product precipitated out as a white solid (Compound 1). MS (electrospray): mass calculated for $C_{23}H_{22}F_3NO_5$, 449.15; m/z found 462.3, $[M+H]^+$.

Example 2

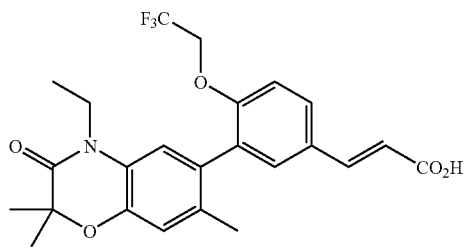

3-[3-(4-Ethyl-2,2,7-trimethyl-3-oxo-3,4-dihydro-2H-benzo[1,4]oxazin-6-yl)-4-(2,2,2-trifluoro-ethoxy)-phenyl]-acrylic acid (Compound 2)

A. 3-(4-Ethyl-2,2,7-trimethyl-3-oxo-3,4-dihydro-2H-benzo[1,4]oxazin-6-yl)-4-methoxy-benzaldehyde (Compound 2A)

This was prepared using a procedure similar to that described to make Compound 1D, except using Compound 1C and 2-methoxy-5-formylphenylboronic acid in Step D. MS (electrospray): mass calculated for $C_{21}H_{23}NO_4$, 353.16; m/z found 354.1 $[M+H]^+$.

B. 3-(4-Ethyl-2,2,7-trimethyl-3-oxo-3,4-dihydro-2H-benzo[1,4]oxazin-6-yl)-4-hydroxy-benzaldehyde (Compound 2B)

A solution of Compound 2A (240 mg, 0.68 mmol) in 3 mL of dry DMF was treated with sodium thioethoxide (143 mg, 1.7 mmol). The reaction flask was then equipped with a reflux condenser, nitrogen inlet and heated to 80° C. for 2 hours. The reaction mixture was allowed to cool to room temperature and 5 mL of water is added and the reaction mixture passed through a SPE. The crude compound was eluted with EtOAc. The collected eluant was dried of excess solvent to yield product which was used without further purification in the next step. MS (electrospray): mass calculated for $C_{20}H_{21}NO_4$, 339.15 m/z found 340.1, $[M+H]^+$.

C. 3-(4-Ethyl-2,2,7-trimethyl-3-oxo-3,4-dihydro-2H-benzo[1,4]oxazin-6-yl)-4-(2,2,2-trifluoro-ethoxy)-benzaldehyde (Compound 2C)

A solution of Compound 2B (0.68 mmol) in 3 mL of acetone was treated with potassium carbonate (122 g, 0.88 mmol) and 2,2,2-trifluoroethyl nonafluorobutanesulfonate (0.18 mL, 0.78 mmol). The flask was heated in an oil bath to 55° C. for 4 hours. When the reaction was complete, the flask was allowed to cool to room temperature and the solids were filtered off. The crude product was obtained by removal of excess solvent, followed by redissolving the product in chloroform and filtering off any remaining solids. After evaporating the excess solvent 105 mg of product (37% over 2 steps) was obtained as a white solid. MS (electrospray): mass calculated for $C_{22}H_{22}F_3NO_4$, 421.15; m/z found 422.1, $[M+H]^+$.

D. 3-[3-(4-Ethyl-2,2,7-trimethyl-3-oxo-3,4-dihydro-2H-benzo[1,4]oxazin-6-yl)-4-(2,2,2-trifluoro-ethoxy)-phenyl]-acrylic acid tert-butyl ester (Compound 2D)

This was made from Compound 2C using a procedure similar to that described for Compound 1E. MS (electrospray): mass calculated for $C_{28}H_{32}F_3NO_5$, 519.2; m/z found 520.2, $[M+H]^+$.

E. 3-[3-(4-Ethyl-2,2,7-trimethyl-3-oxo-3,4-dihydro-2H-benzo[1,4]oxazin-6-yl-4-(2,2,2-trifluoro-ethoxy)-phenyl] acrylic acid (Compound 2)

Compound 2 was made from Compound 2D using a procedure similar to that described for Compound 1F. MS (electrospray): mass calculated for $C_{24}H_{24}F_3NO_5$, 463.16; m/z found 464.2, [M+H]$^+$.

Example 3

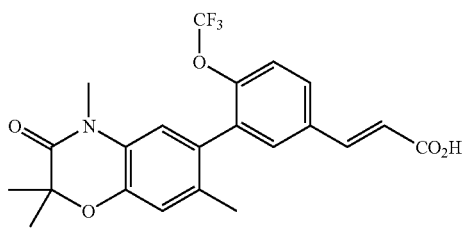

3-[3-(2,2,4,7-Tetramethyl-3-oxo-3,4-dihydro-2H-benzo[1,4]oxazin-6-yl)-4-trifluoromethoxy-phenyl]-acrylic acid (Compound 3)

A. 6-Bromo-2,2,4,7-tetramethyl-4H-benzo[1,4]oxazin-3-one (Compound 3A)

This was prepared using a procedure similar to that described to make Compound 1C, except using methyl iodide in Step 1C. MS (electrospray): mass calculated for $C_{12}H_{14}BrNO_2$, 283.02; m/z found 284 [M+H]$^+$.

B. 3-[3-(2,2,4,7-Tetramethyl-3-oxo-3,4-dihydro-2H-benzo[1,4]oxazin-6-yl)-4-trifluoromethoxy-phenyl]-acrylic acid (Compound 3)

Compound 3 was prepared using a procedure similar to that described to make Compound 1F, except using Compound 3A in Step 1D. MS (electrospray): mass calculated for $C_{22}H_{20}F_3NO_5$, 435.13; m/z found 436.1 [M+H]$^+$.

Example 4

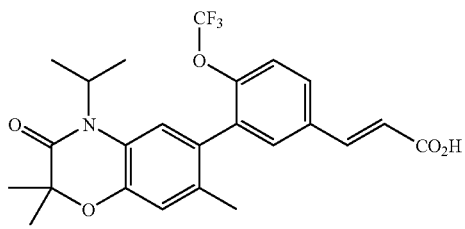

3-[3-(4-Isopropyl-2,2,7-trimethyl-3-oxo-3,4-dihydro-2H-benzol[1,4]oxazin-6-yl)-4-trifluoromethoxy-phenyl]-acrylic acid (Compound 4)

A. 6-Bromo-4-isopropyl-2,2,7-trimethyl-4H-benzo[1,4]oxazin-3-one (Compound 4A)

This was prepared using a procedure similar to that described to make Compound 1C, except using 1-propyl iodide in Step C. MS (electrospray): mass calculated for $C_{14}H_{18}BrNO_2$, 311.05; m/z found 312 [M+H]$^+$.

B. 3-[3-(4-Isopropyl-2,2,7-trimethyl-3-oxo-3,4-dihydro-2H-benzo[1,4]oxazin-6-yl)-4-trifluoromethoxy-phenyl]-acrylic acid (Compound 4)

Compound 4 was prepared using a procedure similar to that described to make Compound 1F, except using Compound 4A in Step 1D. MS (electrospray): mass calculated for $C_{24}H_{24}F_3NO_5$, 463.16; m/z found 464.2 [M+H]$^+$.

Example 5

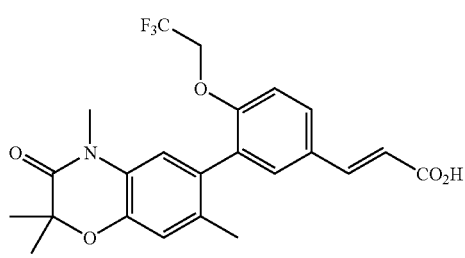

3-[3-(2,2,4,7-Tetramethyl-3-oxo-3,4-dihydro-2H-benzo[1,4]oxazin-6-yl)-4-(2,2,2-trifluoro-ethoxy)-phenyl]-acrylic acid (Compound 5)

This was prepared using a procedure similar to that described to make Compound 2E, except using Compound 3A as the starting material in Step 2A. MS (electrospray): mass calculated for $C_{23}H_{22}F_3NO_5$, 449.15, m/z found 450.1 [M+H]$^+$.

Example 6

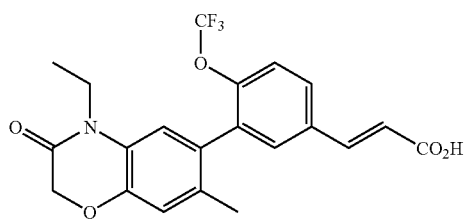

3-[3-(4-Ethyl-7-methyl-3-oxo-3,4-dihydro-2H-benzo[1,4]oxazin-6-yl)-4-trifluoromethoxy-phenyl]-acrylic acid (Compound 6)

This was prepared using a procedure similar to that described to make Compound 1F, except using bromoacetyl bromide in Step 1A. MS (electrospray): mass calculated for $C_{21}H_{18}F_3NO_5$, 421.11; m/z found 422.2 [M+H]⁺.

Example 7

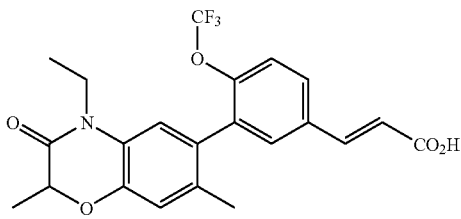

3-[3-(4-Ethyl-2,7-dimethyl-3-oxo-3,4-dihydro-2H-benzo[1,4]oxazin-6-yl)-4-triflouromethoxy-phenyl]-acrylic acid (Compound 7)

This was prepared using a procedure similar to that described to make Compound 1F, except using 2-bromopropionyl bromide in Step 1A. MS (electrospray): mass calculated for $C_{22}H_{20}F_3NO_5$, 435.13; m/z found 435.1 [M+H]⁺.

Example 8

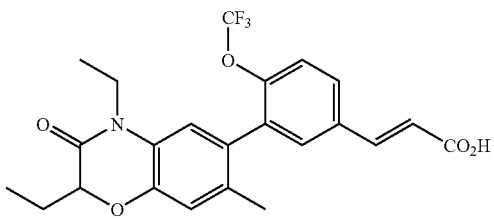

3-[3-(2,4-Diethyl-7-methyl-3-oxo-3,4-dihydro-2H-benzo[1,4]oxazin-6-yl)-4-trifluoromethoxy-phenyl]-acrylic acid (Compound 8)

This was prepared using a procedure similar to that described to make Compound 1F, except using 2-bromobutyryl bromide in Step 1A. MS (electrospray): mass calculated for $C_{23}H_{22}F_3NO_5$, 449.15; m/z found 450.1 [M+H]⁺.

Example 9

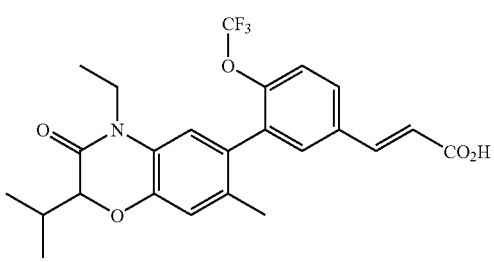

3-[3-(4-Ethyl-2-isopropyl-7-methyl-3-oxo-3,4-dihydro-2H-benzo[1,4]oxazin-6-yl)-4-trifluoromethoxy-phenyl]-acrylic acid (Compound 9)

A. 2-Isopropyl-7-methyl-4H-benzo[1,4]oxazin-3-one (Compound 9A)

A solution of 6-amino-m-cresol (1.0 g, 8.1 mmol) in 10 mL of dry dichloroethane is add to a prestirred solution of 2-bromo-3-methylbutyic acid (1.61 g, 8.9 mmol) and 1-(3-dimethylaminopropyl)-3-ethylcarbodiimide hydrochloride (1.71 g, 8.9 mmol) in 20 mL of dry dichloroethane. The reaction stirred overnight before quenching with water (50 mL) and extracting with chlrorform (3×50 mL). The combined organic layers were dried with sodium sulfate, filtered and excess solvent removed on the rotary evaporator. The crude solid was then dissolved in 15 mL of dry DMF and treated with cesium carbonate (5.86 g, 18 mmol) and heated to 80° C. for 6 hours. The reaction mixture was then cooled and quenched with 50 mL of water and extracted with chloroform (3×50 mL). The combined organic layers were dried with sodium sulfate, filtered and excess solvent removed on the rotary evaporator. The crude product was then purified using flash chromatography (10% EtOAc/hexanes) to yield 1.08 g (65%) of product as an off white solid. MS (electrospray): mass calculated for $C_{12}H_{15}NO_2$, 205.11; m/z found 206.1 [M+H]⁺.

B. 3-[3-(4-Ethyl-2-isopropyl-7-methyl-3-oxo-3,4-dihydro-2H-benzo[1,4]oxazin-6-yl)-4-trifluoromethoxy-phenyl]-acrylic acid (Compound 9)

Compound 9 was prepared using a procedure similar to that described to make Compound 1F, except using Compound 9A as the starting material in Step 1B. MS (electrospray): mass calculated for $C_{24}H_{24}F_3NO_5$, 463.16; m/z found 464.2 [M+H]⁺.

Example 10

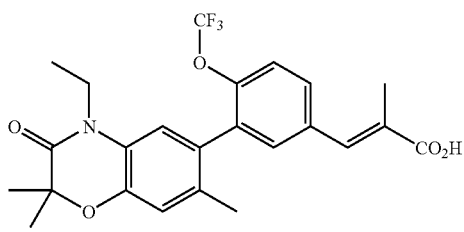

3-[3-(4-Ethyl-2,2,7-trimethyl-3-oxo-3,4-dihydro-2H-benzo[1,4]oxazin-6-yl)-4-trifluoromethoxy-phenyl]-2-methyl-acrylic acid (Compound 10)

This was prepared using a procedure similar to that described to make Compound 1F, except using triethyl-2-phosphonopropionate in Step 1E and the hydrolysis in Step 1F is done with refluxing LiOH in THF/water. MS (electrospray): mass calculated for $C_{24}H_{24}F_3NO_5$, 463.16; m/z found 464.2 $[M+H]^+$.

Example 11

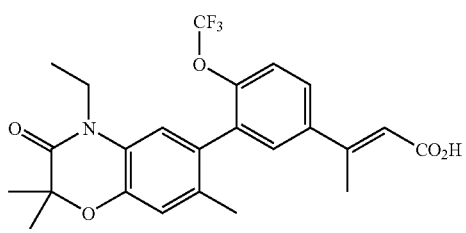

3-[3-(4-Ethyl-2,2,7-trimethyl-3-oxo-3,4-dihydro-2H-benzo[1,4]oxazin-6-yl)-4-trifluoromethoxy-phenyl]-but-2-enoic acid (Compound 11)

A. 6-(5-Acetyl-2-trifluoromethoxy-phenyl)-4-ethyl-2,2,7-trimethyl-4H-benzo[1,4]oxazin-3-one (Compound 11A)

A solution of Compound 1D (200 mg, 0.49 mmol) in dry 3 mL of dry THF is cooled to −78° C. and treated with a 3M solution of methyl magnesium bromide in diethyl ether (0.17 mL, 0.54 mmol). The reaction was allowed to warm to room temperature, the reaction turned blue when it was complete. The mixture was quenched with 5 mL of a saturated aqueous solution of $NH_4Cl$ and passed through a SPE. The crude product was eluted with EtOAc. After removing excess solvent the crude alcohol was then dissolved in 2 mL of dichloromethane and treated with Dess-Martin reagent (250 mg, 0.59 mmol) and stirred at room temperature overnight. The reaction was quenched with 4 mL of saturated sodium thiosulfate solution and 4 mL of saturated sodium bicarbonate solution, the reaction mixture was stirred until clear. The reaction mixture was passed through another SPE and eluted with dichloromethane, removal of solvent yielded crude ketone which was purified with flash chromatography (25% EtOAc/hexane) to yield 95 mg (46%) of the desired product and a white solid. MS (electrospray): mass calculated for $C_{22}H_{22}F_3NO_4$, 421.15; m/z found 422.1 $[M+H]^+$.

B. 3-[3-(4-Ethyl-2,2,7-trimethyl-3-oxo-3,4-dihydro-2H-benzo[1,4]oxazin-6-yl)-4-trifluoromethoxy-phenyl]-but-2-enoic acid (Compound 11)

Compound 11 was prepared using a procedure similar to that described to make Compound 1F, except using Compound 11A as the starting material in Step 1E. MS (electrospray): mass calculated for $C_{24}H_{24}F_3NO_5$, 463.16; m/z found 464.2 $[M+H]^+$.

Example 12

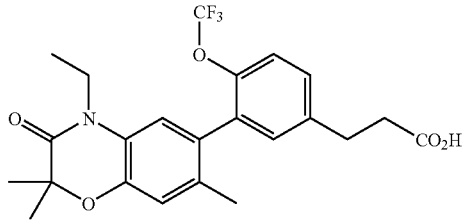

3-[3-(4-Ethyl-2,2,7-trimethyl-3-oxo-3,4-dihydro-2H-benzo[1,4]oxazin-6-yl)-4-trifluoromethoxy-phenyl]-propionic acid (Compound 12)

Compound 1F, was dissolved in EtOAc and hydrogenated with 10% Pd/C and $H_2$ balloon for 4 hours. Pd/C was then filtered off and solvent was evaporated to afford product as colorless oil. Evaporation from hexane or ether afforded product (100%) as white sticky foam. Product was further dried under high vacuum. MS (electrospray): mass calculated for $C_{23}H_{24}F_3NO_5$, 451.16; m/z found 452.2, $[M+H]^+$.

Example 13

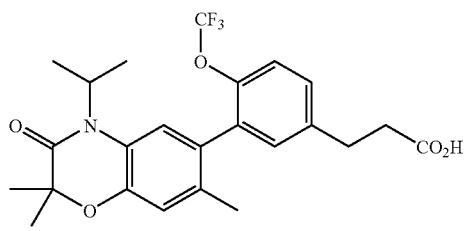

3-[3-4-Isopropyl-2,2,7-trimethyl-3-oxo-3,4-dihydro-2H-benzo[1,4]oxazin-6-yl)-4-trifluoromethoxy-phenyl]-propionic acid (Compound 13)

This was prepared from Compound 4B using the procedure described in Example 12. MS (electrospray): mass calculated for $C_{24}H_{26}F_3NO_5$, 465.18; m/z found 466.2 $[M+H]^+$.

Example 14

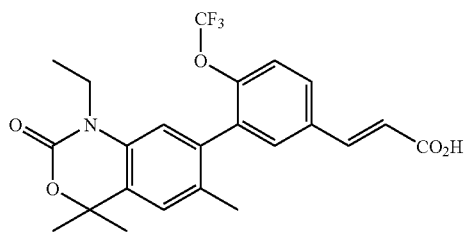

3-[3-(1-Ethyl-4,4,6-trimethyl-2-oxo-1,4-dihydro-2H-benzo[d][1,3]oxazin-7-yl)-4trifluoromethoxy-phenyl]-acrylic acid (Compound 14)

A. 2-(2-Amino-5-methyl-phenyl)-propan-2-ol (Compound 14A)

Compound 14A was synthesized by using the procedure reported in U.S. Pat. No. 6,444,668B1.

To a solution of 2-amino-5-methylbenzoic acid (20 mmol, 3.02 g) in 100 mL THF was added a solution of MeMgBr in THF (3.0 M, 120 mmol, 40 mL) dropwise at −78°. The original golden yellow solution turned to a yellow-green slurry. After allowing the reaction to warm to r.t., it was stirred for two days. The reaction was quenched by adding ice-water The solution was basified with dilute NaOH and was extracted with EtOAc. The organic layer was washed with brine, separated and dried over $Na_2SO_4$, filtered and concentrated in vacuo. The orange gummy residue was then purified by column chromatography (4:1 hexanes/EtOAc to 3:1 hexanes/EtOAc) to obtain 2-(2-amino-5-methyl-phenyl)-propan-2-ol as a thick orange oil (1.9 g, 57% yield). MS (electrospray): mass calculated for $C_{10}H_{15}NO$, 165.12; m/z found 166, $[M+H]^+$.

B. 4,4,6-Trimethyl-1,4-dihydro-benzo[d][1,3]oxazin-2-one (Compound 14B)

To a solution of Compound 14A (11.8 mmol, 1.95 g) in 200 mL THF was added Et₃N (29.6 mmol, 4.06 mL) at 0° C. followed by a dropwise addition of a solution of phosgene in toluene (20% solution, 12.19 mmol, 7.9 mL). The reaction mixture was stirred at r.t. overnight It was extracted with Et₂O, washed with water and brine. The organic layer was dried over Na₂SO₄, filtered and the solvent was removed in vacuo to the desired product (2.14 g, expected wt.=2.25 g) which was used in the next step without further purification. MS (electrospray): mass calculated for $C_{11}H_{13}NO_2$, 191.09, m/z found 192 (100%), $[M+H]^+$.

C. 7-Bromo-1-ethyl-4,4,6-trimethyl-1,4-dihydro-benzo[d][1,3]oxazin-2-one (Compound 14C)

To a solution of Compound 14B (11.5 mmol, 2.14) in 130 mL CH₂Cl₂ and 2 mL DMF was added N-bromosuccinamide (17.25 mmol, 3.0 g) in one portion at r.t. The orange solution was stirred overnight. The reaction mixture was washed with water, brine and the organic layer was dried over Na₂SO₄. The solvent was removed in vacuo to obtain 7-bromo-1-ethyl-4,4,6-trimethyl-1,4-dihydro-benzo[d][1,3]oxazin-2-one as yellow powder (2.58 g, 83% yield). It was used in the next step without purification. MS (electrospray): mass calculated for $C_{13}H_{16}BrNO_2$, 297.04; m/z found 298, $[M+H]^+$.

D. 7-Bromo-1-ethyl-4,4,6-trimethyl-1,4-dihydro-benzo[d][1,3]oxazin-2-one (Compound 14D)

To a solution of a finely powdered KOH (2.0 mmol, 0.112 g) in 10 mL DMSO at 15° C. (ice-water bath) was added Compound 14C (2.0 mmol, 0.54 g) in one portion as a solid. After stirring the golden yellow solution for 15 min, iodoethane (2.0 mmol, 0.16 mL) was added dropwise and the solution was allowed to stir overnight. The reaction mixture was diluted with water and was extracted with Et₂O. The ether extracts were washed with water, brine and then dried over Na₂SO₄. The solvent was removed in vacuo to obtain 7-bromo-1-ethyl-4,4,6-trimethyl-1,4-dihydro-benzo[d][1,3]oxazin-2-one as yellow solid (0.53 g). It was used in the next step without purification. MS (electrospray): mass calculated for $C_{13}H_{16}BrNO_2$, 297.04; m/z found 298, $[M+H]^+$.

E. 3-(1-Ethyl-4,4,6-trimethyl-2-oxo-1,4-dihydro-2H-benzo[d][1,3]oxazin-7-yl)-4-trifluoromethoxy-benzaldehyde (Compound 14E)

A round bottom flask was charged with 0.5 g (1.67 mmol) of Compound 14D, 0.58 g (2,5 mmol) of 2-trifluoromethoxy-5-formylphenylboronic acid and 0.083 g of tetrakis(triphenylphosphine)palladium(0). The flask was sealed with a septa and 8.5 mL of toluene and 2.5 mL of ethanol was added. The resulting solution was stirred to dissolve the reactants and then 1.7 mL of 2M K₂CO₃ was added via syringe. The reaction mixture was heated to 80° C. for 4 hours. After cooling, the reaction mixture was partitioned between ethyl acatate (20 mL) and water (8 mL). The water layer was further extracted (2×10 mL) and the combined organic layers were washed with water (10 mL) followed by brine (10 mL), dried over magnesium sulfate, filtered and excess solvent removed on the rotary evaporator. The crude product was purified by flash chromatography (EtOAc/Hexanes; gradient 20% to 40%) to give 0.35 g (52%) of 3-(1-ethyl-4,4,6-trimethyl-2-oxo-1,4-dihydro-2H-benzo[d][1,3]oxazin-7-yl)-4-trifluoromethoxy-benzaldehyde as yellow solid. MS (electrospray): mass calculated for $C_{21}H_{20}F_3NO_4$, 407.13; m/z found 408 $[M+H]^+$.

F. 3-[3-(1-Ethyl-4,4,6-trimethyl-2-oxo-1,4-dihydro-2H-benzo[d][1,3]oxazin-7-yl)-4-trifluoromethoxy-phenyl]-acrylic acid tert-butyl ester (Compound 14F)

A flask charged with 0.23 mL (2.5 mmol) of dimethyl t-butoxycarbonyl-methylphosphonate in 8.75 mL of dry THF/DMPU (10:1). The flask was cooled to −78° C. where 1.78 mL (0.9 mmol, 2.5M hexanes) of n-butyl lithium was added slowly via syringe. The reaction mixture was stirred at −78° C. for 10 minutes and then a solution of 0.35 g (0.86 mmol) of Compound 14E in 3 mL of dry THF was added. After warming to room temperature and an additional 20 minutes of stirring, the reaction was quenched with 3 mL of water and then partitioned with 10 mL of saturated ammonium chloride and 20 mL of ethyl acetate, The water layer was further extracted with ethyl acetate (2×15 mL) and the combined organic layers were then washed with brine (10 mL), dried over magnesium sulfate, filtered and excess solvent was removed on the rotary evaporator. The crude product was purified by flash chromatography (3.5:1 EtOAc/Hexanes) to give 0.16 g (41%) of the product as a white solid. MS (electrospray): mass calculated for $C_{23}H_{22}F_3NO_5$, 449.15; m/z found 450, $[M+H]^+$.

G. 3-[3-(1-Ethyl-4,4,6-trimethyl-2-oxo-1,4-dihydro-2H-benzo[d][1,3]oxazin-7-yl)-4-trifluoromethoxy-phenyl]-acrylic acid (Compound 14)

A solution of 0.068 g (0.15 mmol) of Compound 14F in 3 mL of dichloromethane and 2.5 mL of trifluoroacetic acid was stirred at room temperature overnight. The reaction mixture was then concentrated on the rotary evaporator to obtain 3-[3-(1-ethyl-4,4,6-trimethyl-2-oxo-1,4-dihydro-2H-benzo[d][1,3]oxazin-7-yl)-4-trifluoromethoxy-phenyl]-acrylic acid as a white solid (Compound 14, 0.06 g). MS (electrospray): mass calculated for $C_{257}H_{30}F_3NO_5$, 505.13; m/z found 506, $[M+H]^+$.

Example 15

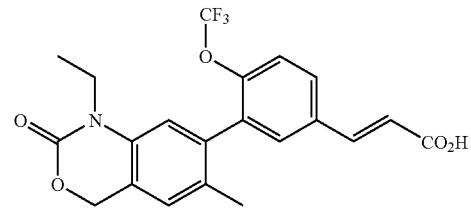

3-[3-(1-Ethyl-6-methyl-2-oxo-1,4-dihydro-2H-benzo[d][1,3]oxazin-7-yl)-4-trifluoromethoxy-phenyl]-acrylic acid (Compound 15)

A. 6-Methyl-1,4-dihydro-benzo[d][1,3]oxazin-2-one (Compound 15A)

Compound 15A was synthesized using a procedure reported by Nikam et al. *J. Org. Chem.* 1997, 62, 9331.

To a solution of (2-amino-5-methyl-phenyl)-methanol (5.24 mmol, 0.71 g) in 100 mL THF was added Et₃N (13.13 mmol, 1.8 mL) at 0° C. followed by a dropwise addition of a solution of phosgene in toluene (20% solution, 5.4 mmol, 3.5 mL). The reaction mixture was stirred at r.t. overnight. It was extracted with Et₂O, washed with water and brine. The organic layer was dried over Na₂SO₄, filtered and the solvent was removed in vacuo to obtain 6-methyl-1,4, -dihydro-benzo[d][1,3]oxazin-2-one as a yellow solid (0.9 g, expected wt.=0.85 g) which was used in the next step without further purification. MS (electrospray): mass calculated for $C_9H_9NO_2$, 163.06; m/z found 164, [M+H]$^+$.

B. 3-[3-(1-Ethyl-6-methyl-2-oxo-1,4-dihydro-2H-benzo[d] 1,3, oxazin-7-yl)-4-trifluoromethoxy-phenyl]-acrytic acid (Compound 15)

Compound 15 was prepared using a procedure similar to that described to make Compound 14G, except using Compound 15A as the starting material in Step 14B. MS (electrospray): mass calculated for $C_{21}H_{18}F_3NO_5$, 421.11; m/z found 422 [M+H]$^+$.

Example 16

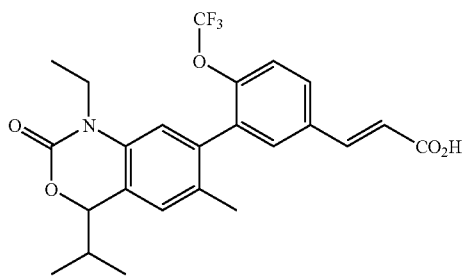

3-[3-(1-Ethyl-4-isopropyl-6-methyl-2-oxo-1,4-dihydro-2H-benzo[d][1,3]oxazin-7-yl)-4-trifluoromethoxy-phenyl]-acrylic acid (Compound 16)

A. (2-Hydroxymethyl-4-methyl-phenyl)-carbamic acid tert-butyl ester (Compound 16A)

To a solution of (2-amino-5-methyl-phenyl)-methanol (18.08 mmol, 2.48 g) in 50 mL $CH_2Cl_2$ was added $Et_3N$ (20 mmol, 2.8 mL) was added $BOC_2O$ and the reaction was allowed to stir overnight at r.t. for two days. The reaction mixture was washed with dilute HCl solution. The organic layer was separated, dried over $Na_2SO_4$, filtered and the solvent was removed in vacuo. (2-Hydroxymethyl-4-methyl-phenyl)-carbamic acid tert-butyl ester was obtained as a golden yellow thick oil (4.2 g) which was used in the next step without purification. MS (electrospray): mass calculated for $C_{13}H_{19}NO_3$, 237.14; m/z found 238, [M+H]$^+$.

B. (2-Formyl-4-methyl-phenyl)-carbamic acid tert-butyl ester (Compound 16B)

Compound 16A (6.33 mmol, 1.5 g) was dissolved in 75 mL of $CH_2Cl_2$ and then $MnO_2$ (75 mmol, 6.55 g) was added. The black suspension was stirred overnight at r.t. and then filtered through a pad of celite. The celite pad was washed with $CH_2Cl_2$ and the combined filtrates were dried over $Na_2SO_4$. The solvent was filtered and the solvent was removed in vacuo to yield (2-formyl-4-methyl-phenyl)-carbamic acid tert-butyl ester as yellow thick oil (1.45 g). MS (electrospray): mass calculated for $C_{13}H_{17}NO_3$, 235.12; m/z found 236, [M+H]$^+$.

C. 4-Isopropyl-6-methyl-1,4-dihydro-benzo[d][1,3]oxazin-2-one (Compound 16C)

To a solution of Compound 16B (6.3 mmol, 1.45 g) in 6 mL THF was added a solution of isopropylmagnesium chloride in THF (2M, 18 mmol, 9.0 mL) at 0° C. The reaction mixture was stirred at r.t. for four days and then quenched with water. It was extracted with EtOAc and washed with brine. The organic layer was dried over $Na_2SO_4$, filtered and the solvent was removed in vacuo to obtain a 1:1 mixture of [2-(1-hydroxy-2-methyl-propyl)-4-methyl-phenyl]-carbamic acid tert-butyl ester and 4-isopropyl-6-methyl-1,4-dihydro-benzo[d][1,3]oxazin-2-one as a yellow oil. The crude mixture was dissolved in 75 mL THF and 60% NaH (10 mmol, 0.4 g) was added at r.t. The reaction mixture was stirred at r.t. for two days. The reaction was quenched with water and extracted with EtOAc. The organic layer was washed with brine, dried over $Na_2SO_4$, filtered and the solvent was removed in vacuo to obtain yellow oil. It was purified by column chromatography with 3:1 hexanes/EtOAc as the eluting system to obtain 4-isopropyl-6-methyl-1,4-dihydro-benzo[d][1,3]oxazin-2-one (0.8 g, 63% yield) as a pale yellow glassy oil. MS (electrospray): mass calculated for $C_{12}H_{15}NO_2$, 205.11; m/z found 206 (100%), [M+H]$^+$.

D. 3-[3-(1-Ethyl-4-isopropyl-6-methyl-2-oxo-1,4-dihydro-2H-benzo[d][1,3]oxazin-7-yl)-4-trifluoromethoxy-phenyl]-acrylic acid (Compound 16)

Compound 16 was prepared using a procedure similar to that described to make Compound 14G, except using Compound 16C as the starting material in Step 14C. MS (electrospray): mass calculated for $C_{24}H_{24}F_3NO_5$, 463.16; m/z found 464, [M+H]$^+$.

Example 17

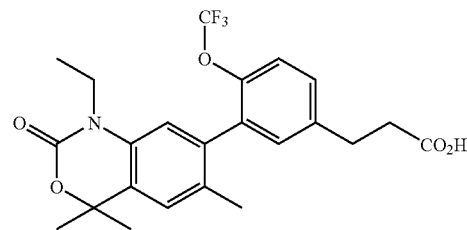

3-[3-(1-Ethyl-4,4,6-trimethyl-2-oxo-1,4-dihydro-2H-benzo[d][1,3]oxazin-7-yl)-4-triluoromethoxy-phenyl]-propionic acid (Compound 17)

This was prepared from Compound 14F using the procedure described in Example 12. MS (electrospray): mass calculated for $C_{23}H_{24}F_3NO_5$, 451.16; m/z found 452 [M+H]$^+$.

Example 18

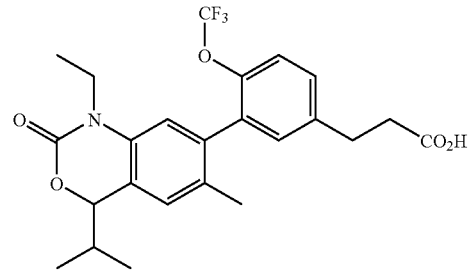

3-[3-(1-Ethyl-4-isopropyl-6-methyl-2-oxo-1,4-dihydro-2H-benzo[d][1,3]oxazin-7-yl)4trifluoromethoxyphenyl]-propionic acid (Compound 18)

This was prepared from Compound 16 using the procedure described in Example 12. MS (electrospray): mass calculated for $C_{24}H_{26}F_3NO_5$, 465.18; m/z found 466.2 $[M+H]^+$.

Example 19

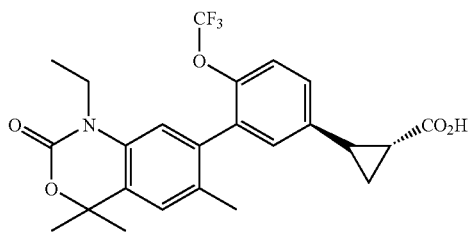

2-[3-(1-Ethyl-4,4,6-trimethyl-2-oxo-1,4-dihydro-2H-benzo[d][1,3]oxazin-7-yl)-4-trifuoromethoxy-phenyl]-cyclopropanecarboxylic acid (Compound 19)

A. 2-[3-(1-Ethyl-4,4,6-trimethyl-2-oxo-1,4-dihydro-2H-benzo[d][1,3]oxazin-7-yl)-4-trifluoromethoxy-phenyl]-cyclopropanecarboxylic acid tert-butyl ester (Compound 19A)

To a round bottom flask was added trimethylsulfoxonium iodide (1.7 mmol, 0.37 g) and 60% NaH (1.7 mmol, 0.07 g) and the flask was cooled to −10° C. with an ice-water bath. DMSO (2 mL) was then added dropwise. Initially a foamy suspension was observed. The cooling bath was removed and the reaction mixture was allowed to stir at r.t. for 30-40 min till the reaction mixture became a turbid solution. Compound 16F (0.17 mmol, 0.085 g) was then dissolved in 1.5 mL DMSO and was added to the reaction mixture. The golden yellow solution was stirred at 50° C. (oil bath) for 2 h. After cooling to r.t., the reaction mixture was poured into 50 mL of ice-water. It was extracted with EtOAc (3×15 mL). The organic layer was washed with water followed by brine and was then dried over $Na_2SO_4$. The solvent was filtered and evaporated in vacuo to obtain the desired product as a colorless oil. It was purified by column chromatography with 3.5:1 hexanes-EtOAc as the eluting system to obtain 0.05 g of the product as a white foam. The product has the same Rf as the starting material. However, the product does not stain with $KMnO_4$ stain indicating the disappearance of the double bond while the starting material does. MS (electrospray): mass calculated for $C_{28}H_{32}F_3NO_5$, 519.22; m/z found 520 $[M+H]^+$.

B. 2-[3-(1-Ethyl-4,4,6-trimethyl-2-oxo-1,2,3,4-tetrahydro-quinolin-7-yl)-4-trifluoromethoxy-phenyl]-cyclopropanecarboxylic acid (Compound 19)

To a solution of Compound 19A in $CH_2Cl_2$ (2 mL) was added TFA (1 mL). The solution was stirred at r.t. overnight and the solvent was removed in vacuo to obtain 2-[3-(1-ethyl-4,4,6-trimethyl-2-oxo-1,2,3,4-tetrahydro-quinolin-7-yl)-4-trifluoromethoxy-phenyl]-cyclopropanecarboxylic acid as pale yellow powder ((Compound 19, 0.036 g). MS (electrospray): mass calculated for $C_{24}H_{24}F_3NO_5$, 463.16; m/z found 464 $[M+H]^+$.

Example 20

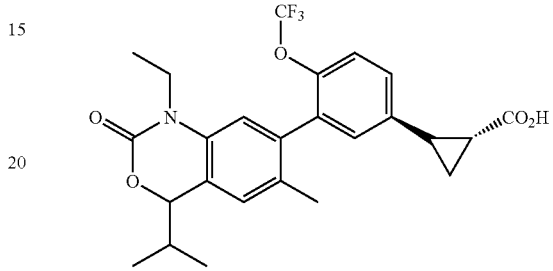

2-[3-(1-Ethyl-4-isopropyl-6-methyl-2-oxo-1,4-dihydro-2H-benzo[d][1,3]oxazin-7-yl)-4-trifluoromethoxy-phenyl]-cyclopropanecarboxylic acid (Compound 20)

This compound was synthesized as a mixture of diastereomers from the t-butyl ester of Compound 16, using a procedure similar to that described in Example 19. MS (electrospray): mass calculated for $C_{25}H_{26}F_3NO_5$, 477.18; m/z found 478 $[M+H]^+$.

Example 21

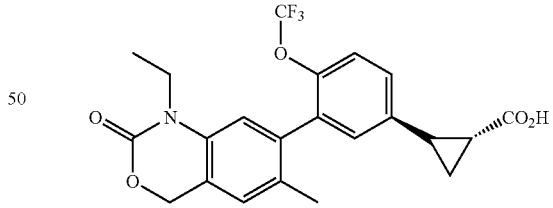

2-[3-(1-Ethyl-6-methyl-2-oxo-1,4-dihydro-2H-benzo[d]1[1,3]oxazin-7-yl)-4-trifluoromethoxy-phenyl]-cyclopropanecarboxylic acid (Compound 21)

This compound was synthesized as a mixture of diastereomers from the t-butyl ester of Compound 15, using a procedure similar to that described in Example 19. MS (electrospray): mass calculated for $C_{22}H_{20}F_3NO_5$, 435.13; m/z found 436 $[M+H]^+$.

Example 22

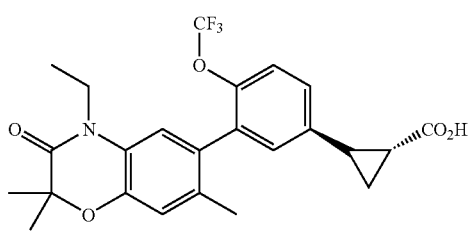

2-[3-(4-Ethyl-2,2,7-trimethyl-3-oxo-3,4-dihydro-2H-benzo[1,4]oxazin-6-yl)-4-trifluoromethoxy-phenyl]-cyclopropanecarboxylic acid (Compound 22)

This compound was synthesized as a mixture of diastereomers from Compound 1E using a procedure similar to that described in Example 19, MS (electrospray): mass calculated for $C_{24}H_{24}F_3NO_5$, 463.16; m/z found 464 $[M+H]^+$.

Example 23

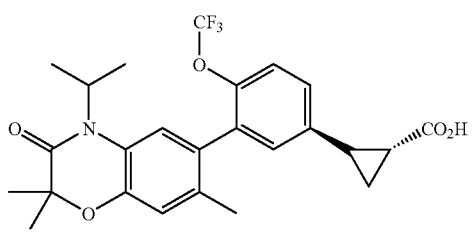

2-[3-(4-Isopropyl-2,2,7-trimethyl-3-oxo-3,4-dihydro-2H-benzo[1,4]oxazin-6-yl)-4-trifluoromethoxy-phenyl]-cyclopropanecarboxylic acid (Compound 23)

This compound was synthesized as a mixture of diastereomers from the t-butyl ester of Compound 4 using a procedure similar to that described in Example 19. MS (electrospray): mass calculated for $C_{25}H_{26}F_3NO_5$, 477.18; m/z found 478 $[M+H]^+$.

Example 24

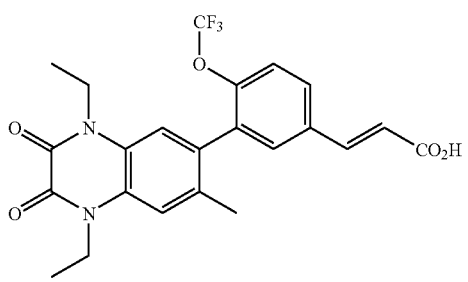

3-[3-(1,4-Diethyl-7-methyl-2,3-dioxo-1,2,3,4-tetrahydro-quinoxalin-6-yl)-4-trifluoromethoxy-phenyl]-acrylic acid (Compound 24)

A. 4-Bromo-5-methyl-benzene-1,2-diamine (Compound 24A)

To the solution of 4-methyl-2-nitro-phenylamine (1 g, 1 eq.) in 15 mL of acetic acid was added NBS (1.4 g, 1.2 eq.). The reaction was allowed to stir for 2.5 hours. Reaction was then diluted with 15 mL of water and Zn dust (1.29 g, 3 eq.) was added. Reaction was stirred for 1 hour, filtered and then pH was adjusted to ~7 with ammonia. The aqueous layer was extracted with $CH_2Cl_2$ twice, dried over $Na_2SO_4$, concentrated and adsorbed on silica. Purification by flash column chromatography (60:40 hexanes/EtOAc) afforded 1.1 g (83 %) of product as off-white solid. MS (electrospray): mass calculated for $C_7H_9BrN_2$, 201.06; m/z found 202.2, $[M+H]^+$.

B. 6-Bromo-1,4-diethyl-7-methyl-1,4-dihydro-quinoxaline-2,3-dione (Compound 24B)

Compound 24A (160 mg) in 1 mL of diethyl oxalate was heated in microwave at 140° C. for 30 min. Reaction was then cooled to rt, diluted with hexanes and resulting dark brown solid (164 mg, 81%) was collected by filtration.

Solution of above intermediate (164 mg, 1 eq.) and ethyl iodide (0.52 mL, 10 eq.) in 3 mL of anhydrous DMSO was cooled on ice and crushed into powder KOH (144 mg, 4.0 eq.) was added slowly. Reaction was stirred on ice for 1 hour and at rt for another hour. Reaction was then partitioned between $CH_2Cl_2$ and water. The organic layer was separated, dried over $Na_2SO_4$, filtered and the solvent was removed in vacuo. Crude was purified by column chromatography (40:60 hexane/EtOAc) to obtain 157 mg (78 %) of product. MS (electrospray): mass calculated for $C_{13}H_{15}BrN_2O_2$, 311.17; m/z found 312.2, $[M+H]^+$.

C. 3-[3-(1,4-Diethyl-7-methyl-2,3-dioxo-1,2,3,4-tetrahydroquinoxalin-6-yl)-4-trifluoromethoxy-phenyl]-acrylic acid (Compound 24)

Compound 24 was made from Compound 24B using a procedure similar to that described in Example 1, Steps D-F. MS (electrospray): mass calculated for $C_{23}H_{21}F_3N_2O_5$, 462.42; m/z found 463.3, $[M+H]^+$.

Example 25

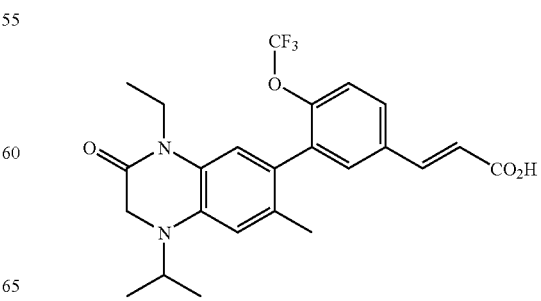

3-[3-(4-Ethyl-1-isopropyl-7-methyl-3-oxo-1,2,3,4-tetrahydro-quinoxalin-6-yl)-4-trifluoromethoxy-phenyl]-acrylic acid (Compound 25)

A. Isopropyl-(5-methyl-2-nitro-phenly)-amine (Compound 25A)

A solution of 3-fluoro-4-nitro toluene (5.25 g, 33.9 mmol) and isopropyl amine (2.9 mL, 67.7 mmol) in 110 mL of dichloroethane is heated to 80° C. for overnight After the reaction cooled to room temperature the mixture was poured into 50 mL of water and extracted with dichloromethane (3×50 mL). The combined organic layers were washed with brine, dried over sodium sulfate, filtered and excess solvent removed via rotary evaporator. The product was used without further purification. MS (electrospray): mass calculated for $C_{10}H_{12}N_2O_4$, 224.08; m/z found 225.1, $[M+H]^+$.

B. $N^2$-Isopropyl-4-methyl-benzene-1,2-diamine (Compound 25B)

Compound 25A (33.9 mmol) was dissolved in 200 mL of ethanol and treated with a catalytic amount (400 mg) of 5% palladium on carbon and ammonium formate (5.04 g, 80 mmol). The reaction mixture was then stirred at room temperature for 4 hours. The reaction mixture was then filtered and excess solvent removed on the rotary evaporator. The crude product was re-dissolved in 10 mL dichloromethane and any solids were filtered off. The DCM solution was then evaporated to yield product as a brown oil which was used without further purification. MS (electrospray): mass calculated for $C_{10}H_{16}N_2$, 164.13; m/z found 165.1, $[M+H]^+$.

C. 4-Isopropyl-6-methyl-3,4-dihydro-1H-quinoxalin-2-one (Compound 25C)

Compound 25B (2.17 g, 13.2 mmol) in 40 mL of dichloromethane was treated with a premixed solution of 1,3-dicyclohexylcarbodiimide (3 g, 14.5 mmol) and bromoacetic acid (1.84 mg, 13.2 mmol) in 30 mL of dichloromethane. The reaction was stirred for 1 hour and then quenched with 50 mL of water and extracted with dichloromethane (3×50 mL). The combined organic layers were washed with brine, dried over sodium sulfate, filtered and excess solvent removed via rotary evaporator. The crude product was then dissolved in 30 mL of DMSO and potassium carbonate (2.27 g, 16.5 mmol) was added to the mixture. The reaction was heated to 60° C. overnight then cooled and poured oven ice water. The resulting precipitate was collected be filtration to give 200 mg (7%) of desired product. MS (electrospray): mass calculated for $C_{12}H_{16}N_2O$, 204.13; m/z found 205.1, $[M+H]^+$.

D. 3-[3-(4-Ethyl-1-isopropyl-7-methyl-3-oxo-1,2,3,4-tetrahydro-quinoxalin-6-yl)-4-trifluoromethoxy-phenyl]-acrylic acid (Compound 25)

Compound 25 was made from Compound 25C using a procedure similar to that described in Example 1, Steps B-F. MS (electrospray): mass calculated for $C_{24}H_{25}F_3N_2O_4$, 462.18; m/z found 463.2, $[M+H]^+$.

Example 26

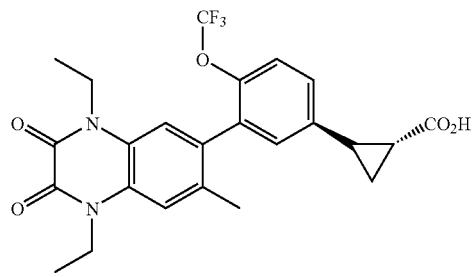

2-[3-(1,4-Diethyl-7-methyl-2,3-dioxo-1,2,3,4-tetrahydro-quinoxalin-6-yl)-4-trifluoromethoxy-phenyl]-cyclopropanecarboxylic acid (Compound 26)

This compound was synthesized as a mixture of diastereomers from the t-butyl ester of Compound 24 using a procedure similar to that described in Example 19. MS (electrospray): mass calculated for $C_{24}H_{23}F_3N_2O_5$, 476.45; m/z found 477.3, $[M+H]^+$.

Example 27

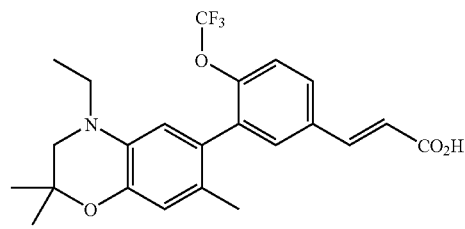

3-[3-(4-Ethyl-2,2,7-trimethyl-3,4-dihydro-2H-benzo[1,4]oxazin-6-yl)-4-trifluoromethoxy-phenyl]-acrylic acid (Compound 27)

A. 6-Bromo-4-ethyl-2,2,7-trimethyl-3,4-dihydro-2H-benzo[1,4,]oxazine (Compound 27A)

A solution of Compound 1C (250 mg, 0.84 mmol) is dissolved in 5 mL of dry THF. To this was added 0.25 mL of a 10 M solution of a borane-methyl sulfide complex. The reaction was refluxed for 2 hours, cooled and quenched with the slow addition of 5 mL of methanol. This was allowed to stir for 4 hours before the solvent was removed in vaccu. The crude compound was purified by flash chromatography (100% hexanes) to yield 244 mg of product (100%). MS (electrospray): mass calculated for $C_{13}H_{18}BrNO$, 283.06; m/z found 284.1 $[M+H]^+$.

B. 3-[3-(4-Ethyl-2,2,7-trimethyl-3,4-dihydro-2H-benzo[1,4]oxazin-6-yl)-4-trifluoromethoxy-phenyl]-acrylic acid (Compound 27)

This was made from Compound 27A using a procedure similar to that described for Compound 1. MS (electrospray): mass calculated for $C_{23}H_{24}F_3NO_4$, 435.17; m/z found 436.2, $[M+H]^+$.

D) General Administration, Formulation, and Dosages

The present compounds are RXR agonists and are therefore useful in treating, preventing, or inhibiting the progression of RXR mediated conditions, such as metabolic disorders including diabetes, dyslipidemia, hypercholesterolemia, and associated symptoms or complications thereof, as well as various cancerous and precancerous conditions in the breast, skin, prostate, cervix, uterus, colon, bladder, esophagus, stomach, lung, larynx, oral cavity, blood and/or lymphatic systems.

The invention features a method for treating a subject with a RXR mediated disease, said method comprising administering to the subject a therapeutically effective amount of a pharmaceutical composition comprising a compound of the invention. The invention also provides a method for treating or inhibiting the progression of diabetes, dyslipidemia, hypercholesterolemia, and associated symptoms or complications thereof in a subject, wherein the method comprises administering to the subject a therapeutically effective amount of a pharmaceutical composition comprising a compound of the invention.

Pharmaceutically acceptable salts include the therapeutically active non-toxic salts of disclosed compounds. The latter can conveniently be obtained by treating the base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, palmoic and the like acids. The term salt also comprises the solvates which the disclosed compounds, as well as the salts thereof, are able to form. Such solvates are for example hydrates, alcoholates and the like. Conversely the salt form can be converted by treatment with alkali into the free base form.

Stereoisomeric forms define all the possible isomeric forms which the compounds of the invention may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the (R)- or (S)-configuration; substituents on bivalent cyclic saturated radicals may have either the cis- or trans-configuration. The invention encompasses stereochemically isomeric forms including diastereoisomers, as well as mixtures thereof in any proportion of the disclosed compounds. The disclosed compounds may also exist in their tautomeric forms. Such forms although not explicitly indicated in the above and following formulae are intended to be included within the scope of the present invention.

The next section includes detailed information relating to the use of the disclosed compounds and compositions.

E) Use

The compounds of the present invention are pharmaceutically active, for example, as RXR agonists. According to one aspect of the invention, the compounds are preferably selective RXR agonists.

Examples of RXR-mediated diseases include IDDM, NIDDM, IGT, IFG, Syndrome X (or Metabolic Syndrome), insulin resistance, obesity, hyperlipidemia (including, phase I hyperlipidemia, pre-clinical hyperlipidemia, and phase II hyperlipidemia), hypercholesteremia, hypertriglyceridemia, insulin resistance, dyslipidemia, nephropathy, neuropathy, retinopathy, atherosclerosis, low HDL, non-alcoholic steatohepatitis, polycystic ovary syndrome or polycystic ovarian syndrome, hypertension, ischemia, stroke, high blood pressure, heart disease (e.g., acute coronary syndromes or ACS, including but not limited to, non-ST segment myocardial infarction and ST-segment elevation myocardial infarctions), irritable bowel disorder, inflammation, cardiovascular disorders and cataracts According to one aspect of the invention, the disclosed compounds and compositions are useful for the amelioration of symptoms associated with, the treatment of, and the prevention of, the following conditions and diseases: phase I hyperlipidemia, pre-clinical hyperlipidemia, phase II hyperlipidemia, hypercholesteremia, hypertriglyceridemia, diabetes, insulin resistance, impaired glucose tolerance, dyslipidemia, and cardiovascular disorders. Preferred compounds of the invention are useful in lowering serum levels of low-density lipoproteins (LDL), intermediate density lipoprotein (IDL), and/or small LDL and other atherogenic molecules, or molecules that cause atherosclerotic complications, thereby reducing cardiovascular disorders and/or complications thereof. Preferred compounds are also useful in elevating serum levels of high-density lipoproteins (HDL), as well as in lowering serum levels of triglycerides and/or free fatty acids.

According to one aspect of the invention, the disclosed compounds may be used in a method for treating or inhibiting the progression of an RXR mediated condition and, optionally, an additional Retinoid A Receptor mediated condition, said method comprising administering to a patient in need of treatment a pharmaceutically effective amount of a composition of the invention.

Another aspect of the invention is a method of use wherein the RXR mediated condition is acute coronary syndromes such as non-ST segment myocardial infarction and ST-segment elevation myocardial infarctions.

A further aspect of the invention is a method for treating at least one RXR mediated condition and at least one Retinoid A Receptor mediated condition in a patient, said method comprising administering to a patient in need of treatment a pharmaceutically effective amount of a composition of the invention.

The invention also features pharmaceutical compositions which include, without limitation, one or more of the disclosed compounds, and pharmaceutically acceptable carriers or excipients.

1. Dosages

Those of skill in the treatment of disorders or conditions mediated by RXR could easily determine the effective daily amount from the test results presented hereinafter and other information. The exact dosage and frequency of administration depends on the particular compound of invention used, the particular condition being treated, the severity of the condition being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned herein are therefore only guidelines in practicing the present invention.

The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg/kg to about 300 mg/kg (preferably from about 0.01 mg/kg to about 100 mg/kg; and, more preferably, from about 0.01 mg/kg to about 30 mg/kg) and may be given at a dosage of from about 0.01 mg/kg/day to about 300 mg/kg/day (preferably from about 0.01 mg/kg/day to about 100 mg/kg/day and more preferably from about 0.01 mg/kg/day to about 30 mg/kg/day). Preferably, the method for the treatment of metabolic disorders described in the present invention using any of the compounds as defined herein, the dosage form will contain a pharmaceutically acceptable carrier containing between from about 0.01 mg to about 100 mg; and, more preferably, from about 5 mg to about 50 mg of the compound, and may be constituted into any form suitable for the mode of administration selected. The dosages, however, may be varied depending upon the requirement of the subjects, the severity of the condition being treated and the compound being employed, The use of either daily administration or post-periodic dosing may be employed.

Preferably these compositions are in unit dosage forms from such as tablets, pills, capsules, dry powders for reconstitution or inhalation, granules, lozenges, sterile parenteral solutions or suspensions, metered aerosol or liquid sprays, drops, ampoules, autoinjector devices or suppositories for administration by oral, intranasal, sublingual, intraocular, transdermal, parenteral, rectal, vaginal, dry powder inhaler or other inhalation or insufflation means. Alternatively, the composition may be presented in a form suitable for once-weekly or once-monthly administration; for example, an insoluble salt of the active compound, such as the decanoate salt, may be adapted to provide a depot preparation for intramuscular injection.

For preparing solid pharmaceutical compositions such as tablets, the principal active ingredient is mixed with a pharmaceutical carrier, e.g. conventional tableting ingredients such as diluents, binders, adhesives, disintegrants, lubricants, antiadherents and gildants. Suitable diluents include, but are not limited to, starch (i.e. corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e. AVICEL™ microcrystalline cellulose available from FMC Corp.), dicalcium phosphate, calcium sulfate dihydrate, calcium lactate trihydrate and the like. Suitable binders and adhesives include, but are not limited to acacia gum, guar gum, tragacanth gum, sucrose, gelatin, glucose, starch, and cellulosics (i.e. methylcellulose, sodium carboxymethylcellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose [i.e. TYLOSE™ available from Hoechst Celanese], polyethylene glycol, polysaccharide acids, bentonites, polyvinylpyrrolidone, polymethacrylates and pregelatinized starch) and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e. corn starch, etc.), gums (i.e. agar, guar, locust bean, karaya, pectin, and tragacanth gum), crosslinked polyvinylpyrrolidone and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable gildants include, but are not limited to, talc, cornstarch, silica (i.e. CAB-O-SIL™ silica available from Cabot, SYLOID™ silica available from W. R. Grace/Davison, and AEROSIL™ silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

Generally these carriers are mixed with the pharmaceutical active to form a solid preformulation composition containing a homogeneous mixture of the pharmaceutical active of the present invention, or a pharmaceutically acceptable salt thereof. Generally the preformulation will be formed by one of three common methods: (a) wet granulation, (b) dry granulation and (c) dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.1 mg to about 500 mg of the active ingredient of the present invention. The tablets or pills containing the novel compositions may also be formulated in multilayer tablets or pills to provide a sustained or provide dual-release products For example, a dual release tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate (i.e. cellulose acetate phthalate, cellulose acetate trimetilitate), polyvinyl acetate phthalate, hydroxypropyl methylcellulose phthalate, hydroxypropyl methylcellulose acetate succinate, methacrylate and ethylacrylate copolymers, methacrylate and methyl methacrylate copolymers and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient) These materials include natural and synthetic polymers waxes, hydrogenated oils, fatty acids and alcohols (i.e. beeswax, carnauba wax, cetyl alcohol, cetylstearyl alcohol, and the like), esters of fatty acids metallic soaps, and other acceptable materials that can be used to granulate, coat, entrap or otherwise limit the solubility of an active ingredient to achieve a prolonged or sustained release product.

The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable suspending agents for aqueous suspensions, include synthetic and natural gums such as, acacia, agar, alginate (i.e. propylene alginate, sodium alginate and the like), guar, karaya, locust bean, pectin, tragacanth, and xanthan gum, cellulosics such as sodium carboxymethylcellulose, methylcellulose, hydroxymethylcellulose, hydroxyethylcellulose, hydroxypropyl cellulose and hydroxypropyl methylcellulose, and combinations thereof, synthetic polymers such as polyvinyl pyrrolidone, carbomer (i.e. carboxypolymethylene), and polyethylene glycol; clays such as bentonite, hectorite, attapulgite or sepiolite; and other pharmaceutically acceptable suspending agents such as lecithin, gelatin or the like, Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235 and combinations thereof. Suitable deflocculating or dispersing agent include pharmaceutical grade lecithins. Suitable flocculating agent include but are not limited to simple neutral electrolytes (i.e. sodium chloride, potassium, chloride, and the like), highly charged insoluble polymers and polyelectrolyte species, water soluble divalent or trivalent ions (i.e. calcium salts, alums or sulfates, citrates and phosphates (which can be used jointly in formulations as pH buffers and flocculating agents). Suitable preservatives include but are not limited to parabens (i.e. methyl, ethyl, n-propyl and n-butyl), sorbic acid, thimerosal, quaternary ammonium salts, benzyl alcohol, benzoic acid, chlorhexidine gluconate, phenylethanol and the like. There are many liquid vehicles that may be used in liquid pharmaceutical dosage forms, however, the liquid vehicle that is used in a particular dosage form must be compatible with the suspending agent(s). For example, nonpolar liquid vehicles such as fatty esters and oils liquid vehicles are best used with suspending agents such as low HLB (Hydrophile-Lipophile Balance) surfactants, stearalkonium hectorite, water insoluble resins, water insoluble film forming polymers and the like. Conversely, polar liquids such as water, alcohols, polyols and glycols are best used with suspending agents such as higher HLB surfactants, clays silicates, gums, water soluble cellulosics, water soluble polymers and the like. For parenteral administration, sterile suspensions and solutions are desired. Liquid forms useful for parenteral administration include sterile solutions, emulsions and suspensions. Isotonic preparations which generally contain suitable preservatives are employed when intravenous administration is desired.

Furthermore, compounds of the present invention can be administered in an intranasal dosage form via topical use of suitable intranasal vehicles or via transdermal skin patches, the composition of which are well known to those of ordinary skill in that art. To be administered in the form of a transdermal delivery system, the administration of a therapeutic dose will, of course, be continuous rather than intermittent throughout the dosage regimen.

Compounds of the present invention can also be administered in the form of liposome delivery systems, such as small unilamellar vesicles, large unilamellar vesicles, multilamellar vesicles and the like. Liposomes can be formed from a variety of phospholipids, such as cholesterol, stearylamine, phosphatidylcholines and the like.

Compounds of this invention may be administered in any of the foregoing compositions and dosage regimens or by means of those compositions and dosage regimens established in the art whenever treatment of RXR mediated disorders is required for a subject in need thereof.

The daily dose of a pharmaceutical composition of the present invention may be varied over a wide range from about 0.7 mg to about 500 mg per adult human per day; preferably, the dose will be in the range of from about 0.7 mg to about 100 mg per adult human per day; most preferably the dose will be in the range of from about 0.7 mg to about 50 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated. An effective amount of the drug is ordinarily supplied at a dosage level of from about 0.01 mg/kg to about 300 mg/kg of body weight per day. Advantageously, a compound of the present invention may be administered in a single daily dose or the total daily dosage may be administered in divided doses of two, three or four times daily.

Optimal dosages to be administered may be readily determined by those skilled in the art, and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level.

2. Formulations

To prepare the pharmaceutical compositions of this invention, one or more compounds of Formula (I) or salt thereof as the active ingredient, is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

The compounds of the present invention may be formulated into various pharmaceutical forms for administration purposes. Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

3. Combination Therapy

The compounds of the present invention may be used in combination with one or more pharmaceutically active agents. These agents include other RXR modulators, other RAR modulators, other anti-diabetic agents, other lipid lowering agents, as well as blood pressure lowering agents such as statin drugs and the fibrates.

Other RXR modulators include, but are not limited to:
(1) bexarotene (4-(1-(3,5,5,8,8-pentamethyl-5,6,7,8-tetrahydro-2-naphthalenyl)ethenyl)benzoic acid, known as TARGRETIN, TARGRETYN, TARGREXIN; also known as LGD 1069, LG 100069, LG 1069, LDG 1069, LG 69, RO 264455);
(2) 9-cis-retinoic acid;
(3) AGN-4326 (also known as ALRT-4204, AGN-4204, ALRT-326, ALRT-324, or LGD 1324);
(4) LGD 1324 (ALRT 324);
(5) LG 100754;
(6) LY-510929;
(7) LGD 1268 (6-(1,1,4,4,6-pentamethyl-1,2,3,4-tetrahydro-naphth-7-ylcycloprop-1-yl) nicotinic acid, known as ALRT 268 or LG 100268);

(8) LG 100264; and
(9) substituted heterocycles as disclosed in PCT publications WO 01/16122 and WO 01/16123 by Maxia, One preferred example of substituted heterocycles is MX-6054, which is 2,4-thiazolidinedione, 5-[[3-(5,6,7,8-tetrahydro-3,5,5,8,8-pentamethyl-2-naphthalenyl)-4-(trifluoromethoxy)phenyl]methylene]-, (5Z)-, also named 3-(3,5,5,8,8-pentamethyl-5,6,7,8-tetrahydro-2-naphthyl)-4-trifluoromethoxybenzylidene-2,4-thiazolidinedione, reperesented by the following formula:

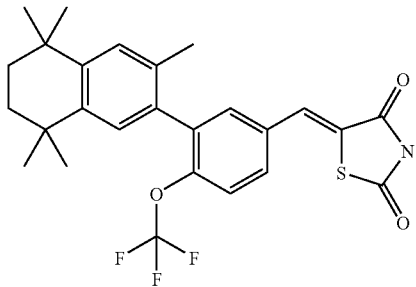

Another preferred example of substituted heterocycles is 2,4-thiazolidinedione, 5-[[3-(1-ethyl-1,2,3,4-tetrahydro-4,4,6-trimethyl-2-oxo-7-quinolinyl)-4-(trifluoromethoxy)phenyl]methylene]-, (5Z)-, reperesented by the following formula:

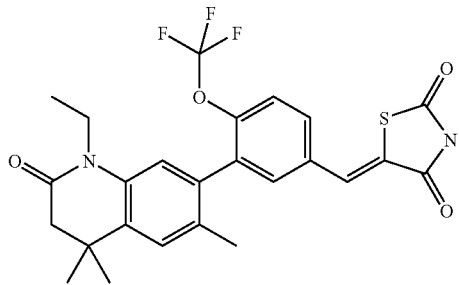

Preferred substituted heterocycles are selected from:
3-(3,5,5,8,8-pentamethyl-5,6,7,8-tetrahydro-2-naphthyl)-4-trifluoromethoxybenzylidene-2,4-thiazolidinedione;
4-[2-(3,5,5,8,8-pentamethyl-5,6,7,8-tetrahydro-2-naphthyl)-1,3-dioxolane]benzylidene-2,4-thiazolidinedione;
4-[2-(5,5,8,8tetramethyl-5,6,7,8-tetrahydro-2-naphthyl)-2-propyl]benzylidene-2,4-thiazolidinedione;
4-[2-(3,5,5,8,8-pentamethyl-5,6,7,8-tetrahydro-2-naphthyl)-1,3-dioxolane]benzylidene-2-thioxo-2,4-thiazolidinedione;
4-[2-(5,5,8,8-tetramethyl-5,6,7,8-tetrahydro-2-naphthyl)-2-propyl]benzylidene-2-thioxo-2,4-thiazolidinedione;
4-[2-(3,5,5,8,8-pentamethyl-5,6,7,8-tetrahydro-2-naphthyl)-1,3-dioxolane]benzylidene-2-thioxo-2,4-imidazolidinedione;
4-[2-(5,5,8,8-tetramethyl-5,6,7,8-tetrahydro-2-naphthyl)-2-propyl]benzylidene-2-thioxo-2,4-imidazolidinedione;
4-[2-(3,5,5,8,8-pentamethyl-5,6,7,8-tetrahydro-2-naphthyl)-1,3-dioxolane]benzylidene-2,4-imidazolidinedione;
4-[2-(5,5,8,8-tetramethyl-5,6,7,8-tetrahydro-2-naphthyl)-2-propyl]benzylidene-2,4-imidazolidinedione;
4-[2-(3,5,5,8,8-pentamethyl-5,6,7,8-tetrahydro-2-naphthyl)-1,3-dioxolane]benzyl-2,4-thiazolidinedione;
4-[2-(5,5,8,8-tetramethyl-5,6,7,8-tetrahydro-2-naphthyl)-2-propyl]benzyl-2,4-thiazolidinedione;
4-[2-(3,5,5,8,8-pentamethyl-5,6,7,8-tetrahydro-2-naphthyl)-1,3-dioxolane]benzyl-2-thioxo-2,4-thiazolidinedione;
4-[2-(5,5,8,8-tetramethyl-5,6,7,8-tetrahydro-2-naphthyl)-2-propyl]benzyl-2-thioxo-2,4-thiazolidinedione;
4-[2-(3,5,5,8,8-pentamethyl-5,6,7,8-tetrahydro-2-naphthyl)-1,3-dioxolane]benzyl-2-thioxo-2,4-imidazolidinedione;
4-[2-(5,5,8,8-tetramethyl-5,6,7,8-tetrahydro-2-naphthyl)-2-propyl]benzyl-2-thioxo-2,4-imidazolidinedione;
4-[2-(3,5,5,8,8-pentamethyl-5,6,7,8-tetrahydro-2-naphthyl)-1,3-dioxolane]benzyl-2,4-imidazolidinedione; and
4-[2-(5,5,8,8-tetramethyl-5,6,7,8-tetrahydro-2-naphthyl)-2-propyl]benzyl-2,4-imidazolidinedione.

Other anti-diabetic agents include thiazolidinedione and non-thiazolidinedione insulin sensitizers, which decrease peripheral insulin resistance by enhancing the effects of insulin at target organs and tissues.

The following agents are known to bind and activate the nuclear receptor peroxisome proliferator-activated receptor-gamma (PPARfγ) which increases transcription of specific insulin-responsive genes, Examples of PPAR-gamma agonists are thiazolidinediones such as:

(1) rosiglitazone (2,4-thiazolidinedione,5-((4-(2-(methyl-2-pyridinylamino)ethoxy)phenyl)methyl)-, (Z)-2-butenedioate (1:1) or 5-((4-(2-(methyl-2-pyridinylamino)ethoxy)phenyl)methyl)-2,4-thiazolidinedione, known as AVANDIA; also known as BRL 49653, BRL 49653C, BRL 49653c, SB 210232, or rosiglitazone maleate);

(2) pioglitazone (2,4-thiazolidinedione, 5-((4-(2-(5-ethyl-2-pyridinyl)ethoxy)phenyl)methyl)-, monohydrochioride, (+-)- or 5-((4-(2-(5-ethyl-2-pyridyl)ethoxy)phenyl)methy)-2,4-thiazolidinedione, known as ACTOS, ZACTOS, or GLUSTIN; also known as AD 4833, U 72107, U 72107A, U 72107E, pioglitazone hydrochloride (USAN));

(3) troglitazone (5-((4-((3,4-dihydro-6-hydroxy-2,5,7,8-tetramethyl-2H-1-benzopyran-2-yl) methoxy)phenyl) methyl)-2,4-thiazolidinedione, known as NOSCAL, REZULIN, ROMOZIN, or PRELAY; also known as Cl 991, CS 045, GR 92132, GR 92132X);

(4) isaglitazone ((+)-5-[[6-[(2-fluorophenyl)methoxy]-2-naphthalenyl]methyl]-2,4-thiazolidinedione or 5-((6-((2-fluorophenyl)methoxy)-2-naphthalenyl)methyl-2,4-thiazolidinedione or 5-(6-(2-fluorobenzyloxy) naphthalen-2-ylmethyl)thiazolidine-2,4-dione, also known as MCC-555 or neoglitazone); and (5) 5-BTZD.

Additionally, the non-thiazolidinediones that act as insulin sensitizing agents include, but are not limited to:

(1) JT-501 (JTT 501, PNU-1827, PNU-716-MET-0096, or PNU 182716: isoxazolidine-3,5-dione,4-((4-(2-phenyl-5-methyl)-1,3-oxazolyl)ethylphenyl-4)methyl-);

(2) KRP-297 (5-(2,4-dioxothiazolidin-5-ylmethyl)-2-methoxy-N-(4-(trifluoromethyl)benzyl)benzamide or 5-((2,4-dioxo-5-thiazolidinyl)methyl)-2-methoxy-N-((4-(trifluoromethyl)phenyl)methyl)benzamide); and (3) Farglitazar (L-tyrosine, N-(2-benzoylphenyl)-o-(2-(5-methyl-2-phenyl-4-oxazolyl)ethyl)- or N-(2-benzoylphenyl)-O-(2-(5-methyl-2-phenyl-4-oxazolyl) ethyl)-L-tyrosine, or GW2570 or GI-262570).

Other anti-diabetic agents have also been shown to have PPAR modulator activity such as PPAR gamma, SPPAR gamma, and/or PPAR delta/gamma agonist activity. Examples are listed below:

(1) AD 5075;
(2) R 119702((+−)-5-(4-(5-Methoxy-1H-benzimidazol-2-ylmethoxy)benzyl)thiazolin-2,4-dione hydrochloride, or CI 1037 or CS 011);
(3) CLX-0940 (peroxisome proliferator-activated receptor alpha agonist/peroxisome proliferator-activated receptor gamma agonist);
(4) LR-90 (2,5,5-tris(4-chlorophenyl)-1,3-dioxane-2-carboxylic acid, PPARdelta/γ agonist);
(5) Tularik (PPARγ agonist);
(6) CLX-0921 (PPARγ agonist);
(7) CGP-52608 (PPAR agonist);
(8) GW-409890 (PPAR agonist);
(9) GW-7845 (PPAR agonist);
(10) L-764406 (PPAR agonist);
(11) LG-101280 (PPAR agonist);
(12) LM-4156 (PPAR agonist);
(13) Risarestat (CT-112);
(14) YM 440 (PPAR agonist);
(15) AR-H049020 (PPAR agonist);
(16) GW 0072 (4-(4-((2S,5S)-5-(2-(bis(phenylmethyl)amino)-2-oxoethyl)-2-heptyl-4-oxo-3-thiazo lidinyl)butyl)benzoic acid);
(17) GW 409544 (GW-544 or GW-409544);
(18) NN 2344 (DRF 2593);
(19) NN 622 (DRF 2725);
(20) AR-H039242 (AZ-242);
(21) GW 9820 (fibrate);
(22) GW 1929 (N-(2-benzoylphenyl)-O-(2-(methyl-2-pyridinylamino)ethyl)-L-tyrosine, known as GW 2331, PPAR alpha/γ agonist);
(23) SB 219994 ((S)-4-(2-(2-benzoxazolylmethylamino)ethoxy)-alpha-(2,2,2-trifluoroethoxy)benzenepropanoic acid or 3-(4-(2-(N-(2-benzoxazolyl)-N-methylamino)ethoxy)phenyl)-2(S)-(2,2,2-trifluoroethoxy) propionic acid or benzenepropanoic acid,4-(2-(2-benzoxazolylmethylamino)ethoxy)-alpha-(2,2,2-trifluoroethoxy)-, (alphaS)-, PPARalpha/γ agonist);
(24) L-796449 (PPAR alpha/γ agonist);
(25) Fenofibrate (Propanoic acid, 2-[4-(4-chlorobenzoyl)phenoxy]-2-methyl-, 1-methylethyl ester, known as TRICOR, LIPCOR, LIPANTIL, LIPIDIL MICRO PPAR alpha agonist);
(26) GW-9578 (PPAR alpha agonist);
(27) GW-2433 (PPAR alpha/γ agonist);
(28) GW-0207 (PPARγ agonist);
(29) LG-100641 (PPARγ agonist);
(30) LY-300512 (PPARγ agonist);
(31) NID525-209 (NID-525);
(32) VDO-52 (VDO-52);
(33) LG 100754 (peroxisome proliferator-activated receptor agonist);
(34) LY-510929 (peroxisome proliferator-activated receptor agonist);
(35) bexarotene (4-(1-(3,5,5,8,8-pentamethyl-5,6,7,8-tetrahydro -2-naphthalenyl)ethenyl)benzoic acid, known as TARGRETIN, TARGRETYN, TARGREXIN; also known as LOD 1069, LG 100069, LG 1069, LDG 1069, LG 69, RO 264455); and (36) GW-1536 (PPAR alpha/γ agonist).

Other insulin sensitizing agents include, but are not limited to:
(1) INS-1 (D-chiro inositol or D -1, 2, 3, 4, 5, 6-hexahydroxycyclohexane);
(2) protein tyrosine phosphatase 1 B (PTP-1B) inhibitors;
(3) glycogen synthase kinase-3 (GSK3) inhibitors;
(4) beta 3 adrenoceptor agonists such as ZD 2079 ((R)-N-(2-(4-(carboxymethyl)phenoxy)ethyl)-N-(2-hydroxy-2-phenethyl)ammonium chloride, also known as ICI D 2079) or AZ 40140;
(5) glycogen phosphorylase inhibitors;
(6) fructose-1,6-bisphosphatase inhibitors;
(7) chromic picolinate, vanadyl sulfate (vanadium oxysulfate);
(8) KP 102 (organo-vanadium compound);
(9) chromic polynicotinate;
(10) potassium channel agonist NN 414;
(11) YM 268 (5,5'-methylene-bis(1,4-phenylene)bismethylenebis(thiazolidine-2,4-dione);
(12) TS 971;
(13) T 174 ((+−)-5-(2,4-dioxothiazolidin-5-ylmethyl)-2-(2-naphthylmethyl)benzoxazole);
(14) SDZ PGU 693 ((+)-trans-2(S-((4-chlorophenoxy)methyl)-7alpha-(3,4-dichlorophenyl)tetrahydropyrrolo(2,1-b)oxazol-5(6H)-one);
(15) S 15261 ((−)-4-(2-((9H-fluoren-9-ylacetyl)amino)ethyl)benzoic acid 2-((2-methoxy-2-(3-(trifluoromethyl)phenyl)ethyl)amino)ethyl ester);
(16) AZM 134 (Alizyme);
(17) ARIAD;
(18) R 102380;
(19) PNU 140975 (1-(hydrazinoiminomethyl)hydrazino) acetic acid;
(20) PNU 106817 (2-(hydrazinoiminomethyl)hydrazino) acetic acid;
(21) NC 2100 (5-((7-(phenylmethoxy)-3-quinolinyl)methyl)-2,4-thiazolidinedione;
(22) MXC 3255;
(23) MBX 102;
(24) ALT 4037;
(25) AM 454;
(26) JTP 20993 (2-(4-(2-(5-methyl-2-phenyl-4-oxazolyl)ethoxy)benzyl)-malonic acid dimethyl diester);
(27) Dexlipotam (5 (R)-(1,2-dithiolan-3-yl)pentanoic acid, also known as (R)-alpha lipoic acid or (R)-thioctic acid);
(28) BM 170744 (2,2-Dichloro -12-(p-chlorophenyl)dodecanoic acid);
(29) BM 152054 (5-(4-(2-(5-methyl -2-(2-thienyl)oxazol-4-yl)ethoxy)benzothien-7-ylmethyl)thiazolidine-2,4-dione);
(30) BM 131258 (5-(4-(2-(5-methyl-2-phenyloxazol-4-yl)ethoxy)benzothien-7-ylmethyl)thiazolidine-2,4-dione);
(31) CRE 16336 (EML 16336);
(32) HQL 975 (3-(4-(2-(5-methyl-2-phenyloxazol-4-yl)ethoxy)phenyl)-2 (S)-(propylamino)propionic acid);
(33) DRF 2189 (5-((4-(2-(1-Indolyl)ethoxy)phenyl)methyl)thiazolidine-2,4-dione);
(34) DRF 554158;
(35) DRF-NPCC;
(36) CLX 0100, CLX 0101, CLX 0900, or CLX 0901;
(37) IkappaB Kinase (IKK B) Inhibitors
(38) mitogen-activated protein kinase (MAPK) inhibitors p38 MAPK Stimulators
(39) phosphatidyl-inositide triphosphate
(40) insulin recycling receptor inhibitors
(41) glucose transporter 4 modulators

(42) TNF-α antagonists
(43) plasma cell differentiation antigen-1 (PC-1) Antagonists
(44) adipocyte lipid-binding protein (ALBP/aP2) inhibitors
(45) phosphoglycans
(46) Galparan;
(47) Receptron;
(48) islet cell maturation factor;
(49) insulin potentiating factor (IPF or insulin potentiating factor-1);
(50) somatomedin C coupled with binding protein (also known as IGF-BP3, IGF-BP3, SomatoKine);
(51) Diab II (known as V-411) or Glucanin, produced by Biotech Holdings Ltd. or Volque Pharmaceutical;
(52) glucose-6 phosphatase inhibitors;
(53) fatty acid glucose transport protein;
(54) glucocorticoid receptor antagonists; and
(55) glutamine:fructose-6-phosphate amidotransferase (GFAT) modulators.

Anti-diabetic agents also include biguanides, which decreases liver glucose production and increases the uptake of glucose. Examples of biguanides include metformin such as:
(1) 1,1-dimethylbiguanide (e.g., Metformin-DepoMed, Mefformin-Biovail Corporation, or METFORMIN GR (metformin gastric retention polymer)); and
(2) metformin hydrochloride (N,N-dimethylimidodicarbonimidic diamide monohydrochloride, also known as LA 6023, BMS 207150, GLUCOPHAGE, or GLUCOPHAGE XR.

Anti-diabetic agents also include alpha-glucosidase inhibitors, which inhibit alpha-glucosidase. Alpha-glucosidase converts fructose to glucose, thereby delaying the digestion of carbohydrates. The undigested carbohydrates are subsequently broken down in the gut, reducing the post-prandial glucose peak. Examples of alpha-glucosidase inhibitors include, but are not limited to:
(1) acarbose (D-glucose, O-4,6-dideoxy-4-(((1S-(1alpha, 4alpha,5beta,6alpha))-4,5,6-trihydroxy-3-(hydroxymethyl)-2-cyclohexen-1-yl) amino)-alpha-D-glucopyranosyl-(1-4)-O-alpha-D-glucopyranosyl-(1-4)-, also known as AG-5421, Bay-g-542, BAY-g-542, GLUCOBAY, PRECOSE, GLUCOR, PRANDASE, GLUMIDA, or ASCAROSE);
(2) Miglitol (3,4,5-piperidinetriol, 1-(2-hydroxyethyl)-2-(hydroxymethyl)-, (2R (2alpha, 3beta, 4alpha, 5beta))- or (2R,3R,4R,5S)-1-(2-hydroxyethyl)-2-(hydroxymethyl -3,4,5-piperidinetriol, also known as BAY 1099, BAY M 1099, BAY-M-1099, BAYGLITOL, DIASTABOL, GLYSET, MIGLIBAY, MITOLBAY, PLUMAROL);
(3) CKD-711 (0-4-deoxy-4-((2,3-epoxy-3-hydroxymethyl-4,5,6-trihydroxycyclohexane-1-yl)amino)-alpha-b-glucopyranosyl-(1-4)-alpha-D-glucopyranosyl-(1-4)-D-glucopyranose);
(4) emiglitate (4-(2-((2R,3R,4R,5S)-3,4,5-trihydroxy-2-(hydroxymethyl)-1-piperidinyl)ethoxy)benzoic acid ethyl ester, also known as BAY o 1248 or MKC 542);
(5) MOR 14 (3,4,5-piperidinetriol, 2-(hydroxymethyl)-1-methyl -, (2R-(2alpha,3beta,4alpha,5beta))-, also known as N-methyideoxynojirimycin or N-methylmoranoline); and (6) Voglibose (3,4-dideoxy-4-((2-hydroxy-1-(hydroxymethyl)ethyl)amino)-2-C-(hydroxymethyl)-D-epi-inositol or D-epi-Inositol,3,4-dideoxy -4-((2-hydroxy-1-(hydroxymethyl)ethyl)amino)-2-C-(hydroxymethyl)-, also known as A 71100, AO 128, BASEN, GLUSTAT, VOGLISTAT.

Anti-diabetic agents also include insulins such as regular or short-acting, intermediate-acting, and long-acting insulins, non-injectable or inhaled insulin, tissue selective insulin, glucophosphokinin (D-chiroinositol), insulin analogues such as insulin molecules with minor differences in the natural amino acid sequence and small molecule mimics of insulin (insulin mimetics), and endosome modulators. Examples include, but are not limited to:
(1) Biota;
(2) LP 100;
(3) (SP -5-21)-oxobis(1-pyrrolidinecarbodithioato-S,S') vanadium,
(4) insulin aspart (human insulin (28B-L-aspartic acid) or B28-Asp-insulin, also known as insulin X14, INA-X14, NOVORAPID, NOVOMIX, or NOVOLOG);
(5) insulin detemir (Human 29B-(N6-(1-oxotetradecyl)-L-lysine)-(1A-21 A), (1B -29B)-Insulin or NN 304);
(6) insulin lispro ("28B-L-lysine-29B-L-proline human insulin, or Lys(B28), Pro(B29) human insulin analog, also known as lys-pro insulin, LY 275585, HUMALOG, HUMALOG MIX 75/25, or HUMALOG MIX 50/50);
(7) insulin glargine (human (A21-glycine, B31-arginine, B32-arginine) insulin HOE 901, also known as LANTUS, OPTISULIN);
(8) Insulin Zinc Suspension, extended (Ultralente), also known as HUMULIN U or ULTRALENTE;
(9) Insulin Zinc suspension (Lente), a 70% crystalline and 30% amorphous insulin suspension, also known as LENTE ILETIN II, HUMULIN L, or NOVOLIN L;
(10) HUMULIN 50/50 (50% isophane insulin and 50% insulin injection);
(11) HUMULIN 70/30 (70% isophane insulin NPH and 30% insulin injection), also known as NOVOLIN 70/30, NOVOLIN 70/30 PenFill, NOVOLIN 70/30 Prefilled;
(12) insulin isophane suspension such as NPH ILETIN II, NOVOLIN N, NOVOLIN N PenFill, NOVOLIN N Prefilled, HUMULIN N.
(13) regular insulin injection such as ILETIN II Regular, NOVOLIN R, VELOSULIN BR, NOVOLIN R PenFill, NOVOLIN R Prefilled, HUMULIN R, or Regular U-500 (Concentrated);
(14) ARIAD;
(15) LY 197535;
(16) L-783281; and
(17) TE-17411.

Anti-diabetic agents also include insulin secretion modulators such as:
(1) glucagon-like peptide-1 (GLP-1) and its mimetics;
(2) glucose-insulinotropic peptide (GIP) and its mimetics;
(3) exendin and its mimetics;
(4) dipeptyl protease (DPP or DPPIV) inhibitors such as
(4a) DPP-728 or LAF 237 (2-pyrrolidinecarbonitrile,1-(((2-((5-cyano-2-pyridinyl)amino)ethyl)amino) acetyl), known as NVP-DPP-728, DPP-728A, LAF-237);
(4b) P 3298 or P32/98 (di-(3N-((2S, 3S)-2-amino-3-methyl-pentanoyl)-1,3-thiazolidine)fumarate);
(4c) TSL 225 (tryptophyl-1,2,3,4-tetrahydroisoquinoline-3-carboxylic acid);
(4d) Valine pyrrolidide (valpyr), (4e) 1-aminoalkylisoquinolinone-4-carboxylates and analogues thereof;
(4f) SDZ 272-070 (1-(L-Valyl)pyrrolidine);
(4g) TMC-2A, TMC-2B, or TMC-2C;
(4h) Dipeptide nitriles (2-cyanopyrrolodides);
(4i) CD26 inhibitors; and
(4j) SDZ 274-444;
(5) glucagon antagonists such as AY-279955; and
(6) amylin agonists which include, but are not limited to, pramlintide (AC-137, Symlin, tripro-amylin or pramlintide acetate).

Known anti-diabetic agents include insulin, sulfonylureas, biguanides, meglitinides, AGI's (Alpha-Glucosidase Inhibitors; e.g., Glyset), PPAR alpha agonists, and PPAR gamma agonists, and dual PPAR alpha/gamma agonists.

Examples of lipid lowering agents include bile acid sequestrants, fibric acid derivatives, nicotinic acid, and HMGCoA reductase inhibitors. Specific examples include statins such as LIPITOR®, ZOCOR®, PRAVACHOL®, LESCOL®, and MEVACOR®, and pitavastatin (nisvastatin) (Nissan, Kowa Kogyo, Sankyo, Novartis) and extended release forms thereof, such as ADX-159 (extended release lovastatin), as well as Colestid, Locholest, Questran, Atromid, Lopid, and Tricor.

Examples of blood pressure lowering agents include antihypertensive agents, such as angiotensin-converting enzyme (ACE) inhibitors (Accupril, Altace, Captopril, Lotensin , Mavik, Monopril, Prinivil, Univasc, Vasotec, and Zestril), adrenergic blockers (such as Cardura, Dibenzyline, Hylorel, Hytrin, Minipress, and Minizide) alpha/beta adrenergic blockers (such as Coreg, Normodyne, and Trandate), calcium channel blockers (such as Adalat, Calan, Cardene, Cardizem, Covera-HS, Dilacor, DynaCirc, Isoptin, Nimotop, Norvace, Plendil, Procardia, Procardia XL, Sula, Tiazac, Vascor, and Verelan), diuretics, angiotensin II receptor antagonists (such as Atacand, Avapro, Cozaar, and Diovan), beta adrenergic blockers (such as Betapace, Blocadren, Brevibloc, Cartrol, Inderal, Kerlone, Lavatol, Lopressor, Sectral, Tenormin, Toprol-XL, and Zebeta), vasodilators (such as Deponit, Dilatrate, SR, Imdur, Ismo, Isordil, Isordil Titradose, Monoket, Nitro-Bid, Nitro-Dur, Nitrolingual Spray, Nitrostat, and Sorbitrate), and combinations thereof (such as Lexxel, Lotrel, Tarka, Teczem, Lotensin HCT, Prinzide, Uniretic, Vaseretic, Zestoretic).

In addition, a second RXR or RAR modulator, as described above in Section B), may also be utilized as a third antidiabetic agent, provided that it is different from the first RXR or RAR modulator.

F) Biological Examples

ABCA1 bDNA Assay

THP-1 cells, a human monocytic cell line, were obtained from ATCC and maintained in RPMI (Gibco) supplemented with 10% fetal bovine serum (Gibco), 2mM L-glutamine and 1% antibiotic-antimycotic in 5% $CO_2$ at 37° C. For ABCA1 mRNA induction assays, the cells were pelleted and resuspended in RPMI supplemented with 0.5% charcoal treated serum (Hyclone), 2 mM glutamine and 1% antibiotic-antimycotic. The cells were plated at a density of 40,000 cells/ 90 µl and incubated as above for at least 4 hours before the initiation of treatments. Compounds were prepared as 10 mM stocks in DMSO. For treatments, the compounds were diluted in medium and 10 µl of 10× stocks were added to the cells at a final concentration 0.1% DMSO. The cells were incubated for the desired amount of time (usually 18-24 hrs) and then lyzed with 50 µl of Quantigene HV bDNA lysis buffer which also contained the ABCA1 bDNA probes (probe sequences shown below):

| Primer Name | ABCA1 bDNA probe sequences Sequence |
|---|---|
| hABC1001 | CGGGTAACGGAAACAGGGGTTGTTTTCTCTTGGAAAGAAAGT |
| hABC1002 | TCCGGGAGCCTCCCCAGGAGTTTTTCTCTTGGAAAGAAAGT |
| hABC1003 | GCCAGTTTCTCCCTTGGTAGTTTTCTCTTGGAAAGAAAGT |
| hABC1004 | CTCCTTGCTCGGGAAGGGTTTTTCTCTTGGAAAGAAAGT |
| hABC1005 | AACAGCTCCTGGGCCAGAGTTTTTCTCTTGGAAAGAAAGT |
| hABC1006 | TTCACCCCCCCTCCCTCGGGATTTTTTCTCTTGGAAAGAAAGT |
| hABC1007 | ATGCGGGAAACAGGACTAGTTTTTCTCTTGGAAAGAAAGT |
| hABC1008 | GTTCACCTCAGCCATGACCTTTTTTCTCTTGGAAAGAAAGT |
| hABC1009 | CATGCCTTCCAGATCATGGAACTTTTTCTCTTGGAAAGAAAGT |
| hABC1010 | GCGAGCCACAATGGATTTTTTTAGGCATAGGACCCGTGTCT |
| hABC1011 | CTCCGAGCATCTGAGAACAGTTTTTAGGCATAGGACCCGTGTCT |
| hABC1012 | TCAGAACTTTGCGCATGTCCTTTTTTAGGCATAGGACCCGTGTCT |
| hABC1013 | GGATTTCTTGATCTGCTGTAATGTTCTTTTTAGGCATAGGACCCGTGTCT |
| hABC1014 | AAGCTTTCATTGTCCACCAGGAATTTTTAGGCATAGGACCCGTGTCT |
| hABC1015 | GGTTGTGATACAGGAACCCAGAGTTTTTAGGCATAGGACCCGTGTCT |
| hABC1016 | GTCCACAGTAGACTTTGGGAGAGATTTTTAGGCATAGGACCCGTGTCT |
| hABC1017 | TGACATCAGCCCTCAGCATCTTTTTTTAGGCATAGGACCCGTGTCT |
| hABC1018 | CTTGTCAAATGTAACTGGTACCCTTTTTTAGGCATAGGACCCGTGTCT |
| hABC1019 | CTGATTTTGATCCATTGCACAGATTTTTAGGCATAGGACCCGTGTCT |
| hABC1020 | GGCTTCAGGATGTCCATGTTGTTTTTAGGCATAGGACCCGTGTCT |
| hABC1021 | AGATGTAGAGTTTAGTGTTCTCAGGATTTTTTAGGCATAGGACCCGTGTCT |
| hABC1022 | TTTTGTGGCTTCGGCCAGTTTTTAGGCATAGGACCCGTGTCT |
| hABC1023 | TCCCAAGACTATGCAGCAATGTTTTTTAGGCATAGGACCCGTGTCT |
| hABC1024 | GTCACTCCAGCTTCTCATGCTGTTTTTAGGCATAGGACCCGTGTCT |

-continued

ABCA1 bDNA probe sequences

| Primer Name | Sequence |
|---|---|
| hABC1025 | GAAACATCACCTCCTGTCGCATTTTTTAGGCATAGGACCCGTGTCT |
| hABC1026 | GCCTGGTAGATTTGGGTGGTTTTTAGGCATAGGACCCGTGTCT |
| hABC1027 | GCCCGCAGACAATACGAGACACATTTTTAGGCATAGGACCGTGTCT |
| hABC1028 | GGCTTTGTAGTTGTTGTCCTCTTTTTAGGCATAGGACCCGTGTCT |
| hABC1029 | TGCCATTGCCTCCAAAGAGTTTTTAGGCATAGGACCCGTGTCT |
| hABC1030 | AAGGTTTCAGCATCTTCCTCAGTTTTTAGGCATAGGACCCGTGTCT |
| hABC1031 | TGCAGTAAGGAGTTGTAGAGTTGTCATAGTTTTTAGGCATAGGACCCGTGTCT |
| hABC1032 | ACTCCAAATTCTTCATCAAATCATTTTTAGGCATAGGACCCGTGTCT |
| hABC1033 | CGGCTTCAGAGCTTTCCAGATATTTTTAGGCATAGGACCCGTGTCT |
| hABC1034 | GTTAAAGTTTCCAACAAC |
| hABC1035 | TGTATAAAAGAAGC |
| hABC1036 | TCATGCTGGTGTCTTTCTGGC |
| hABC1037 | ATCTTGAAGCTTCAAGTTTGAGCT |
| hABC1038 | GCAAAAATACCTTGTGGAGAA |
| hABC1039 | GGTCACCAAGTTGAATCATCTCTT |
| hABC1040 | GCCACAAAGCTCAGAAACTTCTT |
| hABC1041 | GAACGAAGTACTCGCTCTGCTGCA |
| hABC1042 | AGGAGCTGGAGCTGTTCACATTGGTCA |
| hABC1043 | ATACCAGTTGAGAGACTTGATC |
| hABC1044 | ATACAGGATCTTCCCAACGAGCAG |
| hABC1045 | GCCTTGTGGCTGGAGTGTCAGGTGT |
| hABC1046 | ACAGCCAGTTCCTGGAAGGTCTT |

RXR Co-transfection Assay

The nucleic acid sequence from 676-1464bp (accession number X52773) encoding the ligand binding domains was subcloned into the pM vector (BD Biosciences Clontech, Palo Alto, Calif.) and were fused with the DNA binding domain of yeast GAL4. HEK293 cells were cultured in DMEM/F12 medium supplemented with 10% FBS and 1% 1-glutamine (growth medium). Cells were seeded at a density of $5\text{-}10 \times 10^6$ cells in 50 ml of growth medium and left overnight. The medium was removed and the cells were washed with 15 ml of OptiMEM serum free medium (Invitrogen Corp). The cells were transfected using OptiMEM serum free medium and DMRIE transfection reagent (Invitrogen Corp). Approximately 10-30 ng of DNA for the different receptors and 5-10 ng of the luciferase reporter (1:1 ratio for RAR and 4:1 ratio for RXR of receptor DNA:reporter DNA) were gently mixed with 51 µl of DMRIE reagent in a total volume of 17 ml of OptiMEM medium. Eighteen hours after transfection, the cells were washed once with growth medium and then incubated for 6 hrs in 30 ml of growth medium. The cells were then trypsinized, and reseeded at a density of 50,000 per well in 96 well plates and left overnight. The medium was replaced with 90 µl of medium containing DMEM/F12 supplemented with 0.5% charcoal-treated FBS (HyClone; Logan, Utah) and 1% glutamine. Compounds or vehicle were added in 10 µl of 10× concentration of compound or vehicle (0.1% dimethyl sulfoxide). The cells were treated for 16-18 hours, lysed and assayed for luciferase activity using the Steady Gio luciferase assay kit (Promega, Madison, Wis.).

Compounds listed in Table II below were tested in the above assay(s):

TABLE II

| Compound # | ABCA1 $EC_{50}$ in nM (% max MX-6054) | RXR co-transfection $EC_{50}$ in nM (% of 2,4-thiazolidinedione, 5-[[3-(1-ethyl-1,2,3,4-tetrahydro-4,4,6-trimethyl-2-oxo-7-quinolinyl)-4-(trifluoro-methoxy)phenyl]methylene]-, (5Z)-) |
|---|---|---|
| 1 | 39.7 | 179.6 (96%) |
|  |  | 188.7 (63%) |
|  |  | 151 (100%) |
| 2 | >2000 | >2000 |
| 3 | >2000 (8.4% @3 µM) | >2000 |
| 4 | 430 (79% @3 µM) | 98.8 (77%) |
| 5 | >2000 | >2000 |
| 6 | >2000 | — |
| 7 | >2000 | — |
| 8 | >2000 | — |
| 9 | >2000 | — |
| 10 | >2000 (37.2% @3 µM) | 1400 (28%) |
| 11 | >2000 (75.5% @3 µM) | 61.2 (86%) |
| 12 | >2000 | 709 (100%) |
| 13 | >2000 | 347 (100%) |
| 14 | >2000 | — |
| 15 | >2000 | — |
| 16 | >2000 | — |
| 17 | >2000 | — |
| 18 | >2000 (4.5%% @3 µM) | >2000 |
| 19 | >2000 | — |
| 20 | >2000 | — |
| 21 | >2000 | — |
| 22 | >2000 (28.6% @3 µM) | 385 (62%) |
| 23 | >2000 (64.1% @3 µM) | 719 (72%) |
| 24 | >2000 | — |
| 25 | >2000 | — |
| 26 | >2000 | >2000 |
| 27 | >2000 (92) | — |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:

1. A compound of Formula I

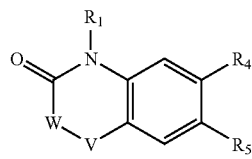
(I)

wherein $R_1$ is H or $C_{1-3}$alkyl;

W is

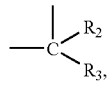

V is —O—, wherein $R_2$ and $R_3$ can be the same or different, each being independently selected from H and optionally substituted $C_{1-3}$alkyl;

$R_4$ is independently

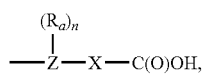

wherein

Z is selected from

X is selected from a bond, optionally substituted —O—$C_{1-5}$alkyl, and optionally substituted $C_{1-6}$alkylene;

$R_a$ is optionally substituted $C_{1-3}$alkoxy; and n is 0, 1, 2, or 3;

or alternatively $R_4$ is H or optionally substituted $C_{1-3}$alkyl;

with the proviso that when $R_4$ is

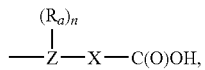

then $R_5$ cannot be

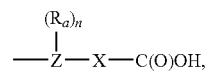

provided further that when $R_4$ is H or optionally substituted $C_{1-3}$alkyl, then $R_5$ cannot be H or optionally substituted $C_{1-3}$alkyl;

and $R_5$ is independently

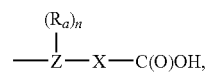

wherein

Z is selected from

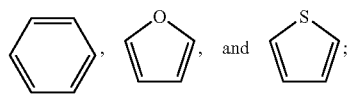

X is selected from a bond, optionally substituted —O—$C_{1-5}$alkyl-, and optionally substituted $C_{1-6}$alkylene;

$R_a$ is optionally substituted $C_{1-3}$alkoxy; and n is 0, 1, 2, or 3;

or alternatively $R_5$ is H or optionally substituted $C_{1-3}$alkyl;

with the proviso that when $R_5$ is

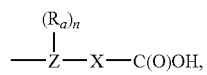

then R₄ cannot be

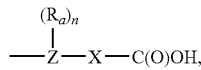

provided further that when $R_5$ is H or optionally substituted $C_{1-3}$alkyl, then $R_4$ cannot be H or optionally substituted $C_{1-3}$alkyl;

or pharmaceutically acceptable salts thereof.

2. The compound of claim 1 wherein $R_1$ is H or $C_{1-3}$alkyl.

3. The compound of claim 1 wherein $R_2$ and $R_3$ are independently selected from H and $C_{1-3}$alkyl.

4. The compound of claim 1 wherein Z is

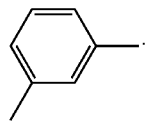

5. The compound of claim 1 wherein $R_4$ or $R_5$ is

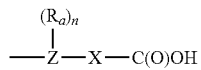

wherein Z is

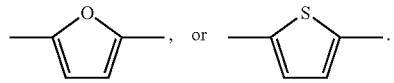

6. The compound of claim 1 wherein $R_4$ or $R_5$ is

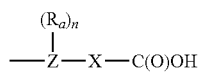

wherein X is a bond.

7. The compound of claim 1 wherein $R_4$ or $R_5$ is

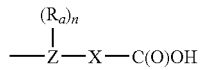

wherein X is optionally substituted $C_{1-5}$alkylene.

8. The compound of claim 7 wherein the $C_{1-5}$alkylene is saturated.

9. The compound of claim 8 wherein the $C_{1-5}$alkylene is

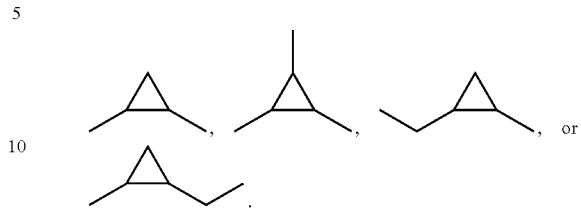

10. The compound of claim 9 wherein 1, 2, or 3 of the hydrogen atoms in the $C_{1-5}$alkylene is further substituted with halo.

11. The compound of claim 1 wherein $R_4$ or $R_5$ is

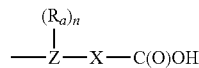

wherein X is optionally substituted $C_{1-6}$alkylene.

12. The compound of claim 11 wherein the $C_{1-6}$alkylene is saturated.

13. The compound of claim 12 wherein the $C_{1-6}$alkylene is

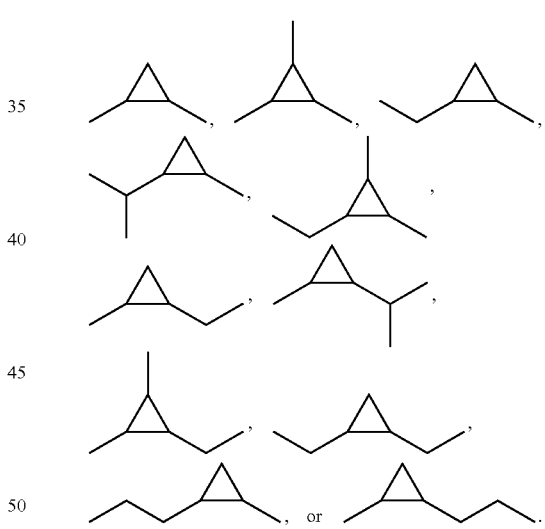

14. The compound of claim 13 wherein 1, 2, or 3 of the hydrogen atoms in the $C_{1-6}$alkylene is further substituted with halo.

15. The compound of claim 7 wherein the alkylene is unsaturated.

16. The compound of claim 15 wherein the alkylene contains a double or triple bond.

17. The compound of claim 11 wherein the alkylene is unsaturated.

18. The compound of claim 17 wherein the alkylene contains a double or triple bond.

19. The compound of claim 1 wherein $R_a$ is H.

20. The compound of claim 1 wherein $R_a$ is —OCF₃, —OCH₃, —OCH₂CF₃, or —CH=CH—C(O)OH.

21. The compound of claim 1, wherein
$R_1$ is —$CH_3$, —$CH_2CH_3$, or —$CH(CH_3)_2$;
$R_2$ and $R_3$ are independently selected from H, —$CH_3$, —$CH_2CH_3$, and —$CH(CH_3)_2$;
$R_4$ is

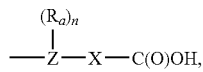

wherein
Z is

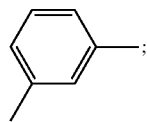

X is selected from

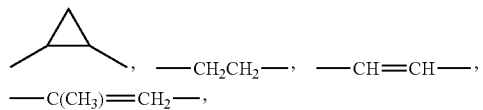

and —CH=C(CH$_3$)—; and $R_a$ is —$OCF_3$ or —$OCH_2CF_3$; and
n is 1;
or alternatively $R_4$ is —$CH_3$;
with the proviso that when $R_4$ is

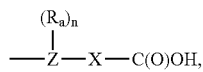

then $R_5$ cannot be

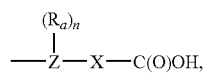

provided further that when $R_4$ is —$CH_3$, then $R_5$ cannot be —$CH_3$,
and $R_5$ is

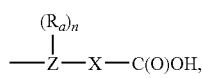

wherein
Z is

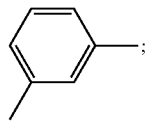

X is selected from

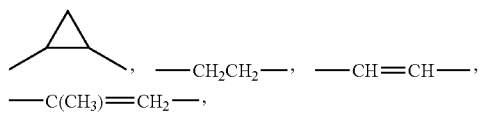

and —CH=C(CH$_3$)—; and
$R_a$ is —$OCF_3$ or —$OCH_2CF_3$; and
n is 1;
or alternatively $R_5$ is —$CH_3$;
with the proviso that when $R_5$ is

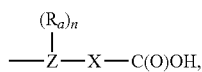

then $R_4$ cannot be

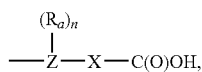

provided further that when $R_5$ is CH$_3$, then $R_4$ cannot be —$CH_3$.

22. A pharmaceutical composition comprising at least one compound of claim 1 and at least one pharmaceutically acceptable carrier.

23. A method for treating a retinoid x receptor (RXR) mediated condition in a subject in need thereof comprising administering to the subject a therapeutically effective amount of at least one compound of claim 1, wherein the RXR condition is selected from Type 2 diabetes mellitus, hynercholesterolemia, insulin resistance, dyslipidemia, artherosclerosis, hypertension, schemia, irritable bowel disorder and cataracts.

24. The method of claim 23 wherein the RXR condition is selected from Type 2 diabetes mellitus, dyslipidemia, hypercholesterolemia, and associated symptoms or complications thereof.

25. A method for inhibiting the onset of a RXR mediated condition in a subject in need thereof, comprising administering to said subject a therapeutically effective amount of at least one compound according to claim 1, wherein the RXR condition is selected from Type 2 diabetes mellitus, hynercholesterolemia, insulin resistance, dyslipidemia, artherosclerosis, hypertension, ischemia, irritable bowel disorder and cataracts.

26. The method of claim 25 wherein the RXR condition is selected from type 2 diabetes mellitus, dyslipidemia, hypercholesterolemia, and associated symptoms or complications thereof.

27. A process for making a pharmaceutical composition comprising admixing any of the compounds according to claim 1 and a pharmaceutically acceptable carrier.

28. The method of claim 23 wherein the therapeutically effective amount of the compound of claim 1 is from about 0.001 mg/kg/day to about 5 mg/kg/day.

* * * * *